US012577290B2

(12) United States Patent
Bethune et al.

(10) Patent No.: US 12,577,290 B2
(45) Date of Patent: Mar. 17, 2026

(54) FASL EXPRESSION AND FASR GENE KNOCKOUT TO PROTECT THERAPEUTIC CELLS FROM ALLOGENEIC REJECTION AND ACTIVATION-INDUCED CELL DEATH

(71) Applicant: Allogene Therapeutics, Inc., South San Francisco, CA (US)

(72) Inventors: Michael Thomas Bethune, Castro Valley, CA (US); Eric Hans Gschweng, Oak Park, CA (US); Thomas John Van Blarcom, Oakland, CA (US); Cesar Adolfo Sommer, San Mateo, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 792 days.

(21) Appl. No.: 17/687,193

(22) Filed: Mar. 4, 2022

(65) Prior Publication Data

US 2022/0281950 A1     Sep. 8, 2022

Related U.S. Application Data

(60) Provisional application No. 63/156,902, filed on Mar. 4, 2021.

(51) Int. Cl.
| | |
|---|---|
| *A61K 40/11* | (2025.01) |
| *A61K 40/31* | (2025.01) |
| *A61K 40/42* | (2025.01) |
| *A61P 37/06* | (2006.01) |
| *C07K 14/705* | (2006.01) |
| *C12N 5/0783* | (2010.01) |
| *C12N 9/22* | (2006.01) |
| *C12N 15/11* | (2006.01) |
| *C12N 15/86* | (2006.01) |
| *C12N 15/90* | (2006.01) |

(52) U.S. Cl.
CPC ........ *C07K 14/70575* (2013.01); *A61K 40/11* (2025.01); *A61K 40/31* (2025.01); *A61K 40/4215* (2025.01); *A61P 37/06* (2018.01); *C12N 5/0636* (2013.01); *C12N 9/22* (2013.01); *C12N 15/11* (2013.01); *C12N 15/86* (2013.01); *C12N 15/907* (2013.01); *C12N 2310/20* (2017.05); *C12N 2510/00* (2013.01); *C12N 2740/15043* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,037,743 A | 8/1991 | Welch et al. |
| 5,143,830 A | 9/1992 | Holland et al. |
| 5,858,358 A | 1/1999 | June et al. |
| 5,883,223 A | 3/1999 | Gray et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Brenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,709,226 B2 | 5/2010 | Foote |

(Continued)

FOREIGN PATENT DOCUMENTS

| | | |
|---|---|---|
| CN | 110790842 A | 2/2020 |
| WO | 2002072798 A1 | 9/2002 |
| WO | 2016069282 A1 | 5/2016 |

(Continued)

OTHER PUBLICATIONS

Loeff et al., Transplant Immunology, vol. 57, Dec. 2019, 101209, pp. 1-9 (Year: 2019).*
Chen et al., Nature Biotechnology, vol. 16, Nov. 1998 (Year: 1998).*
Xiao et al., The Journal of Immunology, 2004, 173: 5095-5102 (Year: 2004).*
EPO , "International Search Report and Written Opinion", mailed on Jul. 13, 2022 for international application No. PCT US2022/018964; 21 pages.
Rosenberg, Steven A., et al., "Adoptive cell transfer: a clinical path to effective cancer immunotherapy", Nat Rev Cancer. Apr. 2008 ; 8(4): 299-308. doi:10.1038/nrc2355.

(Continued)

*Primary Examiner* — Evelyn Y Pyla

(74) *Attorney, Agent, or Firm* — Allogene Therapeutics, Inc.

(57) ABSTRACT

Compositions, methods, expression vectors and engineered immune cells for improving therapies that entail the administration of allogeneic cells to a patient. An immune cell, e.g., a T cell, modified to comprise and/or express FasL protein or a FasL protein derivative from, for example, an expression vector comprising a polynucleotide that encodes FasL protein or a FasL protein derivative, and to express FasR at a reduced level, and further modified to comprise and/or express an antigen binding protein e.g., a chimeric antigen receptor (CAR). An improved method of CAR T-cell therapy that comprises administering the improved immune cells, and compositions that comprise the improved immune cells. Methods of improving persistence of administered cells and reducing activation-induced cell death comprising administering the improved cells.

22 Claims, 19 Drawing Sheets

Specification includes a Sequence Listing.

(56) References Cited

U.S. PATENT DOCUMENTS

2006/0121005 A1    6/2006   Berenson et al.

FOREIGN PATENT DOCUMENTS

WO        2019094847  A1     5/2019
WO        2020069508  A1     4/2020
WO        2020088631  A1     5/2020
WO        2021205175  A1    10/2021
WO        2022012531  A1     1/2022

OTHER PUBLICATIONS

Roth, Theodore L., et al., "Rapid discovery of synthetic DNA sequences to rewrite endogenous T cell circuits", bioRxiv 604561 (2019). doi:10.1101/604561.
Sadelain, Michel , et al., "The promise and potential pitfalls of chimeric antigen receptors", Current Opinion in Immunology 2009, 21:215-223.
Saitou, Naruya , et al., "The neighbor-joining method: a new method for reconstructing phylogenetic trees", Molecular Biology and Evolution, vol. 4, Issue 4, Jul. 1987, pp. 406-425, https://doi.org/10.1093/oxfordjournals.molbev.a040454.
Sambrook, J. , et al., "Molecular Cloning: A Laboratory Manual", Second Ed., Cold Spring Harbor Laboratory Press, 1989 (TOC).
Schneider, Pascal , et al., "Characterization of Fas (Apo-1, CD95)-Fas ligand interaction", J Biol Chem; Jul. 25, 1997;272(30):18827-33. doi: 10.1074/jbc.272.30.18827.
Shepherd, Philip , et al., "Monoclonal Antibodies: A Practical Approach", Oxford University Press, 2000 (TOC).
Sneath, Peter H.A., et al., "Numerical Taxonomy—The Principles and Practice of Numerical Classification", Nature 193, 855-860 (1962) W. H. Freeman and Co. (TOC).
Sridharan, Kannan , et al., "Therapeutic nucleic acids: current clinical status", Br J Clin Pharmacol (2016) 82 659-672.
Takahashi, Tomohiro , et al., "Generalized lymphoproliferative disease in mice, caused by a point mutation in the fas ligand", Cell; Mar. 25, 1994;76(6):969-76. doi: 10.1016/0092-8674(94)90375-1.
Tramontano, Anna , et al., "Framework Residue 71 is a Major Determinant of the Position and Conformation of the Second Hypervariable Region in the V H Domains of Immunoglobulins", J. Mol. Biol. (1990) 215, 175-182.
Watanabe-Fukunaga, Rie , et al., "Lymphoproliferation disorder in mice explained by defects in Fas antigen that mediates apoptosis", Nature; Mar. 26, 1992;356(6367):314-7. doi: 10.1038/356314a0.
Wilbur, W. J., et al., "Rapid Similarity Searches of Nucleic Acid and Protein Data Banks", 1983, Proc. Natl. Acad. Sci. USA vol. 80, pp. 726-730.
Willems, Fabienne , et al., "Expression of c-FLIP(L) and resistance to CD95-mediated apoptosis of monocyte-derived dendritic cells: inhibition by bisindolylmaleimide", Blood; Jun. 1, 2000;95(11):3478-82.
Xerri, Luc , et al., "Fas ligand is not only expressed in immune privileged human organs but is also coexpressed with Fas in various epithelial tissues", Mol Pathol; Apr. 1997;50(2):87-91. doi: 10.1136/mp.50.2.87.
Yamamoto, Tori N., et al., "T cells genetically engineered to overcome death signaling enhance adoptive cancer immunotherapy", The Journal of Clinical Investigation,vol. 129, No. 4, Jan. 29, 2019 (Jan. 29, 2019), p. 1551-1565; DOI: 10.1172/JCI121491; ISSN:0021-9738.
Yolcu, Esma S., et al., "Pancreatic Islets Engineered with SA-FasL Protein Establish Robust Localized Tolerance by Inducing Regulatory T Cells in Mice", J Immunol; Dec. 1, 2011;187(11):5901-9. doi: 10.4049/jimmunol.1003266.
Zanetti, Maurizio , et al., "The Antibodies", vol. 1, Harwood Academic Publisher, 1995, Luxembourg (TOC).
Al-Lazikani, Bissan , et al., "Standard Conformations for the Canonical Structures of Immunoglobulins", J. Mol. Biol. (1997) 273, 927-948.

Atkins, J. F., et al., "A case for "StopGo": Reprogramming translation to augment codon meaning of GGN by promoting unconventional termination (Stop) after addition of glycine and then allowing continued translation (Go)", RNA (2007), 13:803-810., Cold Spring Harbor Laboratory Press.
Ausubel, Frederick M., et al., "Short Protocols in Molecular Biology", A Compendium of Methods from Current Protocols in Molecular Biology; 4th ED.; Wiley and Sons, 1999; (TOC).
Bird, Robert E., et al., "Single Chain Antigen-Binding Proteins", Science, vol. 242, Issue 4877, Oct. 21, 1988; DOI: 10.1126/science.3140379.
Brenner, Malcom K., et al., "Adoptive T Cell Therapy of Cancer", Curr Opin Immunol. Apr. 2010 ; 22(2): 251-257. doi:10.1016/j.coi.2010.01.020.
Catty, D. , "Antibodies: a practical approach", IRL Press Ltd. 1988, Oxford England (TOC).
Celis, Julio E., "Cell Biology: A Laboratory Hnadbook", Academic Press, 1998 (TOC).
Chothia, Cyrus , et al., "Canonical structures for the hypervariable regions of immunoglobulins", J Mol Biol; Aug. 20, 19870196(4):901-17. doi: 10.1016/0022-2836(87)90412-8.
Chothia, Cyrus , et al., "Conformations of immunoglobulin hypervariable regions", Nature. vol 342 . Dec. 21/28, 1989.
Chothia, Cyrus , et al., "Structural Repertoire of the Human VH Segments", J. Mol. Biol. (1992) 227, 799-917.
Coligan, John E., et al., "Current Protocols in Immunology", vol. 1, 1991, John Wiley & Sons, Inc.(TOC).
Dayhoff, M. O., "A model of evolutionary change in proteins—Matrices for detecting distant relationships", Atlas of Protein sequence and structure, pp. 345-352, 1978.
Donnelly, Michelle , et al., "Fluorescent Tagging of Herpes Simplex Virus Tegument Protein VP13/14 in Virus Infection", Journal of Virology, vol. 75, No. 6, Mar. 2001, p. 2575-2583.
Donnelly, Michelle , et al., "Nuclear Localization and Shuttling of Herpes Simplex Virus Tegument Protein VP13/14", Journal of Virology, vol. 75, No. 6, Mar. 2001, p. 2566-2574.
Doronina, Victoria A., et al., "Site-Specific Release of Nascent Chains from Ribosomes at a Sense Codon", Molecular and Cellular Biology, vol. 28, No. 13, Jul. 2008, p. 4227-4239.
Doyle, Alan , et al., "Cell and Tissue Culture: Laboratory Procedures in Biotechnology", John Wiley & Sons, Ltd., West Sussex, England, 1998 (TOC).
Eshhar, Zelig , et al., "Specific activation and targeting of cytotoxic lymphocytes through chimeric single chains consisting of antibody-binding domains and the gamma or zeta subunits of the immunoglobulin and T-cell receptors.", Immunology; Proc Natl Acad Sci U S A. Jan. 15, 1993; 90(2): 720-724.
Fellouse, F. A., "High-throughput Generation of Synthetic Antibodies from Highly Functional Minimalist Phage-displayed Libraries", J. Mol. Biol.; 2007; 373; 924-940.
Finch, Peter , "Antibodies", 1st Ed., Stride Publications, 1997 (TOC).
Fisher, Galen H., et al., "Dominant interfering Fas gene mutations impair apoptosis in a human autoimmune lymphoproliferative syndrome", Cell; Jun. 16, 1995;81(6):935-46. doi: 10.1016/0092-8674(95)90013-6.
Gait, M. J., "Oligonucleotide Synthesis: A Practical Approach", IRL Press Ltd., Oxford, England, 1984 (TOC).
Gaj, Thomas , et al., "Genome-Editing Technologies: Principles and Applications", Cold Spring Harbor Perspective in Biology; 2016;8:a023754.
Genbank , accession No. AAA53133 4-1BB *Homo sapiens*; total 2 pages.
Genbank , accession No. NP_006130.1, T-cell-specific surface glycoprotein CD28 isoform 1 precursor, *Homo sapience*, total 4 pages.
Graham, Charlotte , et al., "Allogeneic CAR-T Cells: More than Ease of Access?", Cells 2018, 7, 155; doi:10.3390/cells7100155.
Harlow, Ed , et al., "Epitope Mapping", Using Antibodies: A Laboratory Manual, Chapter 11, Cold Spring Harbor Laboratory Press, NY, 1998.
Hein, J. , et al., "Unified Approach to Alignment and Phylogenies", Methods in Enzymology, vol. 183, 1990.

(56) References Cited

OTHER PUBLICATIONS

Higgins, Desmond G., et al., "Fast and sensitive multiple sequence alignments on a microcomputer", 1989, Cabios 5:151-153.

Janeway, Charles A., et al., "Immunobiology", Churchill Livingstone; 2nd Edition, Sep. 1, 1997, (TOC).

Jayasena, S. D., et al., "Aptamers: an emerging class of molecules that rival antibodies in diagnostics", Clin Chem. Sep. 1999;45(9):1628-50.

Joglekar, Alok V., et al., "T cell antigen discovery via signaling and antigen-presenting bifunctional receptors", Nat Methods; Feb. 2019;16(2):191-198. doi: 10.1038/s41592-018-0304-8. Epub Jan. 28, 2019.

Kabat, Elvin A., et al., "Sequences of Proteins of Immunological Interest", 5th Ed. NIH publication, No. 91-3242; 1992 (TOC).

Kunkele, Annette , et al., "Functional Tuning of CARs Reveals Signaling Threshold above Which CD8+ CTL Antitumor Potency Is Attenuated due to Cell Fas-FasL-Dependent Aicd", Cancer Immunology Research, vol. 3, No. 4, Apr. 1, 2015 (Apr. 1, 2015), p. 368-379, DOI: 10.1158/2326-6066.CIR-14-0200; ISSN:2326-6066.

Lam, Jenny KW, et al., "siRNA Versus miRNA as Therapeutics for Gene Silencing", Molecular Therapy—Nucleic Acids (2015) 4, e252; doi:10.1038/mtna.2015.23.

Lau, Henry T., et al., "Prevention of islet allograft rejection with engineered myoblasts expressing FasL in mice", Science; Jul. 5, 1996;273(5271):109-12. doi: 10.1126/science.273.5271.109.

Li, Jie-Hui , et al., "Immune privilege and FasL: two ways to inactivate effector cytotoxic T lymphocytes by FasL-expressing cells", Immunology; Mar. 2002;105(3):267-77. doi: 10.1046/j.1365-2567.2002.01380.x.

Lundqvist, Andreas , et al., "Mature dendritic cells are protected from Fas/CD95-mediated apoptosis by upregulation of Bcl-X(L)", Cancer Immunol Immunother; May 2002;51(3):139-44. doi: 10.1007/s00262-002-0265-7. Epub Mar. 1, 2002.

Maccallum, Robert M., et al., "Antibody-antigen Interactions: Contact Analysis and Binding Site Topography", J. Mol. Biol. (1996) 262, 732-745.

Makabe, Koki , et al., "Thermodynamic Consequences of Mutations in Vernier Zone Residues of a Humanized Anti-human Epidermal Growth Factor Receptor Murine Antibody, 528", The Journal of Biological Chemistry vol. 283, No. 2, pp. 1156-1166, Jan. 11, 2008.

Margalit, Alon , et al., "Chimeric beta2 microglobulin/CD3zeta polypeptides expressed in T cells convert MHC class I peptide ligands into T cell activation receptors: a potential tool for specific targeting of pathogenic CD8(+) T cells", Int Immunol; Nov. 2003;15(11):1379-87. doi: 10.1093/intimm/dxg136.

Mather, Jennie P., et al., "Introduction to Cell and Tissue Culture: Theory and Techique", Plem Press, New Yord, NY, 1998, (TOC).

Matsue, Hiroyuki , et al., "Induction of antigen-specific immunosuppression by CD95L cDNA-transfected 'killer' dendritic cells", Nat Med; Aug. 1999;5(8):930-7. doi: 10.1038/11375.

Miller, Jeffrey H., et al., "Gene Transfer Vectors for Mammalian Cells", Current Communications in Molecular Biology, Cold Spring Harbor Laboratory, 1987 (TOC).

Mullis , et al., "PCR: The Polymerase Chain Reaction", Birkauswer Press, Boston, 1994 (Table of Contents).

Myers, E. W., et al., "Optimal Alignments in Linear Space", 1988, Cabios 4:11-17.

Quach, David H., et al., "A strategy to protect off-the-shelf cell therapy products using virus-specific T-cells engineered to eliminate alloreactive T-cells", J Transl Med . Jul. 24, 2019;17(1):240. doi: 10.1186/s12967-019-1988-y.

Remington , "The Science and Practice of Pharmacy", 21st Ed. Mack Publishing, 2005, Table of Contents.

Ren, Jiangtao , et al., "A versatile system for rapid multiplex genome-edited CAR T cell generation", Oncotarget,vol. 8, No. 10, Feb. 9, 2017 (Feb. 9, 2017), p. 17002-17011; DOI: 10.18632/oncotarget.15218 external link.

Rensing-Ehl, Anne , et al., "Local Fas/APO-1 (CD95) ligand-mediated tumor cell killing in vivo", Eur J Immunol; Aug. 1995;25(8):2253-8. doi: 10.1002/eji.1830250821.

Robinson, E. D., "Comparison of Labeled Trees with Valency Three", 1971, Comb. Theor. 11:105-119.

* cited by examiner

FIG. 6B

Host T Cell
(HLA-A2⁻)

Graft T Cell
(HLA-A2⁺)

F5 TCR
TRAC KO

MART1
TRAC KO

MART1
FasR/TRAC KO

○ A2+ Graft T cells: KO TRAC +/- FasR + MART1 Ag transduced
○ A2- Graft T cells: KO TRAC          +/- F5 TCR transduced

SEQUENCE LISTING

```
<160> NUMBER OF SEQ ID NOS: 38

<210> SEQ ID NO 1
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asn His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Ile Arg Gly Val Asn Phe Thr Ser
        115                 120                 125

Asn Gly Pro Val Met Gln Lys Lys Thr Leu Gly Trp Glu Ala Phe Thr
    130                 135                 140
```

```
Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ile Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asn Glu
            195                 200                 205

Thr Tyr Val Glu Gln His Glu Val Ala Val Ala Arg Tyr Cys Asp Leu
        210                 215                 220

Pro Ser Lys Leu Gly His Lys Leu Asn
225                 230
```

<210> SEQ ID NO 2
<211> LENGTH: 28
<212> TYPE: PRT
<213> ORGANISM: Teschovirus A

<400> SEQUENCE: 2

```
Gly Gly Ser Gly Gly Arg Ala Lys Arg Ala Thr Asn Phe Ser Leu Leu
1               5                   10                  15

Lys Gln Ala Gly Asp Val Glu Glu Asn Pro Gly Pro
            20                  25
```

<210> SEQ ID NO 3
<211> LENGTH: 281
<212> TYPE: PRT
<213> ORGANISM: Homo sapiens

<400> SEQUENCE: 3

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
            35                  40                  45

Pro Pro Pro Pro Pro Leu Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
        130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205
```

-continued

```
His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
                275                 280

<210> SEQ ID NO 4
<211> LENGTH: 80
<212> TYPE: PRT
<213> ORGANISM: Homo sapiens

<400> SEQUENCE: 4

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
                20                  25                  30

Pro Thr Ser Val Pro Arg Arg Pro Gly Gln Arg Arg Pro Pro Pro
                35                  40                  45

Pro Pro Pro Pro Pro Leu Pro Pro Pro Pro Pro Pro Pro Leu Pro
                50                  55                  60

Pro Leu Pro Leu Pro Pro Leu Lys Lys Arg Gly Asn His Ser Thr Gly
65                  70                  75                  80

<210> SEQ ID NO 5
<211> LENGTH: 22
<212> TYPE: PRT
<213> ORGANISM: Homo sapiens

<400> SEQUENCE: 5

Leu Cys Leu Leu Val Met Phe Phe Met Val Leu Val Ala Leu Val Gly
1               5                   10                  15

Leu Gly Leu Gly Met Phe
                20

<210> SEQ ID NO 6
<211> LENGTH: 179
<212> TYPE: PRT
<213> ORGANISM: Homo sapiens

<400> SEQUENCE: 6

Gln Leu Phe His Leu Gln Lys Glu Leu Ala Glu Leu Arg Glu Ser Thr
1               5                   10                  15

Ser Gln Met His Thr Ala Ser Ser Leu Glu Lys Gln Ile Gly His Pro
                20                  25                  30

Ser Pro Pro Pro Glu Lys Lys Glu Leu Arg Lys Val Ala His Leu Thr
                35                  40                  45

Gly Lys Ser Asn Ser Arg Ser Met Pro Leu Glu Trp Glu Asp Thr Tyr
                50                  55                  60

Gly Ile Val Leu Leu Ser Gly Val Lys Tyr Lys Lys Gly Gly Leu Val
65                  70                  75                  80

Ile Asn Glu Thr Gly Leu Tyr Phe Val Tyr Ser Lys Val Tyr Phe Arg
                85                  90                  95
```

```
Gly Gln Ser Cys Asn Asn Leu Pro Leu Ser His Lys Val Tyr Met Arg
            100             105             110

Asn Ser Lys Tyr Pro Gln Asp Leu Val Met Met Glu Gly Lys Met Met
        115             120             125

Ser Tyr Cys Thr Thr Gly Gln Met Trp Ala Arg Ser Ser Tyr Leu Gly
    130             135             140

Ala Val Phe Asn Leu Thr Ser Ala Asp His Leu Tyr Val Asn Val Ser
145             150             155             160

Glu Leu Ser Leu Val Asn Phe Glu Glu Ser Gln Thr Phe Phe Gly Leu
            165             170             175

Tyr Lys Leu
```

```
<210> SEQ ID NO 7
<211> LENGTH: 208
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Asn His Ser Thr Gly Leu Cys Leu Leu Val Met Phe Phe Met
1               5               10              15

Val Leu Val Ala Leu Val Gly Leu Gly Leu Gly Met Phe Gln Leu Phe
            20              25              30

His Leu Gln Lys Glu Leu Ala Glu Leu Arg Glu Ser Thr Ser Gln Met
        35              40              45

His Thr Ala Ser Ser Leu Glu Lys Gln Ile Gly His Pro Ser Pro Pro
    50              55              60

Pro Glu Lys Lys Glu Leu Arg Lys Val Ala His Leu Thr Gly Lys Ser
65              70              75              80

Asn Ser Arg Ser Met Pro Leu Glu Trp Glu Asp Thr Tyr Gly Ile Val
            85              90              95

Leu Leu Ser Gly Val Lys Tyr Lys Lys Gly Gly Leu Val Ile Asn Glu
            100             105             110

Thr Gly Leu Tyr Phe Val Tyr Ser Lys Val Tyr Phe Arg Gly Gln Ser
        115             120             125

Cys Asn Asn Leu Pro Leu Ser His Lys Val Tyr Met Arg Asn Ser Lys
    130             135             140

Tyr Pro Gln Asp Leu Val Met Met Glu Gly Lys Met Met Ser Tyr Cys
145             150             155             160

Thr Thr Gly Gln Met Trp Ala Arg Ser Ser Tyr Leu Gly Ala Val Phe
            165             170             175

Asn Leu Thr Ser Ala Asp His Leu Tyr Val Asn Val Ser Glu Leu Ser
            180             185             190

Leu Val Asn Phe Glu Glu Ser Gln Thr Phe Phe Gly Leu Tyr Lys Leu
        195             200             205
```

```
<210> SEQ ID NO 8
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gln Gln Pro Phe Asn Tyr Pro Tyr Pro Gln Ile Tyr Trp Val Asp
```

-continued

```
1            5              10             15

Ser Ser Ala Ser Ser Pro Trp Ala Pro Pro Gly Thr Val Leu Pro Cys
            20             25             30

Pro Thr Ser Val Pro Arg Arg Pro Gly Gln Arg Arg Pro Pro Pro Pro
            35             40             45

Pro Pro Pro Pro Pro Leu Pro Pro Pro Pro Pro Pro Pro Leu Pro
    50             55             60

Pro Leu Pro Leu Pro Pro Leu Lys Lys Arg Gly Asn His Ser Thr Gly
65             70             75             80

Leu Ala Leu Leu Val Met Phe Phe Met Val Leu Val Ala Leu Val Gly
            85             90             95

Leu Gly Leu Gly Met Phe Gln Leu Phe His Leu Gln Lys Glu Leu Ala
            100            105            110

Glu Leu Arg Glu Ser Thr Ser Gln Met His Thr Ala Ser Ser Leu Glu
            115            120            125

Lys Gln Ile Gly His Pro Ser Pro Pro Pro Glu Lys Lys Glu Leu Arg
    130            135            140

Lys Val Ala His Leu Thr Gly Lys Ser Asn Ser Arg Ser Met Pro Leu
145            150            155            160

Glu Trp Glu Asp Thr Tyr Gly Ile Val Leu Leu Ser Gly Val Lys Tyr
            165            170            175

Lys Lys Gly Gly Leu Val Ile Asn Glu Thr Gly Leu Tyr Phe Val Tyr
            180            185            190

Ser Lys Val Tyr Phe Arg Gly Gln Ser Cys Asn Asn Leu Pro Leu Ser
    195            200            205

His Lys Val Tyr Met Arg Asn Ser Lys Tyr Pro Gln Asp Leu Val Met
    210            215            220

Met Glu Gly Lys Met Met Ser Tyr Cys Thr Thr Gly Gln Met Trp Ala
225            230            235            240

Arg Ser Ser Tyr Leu Gly Ala Val Phe Asn Leu Thr Ser Ala Asp His
            245            250            255

Leu Tyr Val Asn Val Ser Glu Leu Ser Leu Val Asn Phe Glu Glu Ser
            260            265            270

Gln Thr Phe Phe Gly Leu Tyr Lys Leu
    275            280
```

```
<210> SEQ ID NO 9
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gln Gln Pro Phe Asn Tyr Pro Tyr Pro Gln Ile Tyr Trp Val Asp
1            5              10             15

Ser Ser Ala Ser Ser Pro Trp Ala Pro Pro Gly Thr Val Leu Pro Cys
            20             25             30

Pro Thr Ser Val Pro Arg Arg Pro Gly Gln Arg Arg Pro Pro Pro Pro
            35             40             45

Pro Pro Pro Pro Pro Leu Pro Pro Pro Pro Pro Pro Pro Leu Pro
    50             55             60

Pro Leu Pro Leu Pro Pro Leu Lys Lys Arg Gly Asn His Ser Thr Gly
65             70             75             80
```

-continued

```
Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Glu Glu Ala
            115                 120                 125

Ala Ala Ile Gly His Pro Ser Pro Pro Glu Lys Lys Glu Leu Arg
        130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
                260                 265                 270

Gln Thr Phe Phe Gly Leu Tyr Lys Leu
            275                 280

<210> SEQ ID NO 10
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro
            35                  40                  45

Pro Pro Pro Pro Pro Leu Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Asp Ile Gly His Pro Ser Pro Pro Glu Lys Lys Glu Leu Arg
        130                 135                 140

Lys Val Ala His Leu Thr Gly Lys Ser Asn Ser Arg Ser Met Pro Leu
145                 150                 155                 160
```

```
Glu Trp Glu Asp Thr Tyr Gly Ile Val Leu Leu Ser Gly Val Lys Tyr
            165             170             175

Lys Lys Gly Gly Leu Val Ile Asn Glu Thr Gly Leu Tyr Phe Val Tyr
            180             185             190

Ser Lys Val Tyr Phe Arg Gly Gln Ser Cys Asn Asn Leu Pro Leu Ser
            195             200             205

His Lys Val Tyr Met Arg Asn Ser Lys Tyr Pro Gln Asp Leu Val Met
        210             215             220

Met Glu Gly Lys Met Met Ser Tyr Cys Thr Thr Gly Gln Met Trp Ala
225             230             235             240

Arg Ser Ser Tyr Leu Gly Ala Val Phe Asn Leu Thr Ser Ala Asp His
            245             250             255

Leu Tyr Val Asn Val Ser Glu Leu Ser Leu Val Asn Phe Glu Glu Ser
            260             265             270

Gln Thr Phe Phe Gly Leu Tyr Lys Leu
            275             280
```

```
<210> SEQ ID NO 11
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11
```

```
Met Gln Gln Pro Phe Asn Tyr Pro Tyr Pro Gln Ile Tyr Trp Val Asp
1               5               10              15

Ser Ser Ala Ser Ser Pro Trp Ala Pro Pro Gly Thr Val Leu Pro Cys
            20              25              30

Pro Thr Ser Val Pro Arg Arg Pro Gly Gln Arg Arg Pro Pro Pro
            35              40              45

Pro Pro Pro Pro Pro Leu Pro Pro Pro Pro Pro Pro Pro Leu Pro
        50              55              60

Pro Leu Pro Leu Pro Pro Leu Lys Lys Arg Gly Asn His Ser Thr Gly
65              70              75              80

Leu Cys Leu Leu Val Met Phe Phe Met Val Leu Val Ala Leu Val Gly
            85              90              95

Leu Gly Leu Gly Met Phe Gln Leu Phe His Leu Gln Lys Glu Leu Ala
            100             105             110

Glu Leu Arg Glu Ser Thr Ser Gln Met His Thr Ala Ser Ser Leu Glu
            115             120             125

Lys Gln Ile Gly His Pro Ser Pro Pro Pro Glu Lys Lys Glu Leu Arg
        130             135             140

Lys Val Ala His Leu Thr Gly Lys Ser Asn Ser Arg Ser Met Pro Leu
145             150             155             160

Glu Trp Glu Asp Thr Tyr Gly Ile Val Leu Leu Ser Gly Val Lys Tyr
            165             170             175

Lys Lys Gly Gly Leu Val Ile Asn Glu Thr Gly Leu Tyr Phe Val Tyr
            180             185             190

Ser Lys Val Tyr Phe Arg Gly Gln Ser Cys Asn Asn Leu Pro Leu Ser
            195             200             205

His Lys Val Tyr Met Arg Asn Ser Lys Tyr Pro Gln Asp Leu Val Met
        210             215             220

Met Glu Gly Lys Met Met Ser Tyr Cys Thr Thr Gly Gln Met Trp Ala
```

```
225             230             235             240

Arg Ser Ser Tyr Leu Gly Ala Val Phe Asn Leu Thr Ser Ala Asp His
                245             250             255

Leu Tyr Val Asn Val Ser Glu Leu Ser Leu Val Asn Phe Glu Glu Ser
            260             265             270

Gln Thr Leu Phe Gly Leu Tyr Lys Leu
        275             280
```

```
<210> SEQ ID NO 12
<211> LENGTH: 197
<212> TYPE: PRT
<213> ORGANISM: Woodchuck hepatitis virus

<400> SEQUENCE: 12

Asn Gln Pro Leu Asp Tyr Lys Ile Cys Glu Arg Leu Thr Gly Ile Leu
1               5               10              15

Asn Tyr Val Ala Pro Phe Thr Leu Cys Gly Tyr Ala Ala Leu Met Pro
            20              25              30

Leu Tyr His Ala Ile Ala Ser Arg Met Ala Phe Ile Phe Ser Ser Leu
        35              40              45

Tyr Lys Ser Trp Leu Leu Ser Leu Tyr Glu Glu Leu Trp Pro Val Val
    50              55              60

Arg Gln Arg Gly Val Val Cys Thr Val Phe Ala Asp Ala Thr Pro Thr
65              70              75              80

Gly Trp Gly Ile Ala Thr Thr Cys Gln Leu Leu Ser Gly Thr Phe Ala
            85              90              95

Phe Pro Leu Pro Ile Ala Thr Ala Glu Leu Ile Ala Ala Cys Leu Ala
            100             105             110

Arg Cys Trp Thr Gly Ala Arg Leu Leu Gly Thr Asp Asn Ser Val Val
        115             120             125

Leu Ser Gly Lys Leu Thr Ser Phe Pro Trp Leu Leu Ala Cys Val Ala
    130             135             140

Thr Trp Ile Leu Arg Gly Thr Ser Phe Cys Tyr Val Pro Ser Ala Leu
145             150             155             160

Asn Pro Ala Asp Leu Pro Ser Arg Gly Leu Leu Pro Ala Leu Arg Pro
            165             170             175

Leu Pro Arg Leu Arg Leu Arg Pro Gln Thr Ser Arg Ile Ser Leu Trp
        180             185             190

Ala Ala Ser Pro Pro
        195
```

```
<210> SEQ ID NO 13
<211> LENGTH: 528
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tagtccaatt tgttaaagac aggatatcag tggtccaggc tctagttttg actcaacaat      60
atcaccagct gaagcctata gagtacgagc catagataaa ataaaagatt ttatttagtc     120
tccagaaaaa gggggaatg aaagacccca cctgtaggtt tggcaagcta ggatcaaggt     180
caggaacaga gaaacaggag aatatgggcc aaacaggata tctgtggtaa gcagttcctg     240
ccccgctcag ggccaagaac agttggaaca ggagaatatg gccaaacag gatatctgtg     300
```

```
gtaagcagtt cctgccccgc tcagggccaa gaacagatgg tccccagatg cggtcccgcc      360
ctcagcagtt tctagagaac catcagatgt ttccagggtg ccccaaggac ctgaaatgac      420
cctgtgcctt atttgaacta accaatcagt tcgcttctcg cttctgttcg cgcgcttctg      480
ctccccgagc tcaataaaag agcccacaac ccctcactcg gcgcgatc                   528
```

<210> SEQ ID NO 14
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgagcgagc tgattaagga gaacatgcac atgaagctgt acatggaggg caccgtggac       60
aaccatcact tcaagtgcac atccgagggc gaaggcaagc cctacgaggg cacccagacc      120
atgagaatca aggtggtcga gggcggccct ctcccccttcg ccttcgacat cctggctact     180
agcttcctct acggcagcaa gaccttcatc aaccacaccc agggcatccc cgacttcttc      240
aagcagtcct ccctgagggg cttcacatgg gagagagtca ccacatacga agacgggggc      300
gtgctgaccg ctacccagga caccagcctc caggacggct gcctcatcta caacgtcaag      360
atcagagggg tgaacttcac atccaacggc cctgtgatgc agaagaaaac actcggctgg      420
gaggccttca ccgagacgct gtaccccgct gacggcggcc tggaaggcag aaacgacatg      480
gccctgaagc tcgtgggcgg gagccatctg atcgcaaaca tcaagaccac atatagatcc      540
aagaaacccg ctaagaacct caagatgcct ggcgtctact atgtggacta cagactggaa      600
agaatcaagg aggccaacaa cgagacctac gtcgagcagc acgaggtggc agtggccaga      660
tactgcgacc tccctagcaa actggggcac aagcttaat                             699
```

<210> SEQ ID NO 15
<211> LENGTH: 84
<212> TYPE: DNA
<213> ORGANISM: Teschovirus A

<400> SEQUENCE: 15

```
ggaggctccg gcggccgcgc aaaacgtgca acgaatttca gcctgctgaa gcaggccggg       60
gacgtcgagg agaatcccgg gcca                                              84
```

<210> SEQ ID NO 16
<211> LENGTH: 843
<212> TYPE: DNA
<213> ORGANISM: Homo sapiens

<400> SEQUENCE: 16

```
atgcagcagc ctttcaacta tccttatcct cagatctatt gggtcgattc tagcgcctct       60
tctccttggg caccaccagg gactgtcttg ccatgcccga ctagcgtgcc acggagacca      120
ggccagcgtc gacctccccc acctccaccc ccccctcccc tgccaccacc acccccacca      180 cctcccttc cacccttgcc acttcctccg cttaagaaac ggggaaacca cagcactggc       240
ctctgcctgt tggtcatgtt cttcatggtg ctggttcac tggtgggact gggattgggg       300
atgttccagc tgttccactt gcagaaggag ttggcagaac tgagggaaag cactagccag      360
atgcacaccg cctcaagctt ggagaagcag atcggtcacc caagccccc cccagaaaag      420 aaggagctga ggaaggtcgc acacctcacc ggtaaatcca attcccggtc aatgcccctg      480
```

-continued

```
gagtgggaag acacctatgg catcgttctg ctttcaggcg tcaaatacaa gaaaggaggg      540
ctggttatca atgaaacagg gctgtatttc gtttattcca aggtctactt tcgggggcag      600
tcctgtaaca atctccctct cagccacaaa gtctacatga ggaacagcaa ataccccag       660 gatctggtta tgatggaagg gaagatgatg agctactgca ctaccggcca gatgtgggcc      720
aggagttcct acctgggtgc cgtcttcaac cttacttccg cagaccatct gtacgtcaac      780
gtgagtgaac tgtccctggt gaactttgag gagagtcaga cctttttcgg gctgtataaa      840
ctg                                                                     843

<210> SEQ ID NO 17
<211> LENGTH: 240
<212> TYPE: DNA
<213> ORGANISM: Homo sapiens

<400> SEQUENCE: 17
atgcagcagc ctttcaacta tccttatcct cagatctatt gggtcgattc tagcgcctct       60
tctccttggg caccaccagg gactgtcttg ccatgcccga ctagcgtgcc acggagacca      120
ggccagcgtc gacctccccc acctccaccc cccctcccc tgccaccacc accccaccacca     180 cctcccttc caccctgcc acttcctccg cttaagaaac ggggaaacca cagcactggc       240

<210> SEQ ID NO 18
<211> LENGTH: 66
<212> TYPE: DNA
<213> ORGANISM: Homo sapiens

<400> SEQUENCE: 18
ctctgcctgt tggtcatgtt cttcatggtg ctggttgcac tggtgggact gggattgggg       60
atgttc                                                                   66

<210> SEQ ID NO 19
<211> LENGTH: 537
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 19
cagctgttcc acttgcagaa ggagttggca gaactgaggg aaagcactag ccagatgcac       60
accgcctcaa gcttggagaa gcagatcggt cacccaagcc ccccccagaa aagaaggag       120 ctgaggaagg tcgcacacct caccggtaaa tccaattccc ggtcaatgcc cctggagtgg      180
gaagacacct atggcatcgt tctgctttca ggcgtcaaat acaagaaagg agggctggtt      240
atcaatgaaa cagggctgta tttcgtttat tccaaggtct actttcgggg gcagtcctgt      300
aacaatctcc ctctcagcca caaagtctac atgaggaaca gcaaataccc ccaggatctg      360
gttatgatgg aagggaagat gatgagctac tgcactaccg gccagatgtg ggccaggagt      420
tcctacctgg gtgccgtctt caaccttact tccgcagacc atctgtacgt caacgtgagt      480
gaactgtccc tggtgaactt tgaggagagt cagacctttt tcgggctgta taaactg         537

<210> SEQ ID NO 20
<211> LENGTH: 624
<212> TYPE: DNA
<213> ORGANISM: Artificial Sequence
<220> FEATURE:
<223> OTHER INFORMATION: Description of Artificial Sequence: Synthetic
     polynucleotide
```

-continued

<400> SEQUENCE: 20

```
atgggcaacc acagcaccgg cctgtgcctg ctggtgatgt tcttcatggt gctggtggcc      60
ctggtgggcc tgggcctggg catgttccag ctgttccacc tgcagaagga gctggccgag     120
ctgagagaga gcaccagcca gatgcacacc gccagcagcc tggagaagca gatcggccac     180
cccagccccc cccccgagaa gaaggagctg agaaaggtgg cccacctgac cggcaagagc     240
aacagcagaa gcatgcccct ggagtgggag gacacctacg catcgtgct gctgagcggc      300 gtgaagtaca agaagggcgg cctggtgatc aacgagaccg gcctgtactt cgtgtacagc     360
aaggtgtact tcagaggcca gagctgcaac aacctgcccc tgagccacaa ggtgtacatg     420
agaaacagca agtacccccca ggacctggtg atgatggagg gcaagatgat gagctactgc     480
accaccggcc agatgtgggc cagaagcagc tacctgggcg ccgtgttcaa cctgaccagc     540
gccgaccacc tgtacgtgaa cgtgagcgag ctgagcctgg tgaacttcga ggagagccag     600
accttcttcg gcctgtacaa gctg                                            624
```

<210> SEQ ID NO 21
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgcagcagc ctttcaacta tccttatcct cagatctatt gggtcgattc tagcgcctct      60
tctccttggg caccaccagg gactgtcttg ccatgcccga ctagcgtgcc acggagacca     120
ggccagcgtc gacctccccc acctccaccc cccctcccc tgccaccacc accccccacca     180 cctcccctc caccccttgcc acttcctccg cttaagaaac ggggaaacca cagcactggc     240
ctcgccctgt tggtcatgtt cttcatggtg ctggttgcac tggtgggact gggattgggg     300
atgttccagc tgttccactt gcagaaggag ttggcagaac tgagggaaag cactagccag     360
atgcacaccg cctcaagctt ggagaagcag atcggtcacc caagcccccc cccagaaaag     420
aaggagctga ggaaggtcgc acacctcacc ggtaaatcca attcccggtc aatgcccctg     480
gagtgggaag acacctatgg catcgttctg ctttcaggcg tcaaatacaa gaaggaggg      540 ctggttatca atgaaacagg gctgtatttc gtttattcca aggtctactt tcggggggcag     600 tcctgtaaca atctccctct cagccacaaa gtctacatga ggaacagcaa ataccccccag     660 gatctggtta tgatggaagg gaagatgatg agctactgca ctaccggcca gatgtgggcc     720
aggagttcct acctgggtgc cgtcttcaac cttacttccg cagaccatct gtacgtcaac     780
gtgagtgaac tgtccctggt gaactttgag gagagtcaga ccttttttcgg gctgtataaa     840 ctg                                                                   843
```

<210> SEQ ID NO 22
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atgcagcagc ctttcaacta tccttatcct cagatctatt gggtcgattc tagcgcctct      60
```

-continued

```
tctccttggg caccaccagg gactgtcttg ccatgcccga ctagcgtgcc acggagacca    120
ggccagcgtc gacctccccc acctccaccc cccctccccc tgccaccacc accccacca    180 cctccccttc caccccttgcc acttcctccg cttaagaaac ggggaaacca cagcactggc    240
ctctgcctgt tggtcatgtt cttcatggtg ctggttgcac tggtgggact gggattgggg    300
atgttccagc tgttccactt gcagaaggag ttggcagaac tgagggaaag cactagccag    360
atgcacaccg cctcagagga agccgctgcc atcggtcacc caagccccc cccagaaaag    420 aaggagctga ggaaggtcgc acacctcacc ggtaaatcca attcccggtc aatgcccctg    480
gagtgggaag acacctatgg catcgttctg ctttcaggcg tcaaatacaa gaaaggaggg    540
ctggttatca atgaaacagg gctgtatttc gtttattcca aggtctactt tcggggcag     600 tcctgtaaca atctccctct cagccacaaa gtctacatga ggaacagcaa ataccccag     660 gatctggtta tgatggaagg gaagatgatg agctactgca ctaccggcca gatgtgggcc    720
aggagttcct acctgggtgc cgtcttcaac cttacttccg cagaccatct gtacgtcaac    780
gtgagtgaac tgtccctggt gaactttgag gagagtcaga ccttttttcgg gctgtataaa    840 ctg                                                                   843
```

```
<210> SEQ ID NO 23
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
```

```
atgcagcagc ctttcaacta tccttatcct cagatctatt gggtcgattc tagcgcctct     60
tctccttggg caccaccagg gactgtcttg ccatgcccga ctagcgtgcc acggagacca    120
ggccagcgtc gacctccccc acctccaccc cccctccccc tgccaccacc accccacca    180 cctccccttc caccccttgcc acttcctccg cttaagaaac ggggaaacca cagcactggc    240
ctctgcctgt tggtcatgtt cttcatggtg ctggttgcac tggtgggact gggattgggg    300
atgttccagc tgttccactt gcagaaggag ttggcagaac tgagggaaag cactagccag    360
atgcacaccg cctcaagctt ggagaaggac atcggtcacc caagccccc cccagaaaag    420 aaggagctga ggaaggtcgc acacctcacc ggtaaatcca attcccggtc aatgcccctg    480
gagtgggaag acacctatgg catcgttctg ctttcaggcg tcaaatacaa gaaaggaggg    540
ctggttatca atgaaacagg gctgtatttc gtttattcca aggtctactt tcggggcag     600 tcctgtaaca atctccctct cagccacaaa gtctacatga ggaacagcaa ataccccag     660 gatctggtta tgatggaagg gaagatgatg agctactgca ctaccggcca gatgtgggcc    720
aggagttcct acctgggtgc cgtcttcaac cttacttccg cagaccatct gtacgtcaac    780
gtgagtgaac tgtccctggt gaactttgag gagagtcaga ccttttttcgg gctgtataaa    840 ctg                                                                   843
```

```
<210> SEQ ID NO 24
<211> LENGTH: 592
<212> TYPE: DNA
<213> ORGANISM: Woodchuck hepatitis virus

<400> SEQUENCE: 24
```

```
aatcaacctc tggattacaa aatttgtgaa agattgactg gtattcttaa ctatgttgct     60
```

-continued

```
ccttttacgc tatgtggata cgctgcttta atgcctttgt atcatgctat tgcttcccgt      120
atggctttca ttttctcctc cttgtataaa tcctggttgc tgtctcttta tgaggagttg      180
tggcccgttg tcaggcaacg tggcgtggtg tgcactgtgt ttgctgacgc aaccccccact    240 ggttggggca ttgccaccac ctgtcagctc ctttccggga cttttcgcttt ccccctccct    300 attgccacgg cggaactcat cgccgcctgc cttgcccgct gctggacagg ggctcggctg      360
ttgggcactg acaattccgt ggtgttgtcg gggaagctga cgtcctttcc atggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg             592
```

```
<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaggctccg gcggccgcgc aaaacgt                                          27

<210> SEQ ID NO 26
<211> LENGTH: 8425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
```

```
tggaagggct aattcactcc caaagaagac aagatatcct tgatctgtgg atctaccaca       60
cacaaggcta cttccctgat tagcagaact acacaccagg gccaggggtc agatatccac      120
tgacctttgg atggtgctac aagctagtac cagttgagcc agataaggta gaagaggcca      180
ataaaggaga gaacaccagc ttgttacacc ctgtgagcct gcatgggatg gatgacccgg      240
agagagaagt gttagagtgg aggtttgaca gccgcctagc atttcatcac gtggcccgag      300
agctgcatcc ggagtacttc aagaactgct gatatcgagc ttgctacaag ggactttccg      360
ctggggactt tccagggagg cgtggcctgg gcgggactgg ggagtggcga gccctcagat      420
cctgcatata agcagctgct ttttgcctgt actgggtctc tctggttaga ccagatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600 agacccttttt agtcagtgtg gaaaatctct agcagtggcg cccgaacagg gacttgaaag      660
cgaaagggaa accagaggag ctctctcgac gcaggactcg gcttgctgaa gcgcgcacgg      720
caagaggcga ggggcggcga ctggtgagta cgccaaaaat tttgactagc ggaggctaga      780
aggagagaga tgggtgcgag agcgtcagta ttaagcgggg gagaattaga tcgcgatggg      840
aaaaaattcg gttaaggcca gggggaaaga aaaaatataa attaaaacat atagtatggg      900
caagcaggga gctagaacga ttcgcagtta atcctggcct gttagaaaca tcagaaggct      960
gtagacaaat actgggacag ctacaaccat cccttcagac aggatcagaa gaacttagat     1020
cattatataa tacagtagca accctctatt gtgtgcatca aaggatagag ataaaagaca     1080
ccaaggaagc tttagacaag atagaggaag agcaaaacaa aagtaagacc accgcacagc     1140
```

```
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttgggggtt gctctggaaa    1560 actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag ttttttgctgt    1860 actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg ggggtacagt gcaggggaaa gaatagtaga cataatagca acagacatac    2100
aaactaaaga attacaaaaa caaattacaa aaattcaaaa ttttcgggtt tattacaggg    2160
acagcagaga tccagtttat cgattagtcc aatttgttaa agacaggata tcagtggtcc    2220
aggctctagt tttgactcaa caatatcacc agctgaagcc tatagagtac gagccataga    2280
taaaataaaa gatttttattt agtctccaga aaaggggggg aatgaaagac cccacctgta    2340
ggtttggcaa gctaggatca aggtcaggaa cagagaaaca ggagaatatg ggccaaacag    2400
gatatctgtg gtaagcagtt cctgccccgc tcagggccaa gaacagttgg aacaggagaa    2460
tatgggccaa acaggatatc tgtggtaagc agttcctgcc ccgctcaggg ccaagaacag    2520
atggtcccca gatgcggtcc cgccctcagc agtttctaga gaaccatcag atgtttccag    2580
ggtgccccaa ggacctgaaa tgaccctgtg ccttatttga actaaccaat cagttcgctt    2640
ctcgcttctg ttcgcgcgct tctgctcccc gagctcaata aaagagccca caacccctca    2700
ctcggcgcga tcggatctat ttccggtgaa ttccgccacc atgagcgagc tgattaagga    2760
gaacatgcac atgaagctgt acatggaggg caccgtggac aaccatcact tcaagtgcac    2820
atccgagggc gaaggcaagc cctacgaggg cacccagacc atgagaatca aggtggtcga    2880
gggcggccct ctccccttcg ccttcgacat cctggctact agcttcctct acggcagcaa    2940
gaccttcatc aaccacaccc agggcatccc cgacttcttc aagcagtcct ccctgaggg    3000 cttcacatgg gagagagtca ccacatacga agacgggggc gtgctgaccg ctacccagga    3060
caccagcctc caggacggct gcctcatcta caacgtcaag atcagagggg tgaacttcac    3120
atccaacggc cctgtgatgc agaagaaaac actcggctgg gaggccttca ccgagacgct    3180
gtaccccgct gacggcggcc tggaaggcag aaacgacatg gccctgaagc tcgtgggcgg    3240
gagccatctg atcgcaaaca tcaagaccac atatagatcc aagaaacccg ctaagaacct    3300
caagatgcct ggcgtctact atgtggacta cagactggaa agaatcaagg aggccaacaa    3360
cgagacctac gtcgagcagc acgaggtggc agtggccaga tactcgacc tccctagcaa    3420 actggggcac aagcttaatg gaggctccgg cggccgcgca aaacgtgcaa cgaatttcag    3480
```

-continued

```
cctgctgaag caggccgggg acgtcgagga gaatcccggg ccaatgcagc agcctttcaa    3540
ctatccttat cctcagatct attgggtcga ttctagcgcc tcttctcctt gggcaccacc    3600
agggactgtc ttgccatgcc cgactagcgt gccacggaga ccaggccagc gtcgacctcc    3660
cccacctcca cccccccctc ccctgccacc accacccca  ccacctcccc ttccacccctt    3720 gccacttcct ccgcttaaga aacggggaaa ccacagcact ggcctctgcc tgttggtcat    3780
gttcttcatg gtgctggttg cactggtggg actgggattg gggatgttcc agctgttcca    3840
cttgcagaag gagttggcag aactgaggga aagcactagc cagatgcaca ccgcctcaag    3900
cttggagaag cagatcggtc acccaagccc cccccagaa  aagaaggagc tgaggaaggt    3960
cgcacacctc accggtaaat ccaattcccg gtcaatgccc ctggagtggg aagacaccta    4020
tggcatcgtt ctgctttcag gcgtcaaata caagaaagga gggctggtta tcaatgaaac    4080
agggctgtat ttcgtttatt ccaaggtcta ctttcggggg cagtcctgta acaatctccc    4140
tctcagccac aaagtctaca tgaggaacag caaataccc  caggatctgg ttatgatgga    4200
agggaagatg atgagctact gcactaccgg ccagatgtgg gccaggagtt cctacctggg    4260
tgccgtcttc aaccttactt ccgcagacca tctgtacgtc aacgtgagtg aactgtccct    4320
ggtgaacttt gaggagagtc agacctttt  cgggctgtat aaactgtgat agggcgcgcc    4380
acgcgtctgg aacaatcaac ctctggatta caaaatttgt gaaagattga ctggtattct    4440
taactatgtt gctcctttta cgctatgtgg atacgctgct ttaatgcctt tgtatcatgc    4500
tattgcttcc cgtatggctt tcattttctc ctccttgtat aaatcctggt tgctgtctct    4560
ttatgaggag ttgtggcccg ttgtcaggca acgtggcgtg gtgtgcactg tgtttgctga    4620 cgcaacccc  actggttggg gcattgccac cacctgtcag ctcctttccg ggactttcgc    4680 tttcccctc  cctattgcca cggcggaact catcgccgcc tgccttgccc gctgctggac    4740
aggggctcgg ctgttgggca ctgacaattc cgtggtgttg tcggggaagc tgacgtcctt    4800
tccatggctg ctcgcctgtg ttgccacctg gattctgcgc gggacgtcct tctgctacgt    4860
cccttcggcc ctcaatccag cggaccttcc ttcccgcggc ctgctgccgg ctctgcggcc    4920
tcttccgcgt cttcgccttc gccctcagac gagtcggatc tccctttggg ccgcctcccc    4980
gcctggaatt aattctgcag tcgagaccta gaaaaacatg gagcaatcac aagtagcaat    5040
acagcagcta ccaatgctga ttgtgcctgg ctagaagcac aagaggagga ggaggtgggt    5100
tttccagtca cacctcaggt accttttaaga ccaatgactt acaaggcagc tgtagatctt    5160
agccactttt taaaagaaaa gaggggactg gaagggctaa ttcactccca acgaagacaa    5220
gatatccttg atctgtggat ctaccacaca caaggctact ccctgatta  gcagaactac    5280 acaccagggc cagggtcag  atatccactg accttt tggat ggtgctacaa gctagtacca    5340
gttgagccag ataaggtaga agaggccaat aaaggagaga acaccagctt gttacaccct    5400
gtgagcctgc atgggatgga tgacccgag  agagaagtgt tagagtggag gtttgacagc    5460
cgcctagcat ttcatcacgt ggcccgagag ctgcatccgg agtacttcaa gaactgctga    5520
tatcgagctt gctacaaggg actttccgct ggggactttc cagggaggcg tggcctgggc    5580
gggactgggg agtggcgagc cctcagatcc tgcatataag cagctgcttt ttgcctgtac    5640
tgggtctctc tggttagacc agatctgagc ctgggagctc tctggctaac tagggaaccc    5700
actgcttaag cctcaataaa gcttgccttg agtgcttcaa gtagtgtgtg cccgtctgtt    5760
gtgtgactct ggtaactaga gatccctcag acccttttag tcagtgtgga aaatctctag    5820
cagtagtagt tcatgtcatc ttattattca gtatttataa cttgcaaaga aatgaatatc    5880
```

```
agagagtgag aggccttgac attgctagcg tttaccgtcg acctctagct agagcttggc    5940
gtaatcatgg tcatagctgt ttcctgtgtg aaattgttat ccgctcacaa ttccacacaa    6000
catacgagcc ggaagcataa agtgtaaagc ctggggtgcc taatgagtga gctaactcac    6060
attaattgcg ttgcgctcac tgcccgcttt ccagtcggga aacctgtcgt gccagctgca    6120
ttaatgaatc ggccaacgcg cggggagagg cggtttgcgt attgggcgct cttccgcttc    6180
ctcgctcact gactcgctgc gctcggtcgt tcggctgcgg cgagcggtat cagctcactc    6240
aaaggcggta atacggttat ccacagaatc aggggataac gcaggaaaga acatgtgagc    6300
aaaaggccag caaaaggcca ggaaccgtaa aaaggccgcg ttgctggcgt ttttccatag    6360
gctccgcccc cctgacgagc atcacaaaaa tcgacgctca agtcagaggt ggcgaaaccc    6420
gacaggacta taaagatacc aggcgtttcc ccctggaagc tccctcgtgc gctcctgt      6480 tccgaccctg ccgcttaccg gatacctgtc cgcctttctc ccttcgggaa gcgtggcgct    6540
ttctcatagc tcacgctgta ggtatctcag ttcggtgtag gtcgttcgct ccaagctggg    6600
ctgtgtgcac gaaccccccg ttcagcccga ccgctgcgcc ttatccggta actatcgtct    6660
tgagtccaac ccggtaagac acgacttatc gccactggca gcagccactg gtaacaggat    6720
tagcagagcg aggtatgtag gcggtgctac agagttcttg aagtggtggc ctaactacgg    6780
ctacactaga agaacagtat ttggtatctg cgctctgctg aagccagtta ccttcggaaa    6840
aagagttggt agctcttgat ccggcaaaca aaccaccgct ggtagcggtg gtttttttgt    6900
ttgcaagcag cagattacgc gcagaaaaaa aggatctcaa gaagatcctt tgatcttttc    6960
tacggggtct gacgctcagt ggaacgaaaa ctcacgttaa gggattttgg tcatgagatt    7020
atcaaaaagg atcttcacct agatcctttt aaattaaaaa tgaagtttta aatcaatcta    7080
aagtatatat gagtaaactt ggtctgacag ttaccaatgc ttaatcagtg aggcacctat    7140
ctcagcgatc tgtctatttc gttcatccat agttgcctga ctccccgtcg tgtagataac    7200
tacgatacgg gagggcttac catctggccc cagtgctgca atgataccgc gagacccacg    7260
ctcaccggct ccagatttat cagcaataaa ccagccagcc ggaagggccg agcgcagaag    7320
tggtcctgca actttatccg cctccatcca gtctattaat tgttgccggg aagctagagt    7380
aagtagttcg ccagttaata gtttgcgcaa cgttgttgcc attgctacag gcatcgtggt    7440
gtcacgctcg tcgtttggta tggcttcatt cagctccggt tcccaacgat caaggcgagt    7500
tacatgatcc cccatgttgt gcaaaaaagc ggttagctcc ttcggtcctc cgatcgttgt    7560
cagaagtaag ttggccgcag tgttatcact catggttatg gcagcactgc ataattctct    7620
tactgtcatg ccatccgtaa gatgcttttc tgtgactggt gagtactcaa ccaagtcatt    7680
ctgagaatag tgtatgcggc gaccgagttg ctcttgcccg gcgtcaatac gggataatac    7740
cgcgccacat agcagaactt aaaagtgct catcattgga aaacgttctt cggggcgaaa      7800
actctcaagg atcttaccgc tgttgagatc cagttcgatg taacccactc gtgcacccaa    7860
ctgatcttca gcatctttta ctttcaccag cgtttctggg tgagcaaaaa caggaaggca    7920
aaatgccgca aaaaagggaa taagggcgac acgaaatgt tgaatactca tactcttcct     7980
ttttcaatat tattgaagca tttatcaggg ttattgtctc atgagcggat acatatttga    8040
atgtatttag aaaaataaac aaataggggt tccgcgcaca tttccccgaa aagtgccacc    8100
tgacgtcgac ggatcgggag atcaacttgt ttattgcagc ttataatggt tacaaataaa    8160
gcaatagcat cacaaatttc acaaataaag catttttttc actgcattct agttgtggtt    8220
```

-continued

```
tgtccaaact catcaatgta tcttatcatg tctggatcaa ctggataact caagctaacc       8280
aaaatcatcc caaacttccc accccatacc ctattaccac tgccaattac ctgtggtttc       8340
atttactcta aacctgtgat tcctctgaat tattttcatt ttaaagaaat tgtatttgtt       8400
aaatatgtac tacaaactta gtagt                                            8425

<210> SEQ ID NO 27
<211> LENGTH: 8425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tggaagggct aattcactcc caaagaagac aagatatcct tgatctgtgg atctaccaca         60
cacaaggcta cttccctgat tagcagaact acacaccagg gccaggggtc agatatccac        120
tgacctttgg atggtgctac aagctagtac cagttgagcc agataaggta gaagaggcca        180
ataaaggaga gaacaccagc ttgttacacc ctgtgagcct gcatgggatg gatgacccgg        240
agagagaagt gttagagtgg aggtttgaca gccgcctagc atttcatcac gtggcccgag        300
agctgcatcc ggagtacttc aagaactgct gatatcgagc ttgctacaag ggactttccg        360
ctggggactt tccagggagg cgtggcctgg gcgggactgg ggagtggcga ccctcagat         420 cctgcatata agcagctgct ttttgcctgt actgggtctc tctggttaga ccagatctga        480
gcctgggagc tctctggcta actagggaac ccactgctta agcctcaata agcttgcct        540 tgagtgcttc aagtagtgtg tgcccgtctg ttgtgtgact ctggtaacta gagatccctc        600 agacccttt agtcagtgtg gaaaatctct agcagtggcg cccgaacagg acttgaaag        660 cgaaagggaa accagaggag ctctctcgac gcaggactcg gcttgctgaa gcgcgcacgg        720
caagaggcga ggggcggcga ctggtgagta cgccaaaaat tttgactagc ggaggctaga        780
aggagagaga tgggtgcgag agcgtcagta ttaagcgggg gagaattaga tcgcgatggg        840
aaaaaattcg gttaaggcca gggggaaaga aaaaatataa attaaaacat atagtatggg        900
caagcaggga gctagaacga ttcgcagtta atcctggcct gttagaaaca tcagaaggct        960
gtagacaaat actgggacag ctacaaccat cccttcagac aggatcagaa gaacttagat       1020
cattatataa tacagtagca accctctatt gtgtgcatca aaggatagag ataaaagaca       1080
ccaaggaagc tttagacaag atagaggaag agcaaaacaa aagtaagacc accgcacagc       1140
aagcggccgg ccgctgatct tcagacctgg aggaggagat atgagggaca attggagaag       1200
tgaattatat aaatataaag tagtaaaaat tgaaccatta ggagtagcac ccaccaaggc       1260
aaagagaaga gtggtgcaga gagaaaaaag agcagtggga ataggagctt tgttccttgg       1320
gttcttggga gcagcaggaa gcactatggg cgcagcgtca atgacgctga cggtacaggc       1380
cagacaatta ttgtctggta tagtgcagca gcagaacaat ttgctgaggg ctattgaggc       1440
gcaacagcat ctgttgcaac tcacagtctg gggcatcaag cagctccagg caagaatcct       1500
ggctgtggaa agatacctaa aggatcaaca gctcctgggg atttggggtt gctctggaaa       1560
actcatttgc accactgctg tgccttggaa tgctagttgg agtaataaat ctctggaaca       1620
gatttggaat cacacgacct ggatggagtg ggacagagaa attaacaatt acacaagctt       1680
aatacactcc ttaattgaag aatcgcaaaa ccagcaagaa aagaatgaac aagaattatt       1740
ggaattagat aaatgggcaa gtttgtggaa ttggtttaac ataacaaatt ggctgtggta       1800
```

-continued

```
tataaaatta ttcataatga tagtaggagg cttggtaggt ttaagaatag tttttgctgt      1860
actttctata gtgaatagag ttaggcaggg atattcacca ttatcgtttc agacccacct      1920
cccaaccccg aggggacccg acaggcccga aggaatagaa gaagaaggtg gagagagaga      1980
cagagacaga tccattcgat tagtgaacgg atctcgacgg tatcgccttt aaaagaaaag      2040
gggggattgg ggggtacagt gcaggggaaa gaatagtaga cataatagca acagacatac      2100
aaactaaaga attacaaaaa caaattacaa aaattcaaaa ttttcgggtt tattacaggg      2160
acagcagaga tccagtttat cgattagtcc aatttgttaa agacaggata tcagtggtcc      2220
aggctctagt tttgactcaa caatatcacc agctgaagcc tatagagtac gagcccataga      2280 taaaataaaa gattttattt agtctccaga aaaaggggg aatgaaagac cccacctgta      2340
ggtttggcaa gctaggatca aggtcaggaa cagagaaaca ggagaatatg gccaaacag      2400 gatatctgtg gtaagcagtt cctgccccgc tcagggccaa gaacagttgg aacaggagaa      2460
tatgggccaa acaggatatc tgtggtaagc agttcctgcc ccgctcaggg ccaagaacag      2520
atggtcccca gatgcggtcc cgccctcagc agtttctaga gaaccatcag atgtttccag      2580
ggtgccccaa ggacctgaaa tgaccctgtg ccttatttga actaaccaat cagttcgctt      2640
ctcgcttctg ttcgcgcgct tctgctcccc gagctcaata aaagagccca cacccctca      2700 ctcggcgcga tcggatctat ttccggtgaa ttccgccacc atgagcgagc tgattaagga      2760
gaacatgcac atgaagctgt acatggaggg caccgtggac aaccatcact tcaagtgcac      2820
atccgagggc gaaggcaagc cctacgaggg cacccagacc atgagaatca aggtggtcga      2880
gggcggccct ctccccttcg ccttcgacat cctggctact agcttcctct acggcagcaa      2940
gaccttcatc aaccacaccc agggcatccc cgacttcttc aagcagtcct tccctgaggg      3000
cttcacatgg gagagagtca ccacatacga agacgggggc gtgctgaccg ctacccagga      3060
caccagcctc caggacggct gcctcatcta caacgtcaag atcagagggg tgaacttcac      3120
atccaacggc cctgtgatgc agaagaaaac actcggctgg gaggccttca ccgagacgct      3180
gtaccccgct gacggcggcc tggaaggcag aaacgacatg ggccctgaagc tcgtgggcgg      3240 gagccatctg atcgcaaaca tcaagaccac atatagatcc aagaaacccg ctaagaacct      3300
caagatgcct ggcgtctact atgtggacta cagactggaa agaatcaagg aggccaacaa      3360
cgagacctac gtcgagcagc acgaggtggc agtggccaga tactgcgacc tccctagcaa      3420
actggggcac aagcttaatg gaggctccgg cggccgcgca aaacgtgcaa cgaatttcag      3480
cctgctgaag caggccgggg acgtcgagga gaatcccggg ccaatgcagc agcctttcaa      3540
ctatccttat cctcagatct attgggtcga ttctagcgcc tcttctcctt gggcaccacc      3600
agggactgtc ttgccatgcc cgactagcgt gccacggaga ccaggccagc gtcgacctcc      3660
cccacctcca cccccccctc ccctgccacc accaccccca ccacctcccc ttccaccctt      3720
gccacttcct ccgcttaaga aacgggggaaa ccacagcact ggcctctgcc tgttggtcat      3780
gttcttcatg gtgctggttg cactggtggg actgggattg gggatgttcc agctgttcca      3840
cttgcagaag gagttggcag aactgaggga aagcactagc cagatgcaca ccgcctcaag      3900
cttggagaag cagatcggtc acccaagccc cccccccagaa aagaaggagc tgaggaaggt      3960
cgcacacctc accggtaaat ccaattcccg gtcaatgccc ctggagtggg aagacaccta      4020
tggcatcgtt ctgctttcag gcgtcaaata caagaaagga gggctggtta tcaatgaaac      4080
agggctgtat ttcgtttatt ccaaggtcta ctttcggggg cagtcctgta acaatctccc      4140
tctcagccac aaagtctaca tgaggaacag caaataccc caggatctgg ttatgatgga      4200
```

```
agggaagatg atgagctact gcactaccgg ccagatgtgg gccaggagtt cctacctggg   4260
tgccgtcttc aaccttactt ccgcagacca tctgtacgtc aacgtgagtg aactgtccct   4320
ggtgaacttt gaggagagtc agaccctgtt cgggctgtat aaactgtgat agggcgcgcc   4380
acgcgtctgg aacaatcaac ctctggatta caaaatttgt gaaagattga ctggtattct   4440
taactatgtt gctcctttta cgctatgtgg atacgctgct ttaatgcctt tgtatcatgc   4500
tattgcttcc cgtatggctt tcattttctc ctccttgtat aaatcctggt tgctgtctct   4560
ttatgaggag ttgtggcccg ttgtcaggca acgtggcgtg gtgtgcactg tgtttgctga   4620 cgcaacccc actggttggg gcattgccac cacctgtcag ctcctttccg ggactttcgc   4680 tttcccctc cctattgcca cggcggaact catcgccgcc tgccttgccc gctgctggac   4740
aggggctcgg ctgttgggca ctgacaattc cgtggtgttg tcggggaagc tgacgtcctt   4800
tccatggctg ctcgcctgtg ttgccacctg gattctgcgc gggacgtcct tctgctacgt   4860
cccttcggcc ctcaatccag cggaccttcc ttcccgcggc ctgctgccgg ctctgcggcc   4920
tcttccgcgt cttcgccttc gccctcagac gagtcggatc tccctttggg ccgcctcccc   4980
gcctggaatt aattctgcag tcgagaccta gaaaaacatg gagcaatcac aagtagcaat   5040
acagcagcta ccaatgctga ttgtgcctgg ctagaagcac aagaggagga ggaggtgggt   5100
tttccagtca cacctcaggt acctttaaga ccaatgactt acaaggcagc tgtagatctt   5160
agccactttt taaaagaaaa gagggactg gaagggctaa ttcactccca acgaagacaa   5220
gatatccttg atctgtggat ctaccacaca caaggctact ccctgatta gcagaactac   5280 acaccagggc caggggtcag atatccactg acctttggat ggtgctacaa gctagtacca   5340
gttgagccag ataaggtaga agaggccaat aaaggagaga acaccagctt gttacaccct   5400
gtgagcctgc atgggatgga tgacccggag agagaagtgt tagagtggag gtttgacagc   5460
cgcctagcat ttcatcacgt ggcccgagag ctgcatccgg agtacttcaa gaactgctga   5520
tatcgagctt gctacaaggg actttccgct ggggactttc cagggaggcg tggcctgggc   5580
gggactgggg agtggcgagc cctcagatcc tgcatataag cagctgcttt ttgcctgtac   5640
tgggtctctc tggttagacc agatctgagc ctgggagctc tctggctaac tagggaaccc   5700
actgcttaag cctcaataaa gcttgccttg agtgcttcaa gtagtgtgtg cccgtctgtt   5760
gtgtgactct ggtaactaga tccctcag acccttttag tcagtgtgga aaatctctag   5820
cagtagtagt tcatgtcatc ttattattca gtatttataa cttgcaaaga atgaatatc   5880 agagagtgag aggccttgac attgctagcg tttaccgtcg acctctagct agagcttggc   5940
gtaatcatgg tcatagctgt ttcctgtgtg aaattgttat ccgctcacaa ttccacacaa   6000
catacgagcc ggaagcataa agtgtaaagc ctggggtgcc taatgagtga gctaactcac   6060
attaattgcg ttgcgctcac tgcccgcttt ccagtcggga aacctgtcgt gccagctgca   6120
ttaatgaatc ggccaacgcg cggggagagg cggtttgcgt attgggcgct cttccgcttc   6180
ctcgctcact gactcgctgc gctcggtcgt tcggctgcgg cgagcggtat cagctcactc   6240
aaaggcggta atacggttat ccacagaatc aggggataac gcaggaaaga acatgtgagc   6300
aaaaggccag caaaaggcca ggaaccgtaa aaaggccgcg ttgctggcgt ttttccatag   6360
gctccgcccc cctgacgagc atcacaaaaa tcgacgctca agtcagaggt ggcgaaaccc   6420
gacaggacta taaagatacc aggcgtttcc ccctggaagc tccctcgtgc gctctcctgt   6480
tccgaccctg ccgcttaccg gatacctgtc gccttcctc ccttcgggaa gcgtggcgct   6540
```

```
ttctcatagc tcacgctgta ggtatctcag ttcggtgtag gtcgttcgct ccaagctggg      6600
ctgtgtgcac gaacccccg ttcagcccga ccgctgcgcc ttatccggta actatcgtct       6660
tgagtccaac ccggtaagac acgacttatc gccactggca gcagccactg gtaacaggat      6720
tagcagagcg aggtatgtag gcggtgctac agagttcttg aagtggtggc ctaactacgg      6780
ctacactaga agaacagtat ttggtatctg cgctctgctg aagccagtta ccttcggaaa      6840
aagagttggt agctcttgat ccggcaaaca aaccaccgct ggtagcggtg gttttttttgt     6900 ttgcaagcag cagattacgc gcagaaaaaa aggatctcaa gaagatcctt tgatctttttc     6960 tacggggtct gacgctcagt ggaacgaaaa ctcacgttaa gggattttgg tcatgagatt      7020
atcaaaaagg atcttcacct agatcctttt aaattaaaaa tgaagtttta aatcaatcta      7080
aagtatatat gagtaaactt ggtctgacag ttaccaatgc ttaatcagtg aggcacctat      7140
ctcagcgatc tgtctatttc gttcatccat agttgcctga ctccccgtcg tgtagataac      7200
tacgatacgg gagggcttac catctggccc cagtgctgca atgataccgc gagacccacg      7260
ctcaccggct ccagatttat cagcaataaa ccagccagcc ggaagggccg agcgcagaag      7320
tggtcctgca actttatccg cctccatcca gtctattaat tgttgccggg aagctagagt      7380
aagtagttcg ccagttaata gtttgcgcaa cgttgttgcc attgctacag gcatcgtggt      7440
gtcacgctcg tcgtttggta tggcttcatt cagctccggt tcccaacgat caaggcgagt      7500
tacatgatcc cccatgttgt gcaaaaaagc ggttagctcc ttcggtcctc cgatcgttgt      7560
cagaagtaag ttggccgcag tgttatcact catggttatg gcagcactgc ataattctct      7620
tactgtcatg ccatccgtaa gatgcttttc tgtgactggt gagtactcaa ccaagtcatt      7680
ctgagaatag tgtatgcggc gaccgagttg ctcttgcccg gcgtcaatac gggataatac      7740
cgcgccacat agcagaactt taaaagtgct catcattgga aaacgttctt cggggcgaaa      7800
actctcaagg atcttaccgc tgttgagatc cagttcgatg taacccactc gtgcacccaa      7860
ctgatcttca gcatctttta ctttcaccag cgtttctggg tgagcaaaaa caggaaggca      7920
aaatgccgca aaaaagggaa taagggcgac acggaaatgt tgaatactca tactcttcct      7980
ttttcaatat tattgaagca tttatcaggg ttattgtctc atgagcggat acatatttga      8040
atgtatttag aaaaataaac aaataggggt tccgcgcaca tttccccgaa aagtgccacc      8100
tgacgtcgac ggatcgggag atcaacttgt ttattgcagc ttataatggt tacaaataaa      8160
gcaatagcat cacaaatttc acaaataaag catttttttc actgcattct agttgtggtt      8220
tgtccaaact catcaatgta tcttatcatg tctggatcaa ctggataact caagctaacc      8280
aaaatcatcc caaacttccc accccatacc ctattaccac tgccaattac ctgtggtttc      8340
atttactcta aacctgtgat tcctctgaat tatttttcatt ttaaagaaat tgtatttgtt     8400
aaatatgtac tacaaactta gtagt                                            8425
```

```
<210> SEQ ID NO 28
<211> LENGTH: 8206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
tggaagggct aattcactcc caaagaagac aagatatcct tgatctgtgg atctaccaca       60
cacaaggcta cttccctgat tagcagaact acacaccagg gccaggggtc agatatccac      120
```

-continued

```
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600 agacccttttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttttgctgt   1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa tttttcgggtt tattacaggg   2160 acagcagaga tccagtttat cgattagtcc aatttgttaa agacaggata tcagtggtcc   2220
aggctctagt tttgactcaa caatatcacc agctgaagcc tatagagtac gagccataga   2280
taaaataaaa gattttatttt agtctccaga aaaagggggg aatgaaagac cccacctgta   2340
ggtttggcaa gctaggatca aggtcaggaa cagagaaaca ggagaatatg gccaaacag    2400 gatatctgtg gtaagcagtt cctgcccgc tcagggccaa gaacagttgg aacaggagaa    2460
tatgggccaa acaggatatc tgtggtaagc agttcctgcc ccgctcaggg ccaagaacag   2520
```

```
atggtcccca gatgcggtcc cgccctcagc agtttctaga gaaccatcag atgtttccag   2580
ggtgccccaa ggacctgaaa tgaccctgtg ccttatttga actaaccaat cagttcgctt   2640
ctcgcttctg ttcgcgcgct tctgctcccc gagctcaata aaagagccca caccccctca   2700
ctcggcgcga tcggatctat ttccggtgaa ttccgccacc atgagcgagc tgattaagga   2760
gaacatgcac atgaagctgt acatggaggg caccgtggac aaccatcact tcaagtgcac   2820
atccgagggc gaaggcaagc cctacgaggg cacccagacc atgagaatca aggtggtcga   2880
gggcggccct ctccccttcg ccttcgacat cctggctact agcttcctct acggcagcaa   2940
gaccttcatc aaccacaccc agggcatccc cgacttcttc aagcagtcct tccctgaggg   3000
cttcacatgg gagagagtca ccacatacga agacgggggc gtgctgaccg ctacccagga   3060
caccagcctc caggacggct gcctcatcta caacgtcaag atcagagggg tgaacttcac   3120
atccaacggc cctgtgatgc agaagaaaac actcggctgg gaggccttca ccgagacgct   3180
gtaccccgct gacggcggcc tggaaggcag aaacgacatg gccctgaagc tcgtgggcgg   3240
gagccatctg atcgcaaaca tcaagaccac atatagatcc aagaaacccg ctaagaacct   3300
caagatgcct ggcgtctact atgtggacta cagactggaa agaatcaagg aggccaacaa   3360
cgagacctac gtcgagcagc acgaggtggc agtggccaga tactgcgacc tccctagcaa   3420
actggggcac aagcttaatg gaggctccgg cggccgcgca aaacgtgcaa cgaatttcag   3480
cctgctgaag caggccgggg acgtcgagga gaatcccggg ccaatgggca accacagcac   3540
cggcctgtgc ctgctggtga tgttcttcat ggtgctggtg ccctggtgg gcctgggcct   3600 gggcatgttc cagctgttcc acctgcagaa ggagctggcc gagctgagag agagcaccag   3660
ccagatgcac accgccagca gcctggagaa gcagatcggc cacccagcc cccccccga   3720 gaagaaggag ctgagaaagg tggcccacct gaccggcaag agcaacagca gaagcatgcc   3780
cctggagtgg gaggacacct acggcatcgt gctgctgagc ggcgtgaagt acaagaaggg   3840
cggcctggtg atcaacgaga ccggcctgta cttcgtgtac agcaaggtgt acttcagagg   3900
ccagagctgc aacaacctgc ccctgagcca caaggtgtac atgagaaaca gcaagtaccc   3960
ccaggacctg gtgatgatgg agggcaagat gatgagctac tgcaccaccg gccagatgtg   4020
ggccagaagc agctacctgg gcgccgtgtt caacctgacc agcgccgacc acctgtacgt   4080
gaacgtgagc gagctgagcc tggtgaactt cgaggagagc cagaccttct tcggcctgta   4140
caagctgtga tagggcgcgc cacgcgtctg gaacaatcaa cctctggatt acaaaatttg   4200
tgaaagattg actggtattc ttaactatgt tgctcctttt acgctatgtg gatacgctgc   4260
tttaatgcct ttgtatcatg ctattgcttc ccgtatggct ttcattttct cctccttgta   4320
taaatcctgg ttgctgtctc tttatgagga gttgtggccc gttgtcaggc aacgtggcgt   4380
ggtgtgcact gtgtttgctg acgcaacccc cactggttgg ggcattgcca ccacctgtca   4440
gctcctttcc gggactttcg ctttccccct ccctattgcc acggcggaac tcatcgccgc   4500
ctgccttgcc cgctgctgga caggggctcg gctgttgggc actgacaatt ccgtggtgtt   4560
gtcggggaag ctgacgtcct ttccatggct gctcgcctgt gttgccacct ggattctgcg   4620
cgggacgtcc ttctgctacg tcccttcggc cctcaatcca gcggaccttc cttcccgcgg   4680
cctgctgccg gctctgcggc ctcttccgcg tcttcgcctt cgccctcaga cgagtcggat   4740
ctccctttgg gccgcctccc cgcctggaat taattctgca gtcgagacct agaaaaacat   4800
ggagcaatca caagtagcaa tacagcagct accaatgctg attgtgcctg gctagaagca   4860
```

```
caagaggagg aggaggtggg ttttccagtc acacctcagg tacctttaag accaatgact    4920
tacaaggcag ctgtagatct tagccacttt ttaaaagaaa agaggggact ggaagggcta    4980
attcactccc aacgaagaca agatatcctt gatctgtgga tctaccacac acaaggctac    5040
ttccctgatt agcagaacta cacaccaggg ccagggtca gatatccact gacctttgga      5100
tggtgctaca agctagtacc agttgagcca gataaggtag aagaggccaa taaaggagag    5160
aacaccagct tgttacaccc tgtgagcctg catgggatgg atgacccgga gagagaagtg    5220
ttagagtgga ggtttgacag ccgcctagca tttcatcacg tggcccgaga gctgcatccg    5280
gagtacttca agaactgctg atatcgagct tgctacaagg actttccgc tggggacttt      5340 ccagggaggc gtggcctggg cgggactggg gagtggcgag ccctcagatc ctgcatataa    5400
gcagctgctt tttgcctgta ctgggtctct ctggttagac cagatctgag cctgggagct    5460
ctctggctaa ctagggaacc cactgcttaa gcctcaataa agcttgcctt gagtgcttca    5520
agtagtgtgt gcccgtctgt tgtgtgactc tggtaactag agatccctca gacccttta     5580 gtcagtgtgg aaaatctcta gcagtagtag ttcatgtcat cttattattc agtatttata    5640
acttgcaaag aaatgaatat cagagagtga gaggccttga cattgctagc gtttaccgtc    5700
gacctctagc tagagcttgg cgtaatcatg gtcatagctg tttcctgtgt gaaattgtta    5760
tccgctcaca attccacaca acatacgagc cggaagcata aagtgtaaag cctggggtgc    5820
ctaatgagtg agctaactca cattaattgc gttgcgctca ctgcccgctt tccagtcggg    5880
aaacctgtcg tgccagctgc attaatgaat cggccaacgc gcggggagag cggtttgcg      5940 tattgggcgc tcttccgctt cctcgctcac tgactcgctg cgctcggtcg ttcggctgcg    6000
gcgagcggta tcagctcact caaaggcggt aatacggtta tccacagaat cagggggataa    6060 cgcaggaaag aacatgtgag caaaaggcca gcaaaaggcc aggaaccgta aaaaggccgc    6120
gttgctggcg tttttccata ggctccgccc ccctgacgag catcacaaaa atcgacgctc    6180
aagtcagagg tggcgaaacc cgacaggact ataaagatac caggcgtttc ccctggaag      6240 ctccctcgtg cgctctcctg ttccgaccct gccgcttacc ggatacctgt ccgcctttct    6300
cccttcggga agcgtggcgc tttctcatag ctcacgctgt aggtatctca gttcggtgta    6360
ggtcgttcgc tccaagctgg gctgtgtgca cgaaccccc gttcagcccg accgctgcgc     6420
cttatccggt aactatcgtc ttgagtccaa cccggtaaga cacgacttat cgccactggc    6480
agcagccact ggtaacagga ttagcagagc gaggtatgta ggcggtgcta cagagttctt    6540
gaagtggtgg cctaactacg gctacactag aagaacagta tttggtatct gcgctctgct    6600
gaagccagtt accttcggaa aaagagttgg tagctcttga tccggcaaac aaaccaccgc    6660
tggtagcggt ggtttttttg tttgcaagca gcagattacg cgcagaaaaa aaggatctca    6720
agaagatcct ttgatctttt ctacggggtc tgacgctcag tggaacgaaa actcacgtta    6780 agggatttt gtcatgagat tatcaaaaag gatcttcacc tagatccttt taaattaaaa     6840
atgaagtttt aaatcaatct aaagtatata tgagtaaact tggtctgaca gttaccaatg    6900
cttaatcagt gaggcaccta tctcagcgat ctgtctattt cgttcatcca tagttgcctg    6960 actcccgtc gtgtagataa ctacgatacg ggagggctta ccatctggcc ccagtgctgc      7020
aatgataccg cgagacccac gctcaccggc tccagattta tcagcaataa accagccagc    7080
cggaagggcc gagcgcagaa gtggtcctgc aactttatcc gcctccatcc agtctattaa    7140
ttgttgccgg gaagctagag taagtagttc gccagttaat agtttgcgca acgttgttgc    7200
cattgctaca ggcatcgtgg tgtcacgctc gtcgtttggt atggcttcat tcagctccgg    7260
```

```
ttcccaacga tcaaggcgag ttacatgatc ccccatgttg tgcaaaaaag cggttagctc     7320
cttcggtcct ccgatcgttg tcagaagtaa gttggccgca gtgttatcac tcatggttat     7380
ggcagcactg cataattctc ttactgtcat gccatccgta agatgctttt ctgtgactgg     7440
tgagtactca accaagtcat tctgagaata gtgtatgcgg cgaccgagtt gctcttgccc     7500
ggcgtcaata cgggataata ccgcgccaca tagcagaact ttaaaagtgc tcatcattgg     7560
aaaacgttct cgggggcgaa aactctcaag gatcttaccg ctgttgagat ccagttcgat     7620
gtaacccact cgtgcaccca actgatcttc agcatctttt actttcacca gcgtttctgg     7680
gtgagcaaaa acaggaaggc aaaatgccgc aaaaaaggga ataagggcga cacggaaatg     7740
ttgaatactc atactcttcc tttttcaata ttattgaagc atttatcagg gttattgtct     7800
catgagcgga tacatatttg aatgtattta gaaaaataaa caaatagggg ttccgcgcac     7860
atttccccga aaagtgccac ctgacgtcga cggatcggga gatcaacttg tttattgcag     7920
cttataatgg ttacaaataa agcaatagca tcacaaattt cacaaataaa gcattttttt     7980
cactgcattc tagttgtggt ttgtccaaac tcatcaatgt atcttatcat gtctggatca     8040
actggataac tcaagctaac caaaatcatc ccaaacttcc cacccatac cctattacca     8100 ctgccaatta cctgtggttt catttactct aaacctgtga ttcctctgaa ttattttcat     8160
tttaaagaaa ttgtatttgt taaatatgta ctacaaactt agtagt                   8206
```

<210> SEQ ID NO 29
<211> LENGTH: 8425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
tggaagggct aattcactcc caaagaagac aagatatcct tgatctgtgg atctaccaca       60
cacaaggcta cttccctgat tagcagaact acacaccagg gccaggggtc agatatccac      120
tgacctttgg atggtgctac aagctagtac cagttgagcc agataaggta gaagaggcca      180
ataaaggaga gaacaccagc ttgttacacc ctgtgagcct gcatgggatg gatgacccgg      240
agagagaagt gttagagtgg aggtttgaca gccgcctagc atttcatcac gtggcccgag      300
agctgcatcc ggagtacttc aagaactgct gatatcgagc ttgctacaag ggactttccg      360
ctggggactt tccagggagg cgtggcctgg gcgggactgg ggagtggcga gccctcagat      420
cctgcatata agcagctgct ttttgcctgt actgggtctc tctggttaga ccagatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600
agaccctttt agtcagtgtg aaaatctct agcagtggcg cccgaacagg acttgaaag       660 cgaaagggaa accagaggag ctctctcgac gcaggactcg gcttgctgaa gcgcgcacgg      720
caagaggcga ggggcggcga ctggtgagta cgccaaaaat tttgactagc ggaggctaga      780
aggagagaga tgggtgcgag agcgtcagta ttaagcgggg gagaattaga tcgcgatggg      840
aaaaaattcg gttaaggcca gggggaaaga aaaaatataa attaaaacat atagtatggg      900
caagcaggga gctagaacga ttcgcagtta atcctggcct gttagaaaca tcagaaggct      960
gtagacaaat actgggacag ctacaaccat cccttcagac aggatcagaa gaacttagat     1020
cattatataa tacagtagca accctctatt gtgtgcatca aaggatagag ataaaagaca     1080
```

-continued

```
ccaaggaagc tttagacaag atagaggaag agcaaaacaa aagtaagacc accgcacagc      1140
aagcggccgg ccgctgatct tcagacctgg aggaggagat atgagggaca attggagaag      1200
tgaattatat aaatataaag tagtaaaaat tgaaccatta ggagtagcac ccaccaaggc      1260
aaagagaaga gtggtgcaga gagaaaaaag agcagtggga ataggagctt tgttccttgg      1320
gttcttggga gcagcaggaa gcactatggg cgcagcgtca atgacgctga cggtacaggc      1380
cagacaatta ttgtctggta tagtgcagca gcagaacaat ttgctgaggg ctattgaggc      1440
gcaacagcat ctgttgcaac tcacagtctg gggcatcaag cagctccagg caagaatcct      1500
ggctgtggaa agatacctaa aggatcaaca gctcctgggg atttgggggt gctctggaaa      1560
actcatttgc accactgctg tgccttggaa tgctagttgg agtaataaat ctctggaaca      1620
gatttggaat cacacgacct ggatggagtg ggacagagaa attaacaatt acacaagctt      1680
aatacactcc ttaattgaag aatcgcaaaa ccagcaagaa aagaatgaac aagaattatt      1740
ggaattagat aaatgggcaa gtttgtggaa ttggtttaac ataacaaatt ggctgtggta      1800
tataaaatta ttcataatga tagtaggagg cttggtaggt ttaagaatag ttttttgctgt      1860 actttctata gtgaatagag ttaggcaggg atattcacca ttatcgtttc agacccacct      1920
cccaaccccg aggggacccg acaggcccga aggaatagaa gaagaaggtg gagagagaga      1980
cagagacaga tccattcgat tagtgaacgg atctcgacgg tatcgccttt aaaagaaaag      2040
gggggattgg ggggtacagt gcaggggaaa gaatagtaga cataatagca acagacatac      2100
aaactaaaga attacaaaaa caaattacaa aaattcaaaa ttttcgggtt tattacaggg      2160
acagcagaga tccagtttat cgattagtcc aatttgttaa agacaggata tcagtggtcc      2220
aggctctagt tttgactcaa caatatcacc agctgaagcc tatagagtac gagccataga      2280
taaaataaaa gattttattt agtctccaga aaaaggggggg aatgaaagac cccacctgta      2340
ggtttggcaa gctaggatca aggtcaggaa cagagaaaca ggagaatatg ggccaaacag      2400
gatatctgtg gtaagcagtt cctgccccgc tcagggccaa gaacagttgg aacaggagaa      2460
tatgggccaa acaggatatc tgtggtaagc agttcctgcc ccgctcaggg ccaagaacag      2520
atggtcccca gatgcggtcc cgccctcagc agttctaga gaaccatcag atgtttccag       2580
ggtgccccaa ggacctgaaa tgaccctgtg ccttatttga actaaccaat cagttcgctt      2640
ctcgcttctg ttcgcgcgct tctgctcccc gagctcaata aaagagccca caacccctca      2700
ctcggcgcga tcggatctat ttccggtgaa ttccgccacc atgagcgagc tgattaagga      2760
gaacatgcac atgaagctgt acatggaggg caccgtggac aaccatcact tcaagtgcac      2820
atccgagggc gaaggcaagc cctacgaggg cacccagacc atgagaatca aggtggtcga      2880
gggcggccct ctccccttcg ccttcgacat cctggctact agcttcctct acggcagcaa      2940
gaccttcatc aaccacaccc agggcatccc cgacttcttc aagcagtcct tccctgaggg      3000
cttcacatgg gagagagtca ccacatacga agacgggggc gtgctgaccg ctacccagga      3060
caccagcctc caggacggct gcctcatcta caacgtcaag atcagagggg tgaacttcac      3120
atccaacggc cctgtgatgc agaagaaaac actcggctgg gaggccttca ccgagacgct      3180
gtaccccgct gacggcggcc tggaaggcag aaacgacatg ccctgaagc tcgtgggcgg       3240 gagccatctg atcgcaaaca tcaagaccac atatagatcc aagaaacccg ctaagaacct      3300
caagatgcct ggcgtctact atgtggacta cagactggaa agaatcaagg aggccaacaa      3360
cgagacctac gtcgagcagc acgaggtggc agtggccaga tactgcgacc tccctagcaa      3420
```

-continued

```
actggggcac aagcttaatg gaggctccgg cggccgcgca aaacgtgcaa cgaatttcag    3480
cctgctgaag caggccgggg acgtcgagga gaatcccggg ccaatgcagc agcctttcaa    3540
ctatccttat cctcagatct attgggtcga ttctagcgcc tcttctcctt gggcaccacc    3600
agggactgtc ttgccatgcc cgactagcgt gccacggaga ccaggccagc gtcgacctcc    3660
cccacctcca ccccccctc ccctgccacc accacccca ccacctcccc ttccacccctt    3720 gccacttcct ccgcttaaga aacggggaaa ccacagcact ggcctctgcc tgttggtcat    3780
gttcttcatg gtgctggttg cactggtggg actgggattg gggatgttcc agctgttcca    3840
cttgcagaag gagttggcag aactgaggga aagcactagc cagatgcaca ccgcctcaag    3900
cttggagaag gacatcggtc acccaagccc ccccccagaa aagaaggagc tgaggaaggt    3960
cgcacacctc accggtaaat ccaattcccg gtcaatgccc ctggagtggg aagacaccta    4020
tggcatcgtt ctgctttcag gcgtcaaata caagaaagga gggctggtta tcaatgaaac    4080
agggctgtat ttcgtttatt ccaaggtcta ctttcggggg cagtcctgta acaatctccc    4140
tctcagccac aaagtctaca tgaggaacag caaatacccc caggatctgg ttatgatgga    4200
agggaagatg atgagctact gcactaccgg ccagatgtgg gccaggagtt cctacctggg    4260
tgccgtcttc aaccttactt ccgcagacca tctgtacgtc aacgtgagtg aactgtccct    4320
ggtgaacttt gaggagagtc agacctttt cgggctgtat aaactgtgat agggcgcgcc    4380
acgcgtctgg aacaatcaac ctctggatta caaaatttgt gaaagattga ctggtattct    4440
taactatgtt gctcctttta cgctatgtgg atacgctgct ttaatgcctt tgtatcatgc    4500
tattgcttcc cgtatggctt tcattttctc ctccttgtat aaatcctggt tgctgtctct    4560
ttatgaggag ttgtggcccg ttgtcaggca acgtggcgtg gtgtgcactg tgtttgctga    4620 cgcaacccccc actggttggg gcattgccac cacctgtcag ctcctttccg ggactttcgc    4680 tttcccccctc cctattgcca cggcggaact catcgccgcc tgccttgccc gctgctggac    4740
aggggctcgg ctgttgggca ctgacaattc cgtggtgttg tcggggaagc tgacgtcctt    4800
tccatggctg ctcgcctgtg ttgccacctg gattctgcgc gggacgtcct tctgctacgt    4860
cccttcggcc ctcaatccag cggaccttcc ttcccgcggc ctgctgccgg ctctgcggcc    4920
tcttccgcgt cttcgccttc gccctcagac gagtcggatc tccctttggg ccgcctcccc    4980
gcctggaatt aattctgcag tcgagaccta gaaaaacatg gagcaatcac aagtagcaat    5040
acagcagcta ccaatgctga ttgtgcctgg ctagaagcac aagaggagga ggaggtgggt    5100
tttccagtca cacctcaggt acctttaaga ccaatgactt acaaggcagc tgtagatctt    5160
agccactttt taaaagaaaa gagggggactg gaagggctaa ttcactccca acgaagacaa    5220
gatatccttg atctgtggat ctaccacaca caaggctact ccctgatta gcagaactac    5280 acaccagggc caggggtcag atatccactg acctttggat ggtgctacaa gctagtacca    5340
gttgagccag ataaggtaga agaggccaat aaaggagaga acaccagctt gttacaccct    5400
gtgagcctgc atgggatgga tgacccggag agagaagtgt tagagtggag gtttgacagc    5460
cgcctagcat ttcatcacgt ggcccgagag ctgcatccgg agtacttcaa gaactgctga    5520
tatcgagctt gctacaaggg actttccgct ggggactttc cagggaggcg tggcctgggc    5580
gggactgggg agtggcgagc cctcagatcc tgcatataag cagctgcttt ttgcctgtac    5640
tgggtctctc tggttagacc agatctgagc ctgggagctc tctggctaac tagggaaccc    5700
actgcttaag cctcaataaa gcttgccttg agtgcttcaa gtagtgtgtg cccgtctgtt    5760
gtgtgactct ggtaactaga gatccctcag acccttttag tcagtgtgga aaatctctag    5820
```

```
cagtagtagt tcatgtcatc ttattattca gtatttataa cttgcaaaga aatgaatatc    5880
agagagtgag aggccttgac attgctagcg tttaccgtcg acctctagct agagcttggc    5940
gtaatcatgg tcatagctgt ttcctgtgtg aaattgttat ccgctcacaa ttccacacaa    6000
catacgagcc ggaagcataa agtgtaaagc ctggggtgcc taatgagtga gctaactcac    6060
attaattgcg ttgcgctcac tgcccgcttt ccagtcggga aacctgtcgt gccagctgca    6120
ttaatgaatc ggccaacgcg cggggagagg cggtttgcgt attgggcgct cttccgcttc    6180
ctcgctcact gactcgctgc gctcggtcgt tcggctgcgg cgagcggtat cagctcactc    6240
aaaggcggta atacggttat ccacagaatc aggggataac gcaggaaaga acatgtgagc    6300
aaaaggccag caaaaggcca ggaaccgtaa aaaggccgcg ttgctggcgt ttttccatag    6360
gctccgcccc cctgacgagc atcacaaaaa tcgacgctca agtcagaggt ggcgaaaccc    6420
gacaggacta taaagatacc aggcgtttcc ccctggaagc tccctcgtgc gctctcctgt    6480
tccgaccctg ccgcttaccg gatacctgtc cgcctttctc ccttcgggaa gcgtggcgct    6540
ttctcatagc tcacgctgta ggtatctcag ttcggtgtag gtcgttcgct ccaagctggg    6600
ctgtgtgcac gaaccccccg ttcagcccga ccgctgcgcc ttatccggta actatcgtct    6660
tgagtccaac ccggtaagac acgacttatc gccactggca gcagccactg gtaacaggat    6720
tagcagagcg aggtatgtag gcggtgctac agagttcttg aagtggtggc ctaactacgg    6780
ctacactaga agaacagtat ttggtatctg cgctctgctg aagccagtta ccttcggaaa    6840
aagagttggt agctcttgat ccggcaaaca aaccaccgct ggtagcggtg gtttttttgt    6900
ttgcaagcag cagattacgc gcagaaaaaa aggatctcaa gaagatcctt tgatcttttc    6960
tacggggtct gacgctcagt ggaacgaaaa ctcacgttaa gggattttgg tcatgagatt    7020
atcaaaaagg atcttcacct agatcctttt aaattaaaaa tgaagtttta aatcaatcta    7080
aagtatatat gagtaaactt ggtctgacag ttaccaatgc ttaatcagtg aggcacctat    7140
ctcagcgatc tgtctatttc gttcatccat agttgcctga ctccccgtcg tgtagataac    7200
tacgatacgg gagggcttac catctggccc cagtgctgca atgataccgc gagacccacg    7260
ctcaccggct ccagatttat cagcaataaa ccagccagcc ggaagggccg agcgcagaag    7320
tggtcctgca actttatccg cctccatcca gtctattaat tgttgccggg aagctagagt    7380
aagtagttcg ccagttaata gtttgcgcaa cgttgttgcc attgctacag gcatcgtggt    7440
gtcacgctcg tcgtttggta tggcttcatt cagctccggt tcccaacgat caaggcgagt    7500
tacatgatcc cccatgttgt gcaaaaaagc ggttagctcc ttcggtcctc cgatcgttgt    7560
cagaagtaag ttggccgcag tgttatcact catggttatg gcagcactgc ataattctct    7620
tactgtcatg ccatccgtaa gatgcttttc tgtgactggt gagtactcaa ccaagtcatt    7680
ctgagaatag tgtatgcggc gaccgagttg ctcttgcccg gcgtcaatac gggataatac    7740
cgcgccacat agcagaactt taaaagtgct catcattgga aaacgttctt cggggcgaaa    7800
actctcaagg atcttaccgc tgttgagatc cagttcgatg taacccactc gtgcacccaa    7860
ctgatcttca gcatctttta ctttcaccag cgtttctggg tgagcaaaaa caggaaggca    7920
aaatgccgca aaaaagggaa taaggcgac acgaaatgt tgaatactca tactcttcct    7980
ttttcaatat tattgaagca tttatcaggg ttattgtctc atgagcggat acatatttga    8040
atgtatttag aaaaataaac aaataggggg tccgcgcaca tttccccgaa aagtgccacc    8100
tgacgtcgac ggatcgggag atcaacttgt ttattgcagc ttataatggt tacaaataaa    8160
```

```
gcaatagcat cacaaatttc acaaataaag cattttttc actgcattct agttgtggtt    8220
tgtccaaact catcaatgta tcttatcatg tctggatcaa ctggataact caagctaacc    8280
aaaatcatcc caaacttccc accccatacc ctattaccac tgccaattac ctgtggtttc    8340
atttactcta aacctgtgat tcctctgaat tattttcatt ttaaagaaat tgtatttgtt    8400
aaatatgtac tacaaactta gtagt                                          8425
```

<210> SEQ ID NO 30
<211> LENGTH: 8425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
tggaagggct aattcactcc caaagaagac aagatatcct tgatctgtgg atctaccaca      60
cacaaggcta cttccctgat tagcagaact acacaccagg gccagggtc agatatccac      120 tgacctttgg atggtgctac aagctagtac cagttgagcc agataaggta gaagaggcca      180
ataaaggaga gaacaccagc ttgttacacc ctgtgagcct gcatgggatg gatgacccgg      240
agagagaagt gttagagtgg aggtttgaca gccgcctagc atttcatcac gtggcccgag      300
agctgcatcc ggagtacttc aagaactgct gatatcgagc ttgctacaag ggactttccg      360
ctggggactt ccagggagg cgtggcctgg gcgggactgg ggagtggcga gccctcagat      420
cctgcatata agcagctgct ttttgcctgt actgggtctc tctggttaga ccagatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600 agacccttt agtcagtgtg aaaatctct agcagtggcg cccgaacagg gacttgaaag      660
cgaaagggaa accagaggag ctctctcgac gcaggactcg gcttgctgaa gcgcgcacgg      720
caagaggcga ggggcggcga ctggtgagta cgccaaaaat tttgactagc ggaggctaga      780
aggagagaga tgggtgcgag agcgtcagta ttaagcgggg gagaattaga tcgcgatggg      840
aaaaaattcg gttaaggcca ggggaaaga aaaaatataa attaaaacat atagtatggg      900
caagcaggga gctagaacga ttcgcagtta atcctggcct gttagaaaca tcagaaggct      960
gtagacaaat actgggacag ctacaaccat cccttcagac aggatcagaa gaacttagat      1020
cattatataa tacagtagca accctctatt gtgtgcatca aggatagag ataaaagaca      1080 ccaaggaagc tttagacaag atagaggaag agcaaaacaa aagtaagacc accgcacagc      1140
aagcggccgg ccgctgatct tcagacctgg aggaggagat atgagggaca attggagaag      1200
tgaattatat aaatataaag tagtaaaaat tgaaccatta ggagtagcac ccaccaaggc      1260
aaagagaaga gtggtgcaga gagaaaaaag agcagtggga ataggagctt tgttccttgg      1320
gttcttggga gcagcaggaa gcactatggg cgcagcgtca atgacgctga cggtacaggc      1380
cagacaatta ttgtctggta tagtgcagca gcagaacaat ttgctgaggg ctattgaggc      1440
gcaacagcat ctgttgcaac tcacagtctg gggcatcaag cagctccagg caagaatcct      1500
ggctgtggaa agatacctaa aggatcaaca gctcctgggg atttggggtt gctctggaaa      1560
actcatttgc accactgctg tgccttggaa tgctagttgg agtaataaat ctctggaaca      1620
gatttggaat cacacgacct ggatggagtg ggacagagaa attaacaatt acacaagctt      1680
aatacactcc ttaattgaag aatcgcaaaa ccagcaagaa aagaatgaac aagaattatt      1740
```

-continued

```
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgattagtcc aatttgttaa agacaggata tcagtggtcc   2220
aggctctagt tttgactcaa caatatcacc agctgaagcc tatagagtac gagccataga   2280
taaaataaaa gattttattt agtctccaga aaaaggggg aatgaaagac cccacctgta    2340
ggtttggcaa gctaggatca aggtcaggaa cagagaaaca ggagaatatg ggccaaacag   2400
gatatctgtg gtaagcagtt cctgccccgc tcagggccaa gaacagttgg aacaggagaa   2460
tatgggccaa acaggatatc tgtggtaagc agttcctgcc ccgctcaggg ccaagaacag   2520
atggtcccca gatgcggtcc cgccctcagc agtttctaga gaaccatcag atgtttccag   2580 ggtgcccaa ggacctgaaa tgaccctgtg ccttatttga actaaccaat cagttcgctt    2640
ctcgcttctg ttcgcgcgct tctgctcccc gagctcaata aaagagccca caacccctca   2700
ctcggcgcga tcggatctat ttccggtgaa ttccgccacc atgagcgagc tgattaagga   2760
gaacatgcac atgaagctgt acatggaggg caccgtggac aaccatcact tcaagtgcac   2820
atccgagggc gaaggcaagc cctacgaggg cacccagacc atgagaatca aggtggtcga   2880
gggcggccct ctccccttcg ccttcgacat cctggctact agcttcctct acggcagcaa   2940
gaccttcatc aaccacaccc agggcatccc cgacttcttc aagcagtcct ccctgaggg    3000 cttcacatgg gagagagtca ccacatacga agacggggc gtgctgaccg ctacccagga    3060
caccagcctc caggacggct gcctcatcta caacgtcaag atcagagggg tgaacttcac   3120
atccaacggc cctgtgatgc agaagaaaac actcggctgg gaggccttca ccgagacgct   3180
gtaccccgct gacggcggcc tggaaggcag aaacgacatg gccctgaagc tcgtgggcgg   3240
gagccatctg atcgcaaaca tcaagaccac atatagatcc aagaaacccg ctaagaacct   3300
caagatgcct ggcgtctact atgtggacta cagactggaa agaatcaagg aggccaacaa   3360
cgagacctac gtcgagcagc acgaggtggc agtggccaga tactgcgacc tccctagcaa   3420
actggggcac aagcttaatg gaggctccgg cggccgcgca aaacgtgcaa cgaatttcag   3480
cctgctgaag caggccgggg acgtcgagga gaatcccggg ccaatgcagc agcctttcaa   3540
ctatccttat cctcagatct attgggtcga ttctagcgcc tcttctcctt gggcaccacc   3600
agggactgtc ttgccatgcc cgactagcgt gccacggaga ccaggccagc gtcgacctcc   3660
cccacctcca ccccccctc ccctgccacc accaccccca ccacctcccc ttccaccctt    3720
gccacttcct ccgcttaaga aacggggaaa ccacagcact ggcctcgccc tgttggtcat   3780
gttcttcatg gtgctggttg cactggtggg actgggattg gggatgttcc agctgttcca   3840
cttgcagaag gagttggcag aactgagga agcactagc cagatgcaca ccgcctcaag     3900
cttggagaag cagatcggtc acccaagccc ccccccagaa aagaaggagc tgaggaaggt   3960
cgcacacctc accggtaaat ccaattcccg gtcaatgccc ctggagtggg aagacaccta   4020
tggcatcgtt ctgctttcag gcgtcaaata caagaaagga gggctggtta tcaatgaaac   4080
agggctgtat ttcgtttatt ccaaggtcta ctttcggggg cagtcctgta caatctccc    4140
```

-continued

```
tctcagccac aaagtctaca tgaggaacag caaatacccc caggatctgg ttatgatgga    4200
agggaagatg atgagctact gcactaccgg ccagatgtgg gccaggagtt cctacctggg    4260
tgccgtcttc aaccttactt ccgcagacca tctgtacgtc aacgtgagtg aactgtccct    4320
ggtgaacttt gaggagagtc agaccttttt cgggctgtat aaactgtgat agggcgcgcc    4380
acgcgtctgg aacaatcaac ctctggatta caaaatttgt gaaagattga ctggtattct    4440
taactatgtt gctccttta cgctatgtgg atacgctgct ttaatgcctt tgtatcatgc      4500
tattgcttcc cgtatggctt tcattttctc ctccttgtat aaatcctggt tgctgtctct    4560
ttatgaggag ttgtggcccg ttgtcaggca acgtggcgtg gtgtgcactg tgtttgctga    4620
cgcaaccccc actggttggg gcattgccac cacctgtcag ctcctttccg ggactttcgc    4680 tttcccctc cctattgcca cggcggaact catcgccgcc tgccttgccc gctgctggac       4740
aggggctcgg ctgttgggca ctgacaattc cgtggtgttg tcggggaagc tgacgtcctt    4800
tccatggctg ctcgcctgtg ttgccacctg gattctgcgc gggacgtcct tctgctacgt    4860
cccttcggcc ctcaatccag cggaccttcc ttcccgcggc ctgctgccgg ctctgcggcc     4920
tcttccgcgt cttcgccttc gccctcagac gagtcggatc tccctttggg ccgcctcccc    4980
gcctggaatt aattctgcag tcgagaccta gaaaaacatg gagcaatcac aagtagcaat    5040
acagcagcta ccaatgctga ttgtgcctgg ctagaagcac aagaggagga ggaggtgggt     5100
tttccagtca cacctcaggt acctttaaga ccaatgactt acaaggcagc tgtagatctt    5160
agccactttt taaaagaaaa gaggggactg gaagggctaa ttcactccca acgaagacaa    5220
gatatccttg atctgtggat ctaccacaca caaggctact ccctgatta gcagaactac      5280 acaccagggc caggggtcag atatccactg acctttggat ggtgctacaa gctagtacca    5340
gttgagccag ataaggtaga agaggccaat aaaggagaga acaccagctt gttacaccct    5400
gtgagcctgc atgggatgga tgacccggag agagaagtgt tagagtggag gtttgacagc    5460
cgcctagcat ttcatcacgt ggcccgagag ctgcatccgg agtacttcaa gaactgctga    5520
tatcgagctt gctacaaggg actttccgct ggggactttc cagggaggcg tggcctgggc    5580
gggactgggg agtggcgagc cctcagatcc tgcatataag cagctgcttt ttgcctgtac    5640
tgggtctctc tggttagacc agatctgagc ctgggagctc tctggctaac tagggaaccc    5700
actgcttaag cctcaataaa gcttgccttg agtgcttcaa gtagtgtgtg cccgtctgtt    5760
gtgtgactct ggtaactaga tccctcag acccttttag tcagtgtgga aaatctctag      5820
cagtagtagt tcatgtcatc ttattattca gtatttataa cttgcaaaga atgaatatc      5880 agagagtgag aggccttgac attgctagcg tttaccgtcg acctctagct agagcttggc    5940
gtaatcatgg tcatagctgt ttcctgtgtg aaattgttat ccgctcacaa ttccacacaa    6000
catacgagcc ggaagcataa agtgtaaagc ctggggtgcc taatgagtga gctaactcac    6060
attaattgcg ttgcgctcac tgcccgcttt ccagtcggga aacctgtcgt gccagctgca    6120
ttaatgaatc ggccaacgcg cggggagagg cggtttgcgt attgggcgct cttccgcttc    6180
ctcgctcact gactcgctgc gctcggtcgt tcggctgcgg cgagcggtat cagctcactc    6240
aaaggcggta atacggttat ccacagaatc aggggataac gcaggaaaga acatgtgagc    6300
aaaaggccag caaaaggcca ggaaccgtaa aaaggccgcg ttgctggcgt ttttccatag    6360
gctccgcccc cctgacgagc atcacaaaaa tcgacgctca agtcagaggt ggcgaaaccc    6420
gacaggacta taaagatacc aggcgtttcc ccctggaagc tccctcgtgc gctctcctgt    6480
```

-continued

```
tccgaccctg ccgcttaccg gataccgtc cgcctttctc ccttcgggaa gcgtggcgct      6540
ttctcatagc tcacgctgta ggtatctcag ttcggtgtag gtcgttcgct ccaagctggg      6600
ctgtgtgcac gaacccccg ttcagcccga ccgctgcgcc ttatccggta actatcgtct      6660
tgagtccaac ccggtaagac acgacttatc gccactggca gcagccactg gtaacaggat      6720
tagcagagcg aggtatgtag gcggtgctac agagttcttg aagtggtggc ctaactacgg      6780
ctacactaga agaacagtat ttggtatctg cgctctgctg aagccagtta ccttcggaaa      6840
aagagttggt agctcttgat ccggcaaaca aaccaccgct ggtagcggtg gtttttttgt      6900
ttgcaagcag cagattacgc gcagaaaaaa aggatctcaa gaagatcctt tgatctttc       6960 tacggggtct gacgctcagt ggaacgaaaa ctcacgttaa gggattttgg tcatgagatt      7020
atcaaaaagg atcttcacct agatcctttt aaattaaaaa tgaagtttta aatcaatcta      7080
aagtatatat gagtaaactt ggtctgacag ttaccaatgc ttaatcagtg aggcacctat      7140
ctcagcgatc tgtctatttc gttcatccat agttgcctga ctccccgtcg tgtagataac      7200
tacgatacgg gagggcttac catctggccc cagtgctgca atgataccgc gagacccacg      7260
ctcaccggct ccagatttat cagcaataaa ccagccagcc ggaagggccg agcgcagaag      7320
tggtcctgca actttatccg cctccatcca gtctattaat tgttgccggg aagctagagt      7380
aagtagttcg ccagttaata gtttgcgcaa cgttgttgcc attgctacag gcatcgtggt      7440
gtcacgctcg tcgtttggta tggcttcatt cagctccggt tcccaacgat caaggcgagt      7500
tacatgatcc cccatgttgt gcaaaaaagc ggttagctcc ttcggtcctc cgatcgttgt      7560
cagaagtaag ttggccgcag tgttatcact catggttatg gcagcactgc ataattctct      7620
tactgtcatg ccatccgtaa gatgctttc tgtgactggt gagtactcaa ccaagtcatt      7680
ctgagaatag tgtatgcggc gaccgagttg ctcttgcccg gcgtcaatac gggataatac      7740
cgcgccacat agcagaactt aaaagtgct catcattgga aaacgttctt cggggcgaaa       7800
actctcaagg atcttaccgc tgttgagatc cagttcgatg taacccactc gtgcacccaa      7860
ctgatcttca gcatctttta ctttcaccag cgtttctggg tgagcaaaaa caggaaggca      7920
aaatgccgca aaaaagggaa taaggcgac acggaaatgt tgaatactca tactcttcct       7980
ttttcaatat tattgaagca tttatcaggg ttattgtctc atgagcggat acatatttga      8040
atgtatttag aaaaataaac aaataggggg tccgcgcaca tttcccccgaa aagtgccacc     8100 tgacgtcgac ggatcgggag atcaacttgt ttattgcagc ttataatggt tacaaataaa      8160
gcaatagcat cacaaatttc acaaataaag cattttttttc actgcattct agttgtggtt      8220
tgtccaaact catcaatgta tcttatcatg tctggatcaa ctggataact caagctaacc      8280
aaaatcatcc caaacttccc accccatacc ctattaccac tgccaattac ctgtggtttc      8340
atttactcta aacctgtgat tcctctgaat tattttcatt ttaaagaaat tgtatttgtt      8400
aaatatgtac tacaaactta gtagt                                           8425
```

<210> SEQ ID NO 31
<211> LENGTH: 8424
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ggaagggcta attcactccc aaagaagaca agatatcctt gatctgtgga tctaccacac      60
```

-continued

```
acaaggctac ttccctgatt agcagaacta cacaccaggg ccaggggtca gatatccact      120
gacctttgga tggtgctaca agctagtacc agttgagcca gataaggtag aagaggccaa      180
taaaggagag aacaccagct tgttacaccc tgtgagcctg catgggatgg atgacccgga      240
gagagaagtg ttagagtgga ggtttgacag ccgcctagca tttcatcacg tggccccgaga     300 gctgcatccg gagtacttca agaactgctg atatcgagct tgctacaagg actttccgc       360 tggggacttt ccagggaggc gtggcctggg cgggactggg gagtggcgag ccctcagatc      420
ctgcatataa gcagctgctt tttgcctgta ctgggtctct ctggttagac cagatctgag      480
cctgggagct ctctggctaa ctagggaacc cactgcttaa gcctcaataa agcttgcctt      540
gagtgcttca agtagtgtgt gcccgtctgt tgtgtgactc tggtaactag agatccctca      600 gacccttta gtcagtgtgg aaaatctcta gcagtggcgc ccgaacaggg acttgaaagc       660
gaaagggaaa ccagaggagc tctctcgacg caggactcgg cttgctgaag cgcgcacggc      720
aagaggcgag gggcggcgac tggtgagtac gccaaaaatt ttgactagcg gaggctagaa      780
ggagagagat gggtgcgaga gcgtcagtat taagcggggg agaattagat cgcgatggga      840
aaaaattcgg ttaaggccag ggggaaagaa aaaatataaa ttaaaacata tagtatgggc      900
aagcagggag ctagaacgat tcgcagttaa tcctggcctg ttagaaacat cagaaggctg      960
tagacaaata ctgggacagc tacaaccatc ccttcagaca ggatcagaag aacttagatc     1020
attatataat acagtagcaa ccctctattg tgtgcatcaa aggatagaga taaaagacac     1080
caaggaagct ttagacaaga tagaggaaga gcaaacaaa agtaagacca ccgcacagca      1140
agcggccggc cgctgatctt cagacctgga ggaggagata tgagggacaa ttggagaagt     1200
gaattatata aatataaagt agtaaaaatt gaaccattag gagtagcacc caccaaggca     1260
aagagaagag tggtgcagag agaaaaaaga gcagtgggaa taggagcttt gttccttggg     1320
ttcttgggag cagcaggaag cactatgggc gcagcgtcaa tgacgctgac ggtacaggcc     1380
agacaattat tgtctggtat agtgcagcag cagaacaatt gctgagggc tattgaggcg      1440 caacagcatc tgttgcaact cacagtctgg ggcatcaagc agctccaggc aagaatcctg     1500
gctgtggaaa gatacctaaa ggatcaacag ctcctgggga tttggggttg ctctggaaaa     1560
ctcatttgca ccactgctgt gccttggaat gctagttgga gtaataaatc tctggaacag     1620
atttggaatc acacgacctg gatggagtgg gacagagaaa ttaacaatta cacaagctta     1680
atacactcct taattgaaga atcgcaaaac cagcaagaaa agaatgaaca agaattattg     1740
gaattagata aatgggcaag tttgtggaat tggtttaaca taacaaattg ctgtggtat      1800 ataaaattat tcataatgat agtaggaggc ttggtaggtt taagaatagt ttttgctgta     1860
ctttctatag tgaatagagt taggcaggga tattcaccat tatcgtttca gacccacctc     1920
ccaaccccga ggggacccga caggcccgaa ggaatagaag aagaaggtgg agagagagac     1980
agagacagat ccattcgatt agtgaacgga tctcgacggt atcgccttta aaagaaaagg     2040
ggggattggg gggtacagtg cagggaaag aatagtagac ataatagcaa cagacataca     2100
aactaaagaa ttacaaaaac aaattacaaa aattcaaaat tttcgggttt attacaggga     2160
cagcagagat ccagtttatc gattagtcca atttgttaaa gacaggatat cagtggtcca     2220
ggctctagtt ttgactcaac aatatcacca gctgaagcct atagagtacg agccatagat     2280
aaaataaaag attttatttta gtctccagaa aaagggggga atgaaagacc ccacctgtag     2340
gtttggcaag ctaggatcaa ggtcaggaac agagaaacag gagaatatgg gccaaacagg     2400
atatctgtgg taagcagttc ctgccccgct cagggccaag aacagttgga acaggagaat     2460
```

-continued

```
atgggccaaa caggatatct gtggtaagca gttcctgccc cgctcagggc caagaacaga    2520
tggtccccag atgcggtccc gccctcagca gtttctagag aaccatcaga tgtttccagg    2580
gtgccccaag gacctgaaat gaccctgtgc cttatttgaa ctaaccaatc agttcgcttc    2640
tcgcttctgt tcgcgcgctt ctgctccccg agctcaataa aagagcccac aacccctcac    2700
tcggcgcgat cggatctatt tccggtgaat tccgccacca tgagcgagct gattaaggag    2760
aacatgcaca tgaagctgta catggagggc accgtggaca accatcactt caagtgcaca    2820
tccgagggcg aaggcaagcc ctacgagggc acccagacca tgagaatcaa ggtggtcgag    2880
ggcggccctc tccccttcgc cttcgacatc ctggctacta gcttcctcta cggcagcaag    2940
accttcatca accacaccca gggcatcccc gacttcttca agcagtcctt ccctgagggc    3000
ttcacatggg agagagtcac cacatacgaa gacgggggcg tgctgaccgc tacccaggac    3060
accagcctcc aggacggctg cctcatctac aacgtcaaga tcagaggggt gaacttcaca    3120
tccaacggcc ctgtgatgca gaagaaaaca ctcggctggg aggccttcac cgagacgctg    3180
taccccgctg acggcggcct ggaaggcaga aacgacatgg ccctgaagct cgtgggcggg    3240
agccatctga tcgcaaacat caagaccaca tatagatcca agaaacccgc taagaacctc    3300
aagatgcctg gcgtctacta tgtggactac agactggaaa gaatcaagga ggccaacaac    3360
gagacctacg tcgagcagca cgaggtggca gtggccagat actgcgacct ccctagcaaa    3420
ctggggcaca agcttaatgg aggctccggc ggccgcgcaa aacgtgcaac gaatttcagc    3480
ctgctgaagc aggccgggga cgtcgaggag aatcccgggc caatgcagca gcctttcaac    3540
tatccttatc ctcagatcta ttgggtcgat tctagcgcct cttctccttg gcaccacca    3600 gggactgtct tgccatgccc gactagcgtg ccacggagac caggccagcg tcgacctccc    3660
ccacctccac ccccccctcc cctgccacca ccaccccac cacctcccct tccacccttg     3720
ccacttcctc cgcttaagaa acggggaaac cacagcactg gcctctgcct gttggtcatg    3780
ttcttcatgg tgctggttgc actggtggga ctgggattgg ggatgttcca gctgttccac    3840
ttgcagaagg agttggcaga actgagggaa agcactagcc agatgcacac cgcctcagag    3900
gaagccgctg ccatcggtca cccaagcccc ccccagaaa agaaggagct gaggaaggtc      3960
gcacacctca ccggtaaatc caattcccgg tcaatgcccc tggagtggga agacacctat    4020
ggcatcgttc tgctttcagg cgtcaaatac aagaaaggag ggctggttat caatgaaaca    4080
gggctgtatt tcgtttattc caaggtctac tttcgggggc agtcctgtaa caatctccct    4140
ctcagccaca aagtctacat gaggaacagc aaatacccc aggatctggt tatgatggaa     4200
gggaagatga tgagctactg cactaccggc cagatgtggg ccaggagttc ctacctgggt    4260
gccgtcttca accttacttc cgcagaccat ctgtacgtca cgtgagtga actgtccctg      4320 gtgaactttg aggagagtca gaccttttc gggctgtata aactgtgata gggcgcgcca     4380
cgcgtctgga acaatcaacc tctggattac aaaatttgtg aaagattgac tggtattctt    4440
aactatgttg ctccttttac gctatgtgga tacgctgctt taatgccttt gtatcatgct    4500
attgcttccc gtatggcttt cattttctcc tccttgtata aatcctggtt gctgtctctt    4560
tatgaggagt tgtggcccgt tgtcaggcaa cgtggcgtgg tgtgcactgt gtttgctgac    4620 gcaacccca ctggttgggg cattgccacc acctgtcagc tcctttccgg gactttcgct      4680
ttccccctcc ctattgccac ggcggaactc atcgccgcct gccttgcccg ctgctggaca    4740
ggggctcggc tgttgggcac tgacaattcc gtggtgttgt cggggaagct gacgtccttt    4800
```

-continued

```
ccatggctgc tcgcctgtgt tgccacctgg attctgcgcg ggacgtcctt ctgctacgtc    4860
ccttcggccc tcaatccagc ggaccttcct tcccgcggcc tgctgccggc tctgcggcct    4920
cttccgcgtc ttcgccttcg ccctcagacg agtcggatct ccctttgggc cgcctccccg    4980
cctggaatta attctgcagt cgagacctag aaaaacatgg agcaatcaca agtagcaata    5040
cagcagctac caatgctgat tgtgcctggc tagaagcaca agaggaggag gaggtgggtt    5100
ttccagtcac acctcaggta cctttaagac caatgactta caaggcagct gtagatctta    5160
gccacttttt aaaagaaaag aggggactgg aagggctaat tcactcccaa cgaagacaag    5220
atatccttga tctgtggatc taccacacac aaggctactt ccctgattag cagaactaca    5280
caccagggcc aggggtcaga tatccactga cctttggatg gtgctacaag ctagtaccag    5340
ttgagccaga taaggtagaa gaggccaata aaggagagaa caccagcttg ttacaccctg    5400
tgagcctgca tgggatggat gacccggaga gagaagtgtt agagtggagg tttgacagcc    5460
gcctagcatt tcatcacgtg gcccgagagc tgcatccgga gtacttcaag aactgctgat    5520
atcgagcttg ctacaaggga ctttccgctg gggactttcc agggaggcgt ggcctgggcg    5580
ggactgggga gtggcgagcc ctcagatcct gcatataagc agctgctttt tgcctgtact    5640
gggtctctct ggttagacca gatctgagcc tgggagctct ctggctaact agggaaccca    5700
ctgcttaagc ctcaataaag cttgccttga gtgcttcaag tagtgtgtgc ccgtctgttg    5760
tgtgactctg gtaactagag atccctcaga cccttttagt cagtgtggaa aatctctagc    5820
agtagtagtt catgtcatct tattattcag tatttataac ttgcaaagaa atgaatatca    5880
gagagtgaga ggccttgaca ttgctagcgt ttaccgtcga cctctagcta gagcttggcg    5940
taatcatggt catagctgtt tcctgtgtga aattgttatc cgctcacaat tccacacaac    6000
atacgagccg gaagcataaa gtgtaaagcc tggggtgcct aatgagtgag ctaactcaca    6060
ttaattgcgt tgcgctcact gcccgctttc cagtcgggaa acctgtcgtg ccagctgcat    6120
taatgaatcg gccaacgcgc ggggagaggc ggtttgcgta ttgggcgctc ttccgcttcc    6180
tcgctcactg actcgctgcg ctcggtcgtt cggctgcggc gagcggtatc agctcactca    6240
aaggcggtaa tacggttatc cacagaatca ggggataacg caggaaagaa catgtgagca    6300
aaaggccagc aaaaggccag gaaccgtaaa aaggccgcgt tgctggcgtt tttccatagg    6360
ctccgccccc ctgacgagca tcacaaaaat cgacgctcaa gtcagaggtg gcgaaacccg    6420
acaggactat aaagatacca ggcgtttccc cctggaagct ccctcgtgcg ctctcctgtt    6480
ccgaccctgc cgcttaccgg atacctgtcc gcctttctcc cttcgggaag cgtggcgctt    6540
tctcatagct cacgctgtag gtatctcagt tcggtgtagg tcgttcgctc caagctgggc    6600
tgtgtgcacg aacccccegt tcagcccgac cgctgcgcct tatccggtaa ctatcgtctt    6660
gagtccaacc cggtaagaca cgacttatcg ccactggcag cagccactgg taacaggatt    6720
agcagagcga ggtatgtagg cggtgctaca gagttcttga agtggtggcc taactacggc    6780
tacactagaa gaacagtatt tggtatctgc gctctgctga agccagttac cttcggaaaa    6840
agagttggta gctcttgatc cggcaaacaa accaccgctg gtagcggtgg ttttttttgtt    6900 tgcaagcagc agattacgcg cagaaaaaaa ggatctcaag aagatccttt gatcttttct    6960
acggggtctg acgctcagtg gaacgaaaac tcacgttaag ggattttggt catgagatta    7020
tcaaaaagga tcttcaccta gatccttta aattaaaaat gaagttttaa atcaatctaa    7080
agtatatatg agtaaacttg gtctgacagt taccaatgct taatcagtga ggcacctatc    7140
tcagcgatct gtctatttcg ttcatccata gttgcctgac tccccgtcgt gtagataact    7200
```

```
acgatacggg agggcttacc atctggcccc agtgctgcaa tgataccgcg agacccacgc    7260
tcaccggctc cagatttatc agcaataaac cagccagccg gaagggccga gcgcagaagt    7320
ggtcctgcaa ctttatccgc ctccatccag tctattaatt gttgccggga agctagagta    7380
agtagttcgc cagttaatag tttgcgcaac gttgttgcca ttgctacagg catcgtggtg    7440
tcacgctcgt cgtttggtat ggcttcattc agctccggtt cccaacgatc aaggcgagtt    7500
acatgatccc ccatgttgtg caaaaaagcg gttagctcct tcggtcctcc gatcgttgtc    7560
agaagtaagt tggccgcagt gttatcactc atggttatgg cagcactgca taattctctt    7620
actgtcatgc catccgtaag atgcttttct gtgactggtg agtactcaac caagtcattc    7680
tgagaatagt gtatgcggcg accgagttgc tcttgcccgg cgtcaatacg ggataatacc    7740
gcgccacata gcagaacttt aaaagtgctc atcattggaa aacgttcttc ggggcgaaaa    7800
ctctcaagga tcttaccgct gttgagatcc agttcgatgt aacccactcg tgcacccaac    7860
tgatcttcag catcttttac tttcaccagc gtttctgggt gagcaaaaac aggaaggcaa    7920
aatgccgcaa aaaagggaat aagggcgaca cggaaatgtt gaatactcat actcttcctt    7980
tttcaatatt attgaagcat ttatcagggt tattgtctca tgagcggata catatttgaa    8040
tgtatttaga aaaataaaca aataggggtt ccgcgcacat ttccccgaaa agtgccacct    8100
gacgtcgacg gatcgggaga tcaacttgtt tattgcagct tataatggtt acaaataaag    8160
caatagcatc acaaatttca caaataaagc attttttttca ctgcattcta gttgtggttt    8220
gtccaaactc atcaatgtat cttatcatgt ctggatcaac tggataactc aagctaacca    8280
aaatcatccc aaacttccca ccccataccc tattaccact gccaattacc tgtggtttca    8340
tttactctaa acctgtgatt cctctgaatt attttcattt taaagaaatt gtatttgtta    8400
aatatgtact acaaacttag tagt                                            8424
```

```
<210> SEQ ID NO 32
<211> LENGTH: 5
<212> TYPE: PRT
<213> ORGANISM: Homo sapiens

<400> SEQUENCE: 32

Ser Leu Glu Lys Gln
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Glu Ala Ala Ala
1               5

<210> SEQ ID NO 34
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
```

-continued

```
atgcagcagc ctttcaacta tccttatcct cagatctatt gggtcgattc tagcgcctct        60
tctccttggg caccaccagg gactgtcttg ccatgcccga ctagcgtgcc acggagacca       120
ggccagcgtc gacctccccc acctccaccc ccccctcccc tgccaccacc accccccacca     180 cctccccttc cacccttgcc acttcctccg cttaagaaac ggggaaacca cagcactggc       240
ctctgcctgt tggtcatgtt cttcatggtg ctggttgcac tggtgggact gggattgggg       300
atgttccagc tgttccactt gcagaaggag ttggcagaac tgagggaaag cactagccag       360
atgcacaccg cctcaagctt ggagaagcag atcggtcacc caagcccccc cccagaaaag      420
aaggagctga ggaaggtcgc acacctcacc ggtaaatcca attcccggtc aatgcccctg       480
gagtgggaag acacctatgg catcgttctg ctttcaggcg tcaaatacaa gaaaggaggg      540
ctggttatca atgaaacagg gctgtatttc gtttattcca aggtctactt tcggggggcag      600 tcctgtaaca atctccctct cagccacaaa gtctacatga ggaacagcaa ataccccag       660 gatctggtta tgatggaagg gaagatgatg agctactgca ctaccggcca gatgtgggcc       720
aggagttcct acctgggtgc cgtcttcaac cttacttccg cagaccatct gtacgtcaac       780
gtgagtgaac tgtccctggt gaactttgag gagagtcaga ccctgttcgg gctgtataaa      840
ctg                                                                      843
```

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Ser Gly Gly
1               5

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gly Gly Ser Gly Gly Gly Gly Ser Gly Gly Gly Gly Ser
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser Gly Gly Gly Gly Ser Gly
1               5                   10                  15

Gly Gly Gly Ser
            20

<210> SEQ ID NO 38
<211> LENGTH: 18
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 38

Gly Ser Thr Ser Gly Ser Gly Lys Pro Gly Ser Gly Glu Gly Ser Thr
1               5                   10                  15

Lys Gly
```

FASL EXPRESSION AND FASR GENE KNOCKOUT TO PROTECT THERAPEUTIC CELLS FROM ALLOGENEIC REJECTION AND ACTIVATION-INDUCED CELL DEATH

CROSS REFERENCE TO RELATED APPLICATIONS

The present application claims the benefit of priority to U.S. Provisional Application No. 63/156,902, filed Mar. 4, 2021, the content which is hereby incorporated by reference in its entirety.

SEQUENCE LISTING

This application contains a Sequence Listing which has been submitted electronically in ASCII format and is hereby incorporated by reference in its entirety. Said ASCII copy, created on Feb. 24, 2022, is named AT-040_02US_SL.txt and is 101,988 bytes in size.

FIELD

The present disclosure relates generally to the use of immune cells (e.g., a T cell) engineered to express a chimeric antigen receptor (CAR) to treat a disease.

BACKGROUND

Targeted cell therapies employ genetic engineering to arm immune effector cells with cancer-targeting receptors (T cell receptors (TCRs) or chimeric antigen receptors (CARs)) and then infuse these engineered cells into patients with cancer in an autologous or allogeneic setting. Adoptive transfer of immune cells genetically modified to recognize malignancy-associated antigens has emerged as a powerful approach to treating cancer (see, e.g., Brenner et al., Current Opinion in Immunology, 22(2): 251-257 (2010); Rosenberg et al., Nature Reviews Cancer, 8(4): 299-308 (2008)). Immune cells can be genetically modified to express chimeric antigen receptors (CARs), fusion proteins comprised of an antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)). Immune cells that contain CARs, e.g., CAR-T cells (CAR-Ts), are engineered to endow them with antigen specificity while retaining or enhancing their ability to recognize and kill a target cell.

However, the generation of CAR-modified autologous cell therapies is expensive, requires weeks of process and quality testing, and yields product of variable potency depending on the initial quality and quantity of patient-specific T cells employed. Relative to autologous therapies, allogeneic CAR-modified cell therapies—in which cells from a healthy donor are modified with CAR and then administered to multiple patients—promises a cheaper and more robust product that can be delivered immediately upon need (see, e.g., Graham et al., Cells 2018, 7, 155; doi: 10.3390/cells7100155). Additionally, allogeneic therapies enable selection on desirable product characteristics (e.g. gene editing efficiency, site of integration, lack of deleterious off-target gene edits, haplotype, etc.), and facilitate more sophisticated cell engineering (e.g. multiple gene edits improving potency, persistence, homing, etc.). The key hurdle to implementing allogeneic CAR-modified cell therapies is the potential for rejection of the product (donor) by the immune system of the patient (host).

Additionally, and like autologous cell therapies, allogeneic effector cells that infiltrate the tumor microenvironment succumb over time to activation-induced cell death (AICD), limiting therapeutic persistence.

While allogeneic cell therapies present a number of advantages over autologous cell therapies, allogeneic cells also face rejection by host or recipient immune system cells reactive with T and NK epitope determinants on the surface of the allogeneic cell product that are distinct from host. The present disclosure provides the advantages of improved allogeneic therapies that provide increased persistence of the administered cells despite the recipients' natural defenses.

SUMMARY

The present disclosure provides a counter-attack strategy whereby receptor-modified cell therapy products (e.g. immune cells e.g. T cells engineered to express an antigen binding protein e.g. a CAR) are further genetically engineered in two respects. First, the cells are engineered to heterologously express the Fas ligand (also known as FasL or CD178) protein or a derivative thereof from a nucleic acid that encodes the protein. Second, the cells are genetically modified such that the expression level of the Fas receptor (also known as Fas, FasR or CD95) gene is reduced (e.g. eliminated via knockout). Expression of FasL enables product cells to kill alloreactive host T and natural killer (NK) cells that express FasR upon activation, because FasR binding of FasL triggers apoptosis in the FasR-expressing cell. Reducing a cell's expression level of FasR (e.g. eliminating FasR expression in the cell) protects product cells from FasL-induced fratricide and AICD.

The present disclosure provides, among other things, compositions, methods and related materials, e.g. expression vectors, engineered cells and compositions, for improving therapies that entail the administration of allogeneic cells to a patient. One aspect of the disclosure is an immune cell e.g. a T cell that is modified so that it comprises and/or expresses FasL protein or a FasL protein derivative (e.g. from an expression vector comprising a polynucleotide that encodes FasL protein or a FasL protein derivative). A second aspect of the disclosure is an immune cell e.g. a T cell that is modified so that it expresses FasR at a reduced level (e.g. by genetically modifying the cell using any gene mutation or gene editing technique). In embodiments of both aspects, the immune cell e.g. T cell is further modified so that it comprises and/or expresses an antigen binding protein e.g. a chimeric antigen receptor (CAR) (e.g. from an expression vector comprising a polynucleotide that encodes the antigen binding protein e.g. CAR). In some embodiments, an immune cell e.g. T cell comprises two or three of these modifications. Thus, for example, the disclosure provides an improved method of CAR T-cell therapy that comprises administering immune cells e.g. T cells that have been modified to express an antigen binding protein e.g. a CAR, to express a reduced level of FasR or not to express FasR at all (e.g. FasR knockout), and to express FasL protein or a FasL derivative protein. It thus further provides an improved method of CAR T-cell therapy in which AICD is reduced and/or persistence e.g. therapeutic persistence of the administered cells comprising the three modifications is increased relative to administered cells modified only to express an antigen binding protein e.g. CAR.

In one aspect, provided herein is a vector comprising a first polynucleotide encoding an antigen binding protein and a second polynucleotide encoding a FasL protein or a FasL protein derivative. In an embodiment, the antigen binding protein is a chimeric antigen receptor (CAR). In an embodiment, the amino acid sequence of the FasL protein or FasL protein derivative consists of or comprises the amino acid sequence of UniprotKB-P48023 (wild-type human FasL, SEQ ID NO:3), human FasL delta 2-74 (SEQ ID NO:7), human FasL Q130D (SEQ ID NO:10), human FasL C82A (SEQ ID NO:8) or human FasL SLEKQ126-130→EEAAA (SEQ ID NO:9) ("SLEKQ" and "EEAAA" disclosed as SEQ ID NOs: 32 and 33, respectively).

In an embodiment, the vector further comprises a 2A peptide-encoding sequence (SEQ ID NO:2) between the polynucleotide encoding a recombinant antigen receptor and the polynucleotide encoding the FasL protein or a FasL protein derivative and/or comprises a posttranscriptional regulatory element (PRE) e.g. WPRE. In an embodiment, the vector is a viral vector e.g. a lentiviral vector.

In another aspect, provided herein is an engineered immune cell comprising the vector provided herein. In an embodiment, the engineered immune cell is modified e.g. genetically modified such that FasR expression level is reduced compared to engineered immune cells not modified to reduce FasR expression level.

In another aspect, provided herein is an engineered immune cell, e.g. an isolated engineered immune cell, comprising an antigen binding protein and FasL protein or a FasL protein derivative, wherein the engineered immune cell is modified e.g. genetically modified such that FasR expression level is reduced compared to engineered immune cells that are the same but have not been genetically modified to reduce FasR expression level. In an embodiment, the antigen binding protein is a chimeric antigen receptor (CAR). In an embodiment, in an engineered immune cell as disclosed herein, the FasL protein or the FasL protein derivative is any one or more of wildtype human FasL, human FasL delta 2-74, human FasL Q130D, human FasL C82A and human FasL SLEKQ126-130→EEAAA (SEQ ID NOs: 32 and 33, respectively).

In various embodiments, the engineered immune cell disclosed herein is an engineered T cell (e.g. an engineered alpha/beta T cell and/or an engineered gamma/delta T cell), B cell, natural killer (NK) cell, natural killer T (NKT) cell, mast cell, and/or myeloic-derived phagocyte. In certain embodiments, the engineered immune cell is an engineered T cell, e.g. a CAR T cell. In various embodiments of the engineered immune cell disclosed herein, the engineered immune cell is a human engineered immune cell e.g. a human engineered T cell.

In various embodiments of the engineered immune cell disclosed herein, wherein the immune cell has been engineered as described herein to express one or more genes such as, but not limited to, FasR, CD52 and TCR-alpha, at a reduced level, the expression level of the gene is decreased by or by at least about 30%, 35%, 40%, 45%, 50%, 55%, 60%, 65%, 70%, 75%, 80%, 85%, 90%, 95%, 99%, or 100% (e.g. a gene knockout) relative to the gene's expression level in a corresponding cell not so modified, that is, in a control cell. In some embodiments, the gene's expression level is measured at the cell surface. In some embodiments, cell surface expression levels of the gene is measured by flow cytometry.

In another aspect, provided herein is an engineered immune cell comprising a polynucleotide encoding an antigen binding protein and a polynucleotide encoding FasL protein or a FasL protein derivative. In an embodiment, the engineered immune cell is modified e.g. genetically modified such that FasR expression level is reduced compared to engineered immune cells in which the genome is not modified to reduce FasR expression. In an embodiment, the antigen binding protein is a chimeric antigen receptor (CAR). In an embodiment, the amino acid sequence of the FasL protein or FasL protein derivative consists of or comprises the amino acid sequence of UniprotKB-P48023 (SEQ ID NO:3), FasL delta 2-74 (SEQ ID NO:7), FasL Q130D (SEQ ID NO:10), FasL C82A (SEQ ID NO:8) or FasL SLEKQ126-130→EEAAA (SEQ ID NO:9) ("SLEKQ" and "EEAAA" disclosed as SEQ ID NO: 32 and 33, respectively).

In an embodiment, an engineered immune cell as disclosed herein further comprises one or more genomic modifications of one or more of the endogenous TCRa gene and the endogenous CD52 gene.

In another aspect, the present disclosure provides a method of making the engineered immune cell disclosed herein. In an embodiment, the method comprises the use of any gene editing technology, such as TALEN, zinc fingers, shRNA, Cas-CLOVER, and a CRISPR/Cas system, and/or the use of any known gene knockdown methods e.g. those that employ any of various RNA-based techniques (e.g. antisense RNA, miRNA, siRNA; see, e.g., Lam et al., Mol. Ther.-Nucleic Acids 4:e252 (2015), doi:10.1038/mtna.2015.23; Sridharan and Gogtay, Brit. J. Clin. Pharma-col. 82: 659-72 (2016)) to reduce functional expression of FasR. In an embodiment, the method comprises or further comprises the introduction into the engineered immune cell of a nucleic acid encoding a FasL protein or a FasL protein derivative as described herein and/or an antigen binding protein, e.g. a CAR or TCR. In an embodiment, the method comprises or further comprises introducing into the genome of the engineered immune cell one or more genomic modifications of one or more of an endogenous TCRa gene and an endogenous CD52 gene. In an embodiment, the one or more genomic modifications disrupts and/or prevents, wholly or partly, the functional expression of one or more of an endogenous TCRa gene and an endogenous CD52 gene.

In another aspect, provided herein is a population of immune cells comprising one or more of the engineered immune cells disclosed herein. In an embodiment, a population of immune cells as disclosed herein comprises $10^4$ or more, $10^5$ or more, $10^6$ or more, or $10^7$ or more of an engineered cell as disclosed herein. In an embodiment, a population of immune cells as disclosed herein is enriched for the engineered immune cell as disclosed herein. In various embodiments, the population of immune cells is at least 20%, 30%, 40% or 50% engineered immune cells, e.g. is 20%, 30% 40%, 50%, 55%, 60%, 65%, 70%, 75%, 80%, 85%, 90%, 95%, or is more than 95% engineered immune cells that are, e.g., T cells (e.g. alpha/beta T cells and/or gamma/delta T cells), B cells, natural killer (NK) cells, natural killer T (NKT) cells, mast cells, and/or myeloic-derived phagocytes. In various embodiments, the population of immune cells is at least 20%, 30%, 40% or 50% engineered T cells, e.g. is 20%, 30% 40%, 50%, 55%, 60%, 65%, 70%, 75%, 80%, 85%, 90%, 95%, or more than 95% engineered T cells.

In another aspect, provided herein is a pharmaceutical composition comprising an engineered immune cell as disclosed herein or a population of immune cells comprising an engineered immune cell as disclosed herein, and a pharmaceutically acceptable carrier. In an embodiment, the engineered immune cell comprises a polynucleotide encoding an antigen binding protein and a polynucleotide encoding FasL protein or a FasL protein derivative and optionally further is modified e.g. genetically modified such that the engineered immune cell's FasR expression level is reduced compared to engineered immune cells in which the genome is not modified to reduce FasR expression.

In another aspect, provided herein is a method of treating a condition in a patient comprising administering to the patient an engineered immune cell as disclosed herein. In an embodiment of the method, the engineered immune cell is an allogeneic engineered immune cell derived from a donor other than the patient.

In another aspect, provided herein is a method of treating a condition in a patient comprising administering to the patient a population of immune cells as disclosed herein. In an embodiment of the method, the immune cells of the population are derived from one or more allogeneic immune cells from a donor other than the patient.

In another aspect, provided herein is a method of treating a condition in a patient comprising administering to the patient a pharmaceutical composition as disclosed herein. In an embodiment of the method, the composition comprises one or more engineered allogeneic immune cells derived from a donor other than the patient.

In embodiments of the methods of treating disclosed herein, the disorder can be cancer, autoimmune disease, or infection. In some embodiments, the administered cell, population of cells or composition can be administered more than once. In some embodiments, the cell, population of cells or composition can be administered to the subject on two or more occasions spaced at least about 1, 2, 3, 4, 5, 6, 7, or more days apart. In some embodiments, the disorder can be a viral disease, a bacterial disease, a cancer, an inflammatory disease, an immune disease, or an aging-associated disease.

In some embodiments, the cancer can be a hematological malignancy or a solid cancer. In some embodiments, the hematological malignancy can be acute lymphoblastic leukemia (ALL), acute myeloid leukemia (AML), chronic myelogenous leukemia (CML), chronic eosinophilic leukemia (CEL), myelodysplasia syndrome (MDS), non-Hodgkin's lymphoma (NHL), or multiple myeloma (MM). In some embodiments, the solid cancer can be selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, or uterine cancer.

In another aspect, provided herein is a method for reducing host cell killing e.g. activation-induced cell death (AICD) of allogeneic cells in a therapeutic regimen that comprises administering allogeneic cells to a patient, the method comprising administering to the patient an engineered immune cell, population of cells or composition as disclosed herein. In some embodiments, host cell killing e.g. activation-induced cell death (AICD) is reduced by between 10% and 90%. In some embodiments, host cell killing e.g. activation-induced cell death (AICD) is reduced by over 90%.

In another aspect, provided herein is a method of enhancing or increasing the persistence of allogeneic cells in a patient. In an embodiment, the method comprises administering to the patient an engineered immune cell, population of cells or pharmaceutical composition as disclosed herein. In some embodiments, administering a cell, population of cells or composition disclosed herein results in persistence that is improved or increased by, or by at least, 10%, 20%, 30%, 40%, 50%, 60%, 70%, 80%, 90%, 95%, 99%, or 100%, or by a percentage that falls within a range whose endpoints are any two of the recited percentages, as compared to administering a comparable cell, population of cells or composition wherein, e.g., the cells comprise a CAR and do not express FasL and do not express FasR at a reduced level. In some embodiments, the difference in persistence is measured by comparing the half-life of the administered cells in the population or composition, wherein, for example, the half-life is increased by or by at least 10%, 20%, 30%, 40%, 50%, 75%, 100%, or 200%, or by a percentage that falls within a range whose endpoints are any two of the recited percentages.

In some embodiments, administering an engineered immune cell e.g. T cell as disclosed herein, a population of engineered immune cells e.g. T cells as disclosed herein, or a composition comprising engineered immune cells as disclosed herein, results in persistence that is increased relative to the persistence of a corresponding immune cell, population of immune cells or composition comprising immune cells that have not been so engineered. In some embodiments, persistence is increased by, for example, between 1 and 7 days, by between 1 and 12 weeks (e.g. between 1 and 4 weeks, 4 and 8 weeks, or 8 and 12 weeks), or by between 1 and 12 months, or by a specific length of time that falls within these ranges. In some embodiments, the difference in persistence is measured by comparing the half-life of the administered cells in the population or composition, wherein, for example, the half-life is increased by, for example, between 1 and 7 days, by between 1 and 12 weeks (e.g. between 1 and 4 weeks, 4 and 8 weeks, or 8 and 12 weeks), or by between 1 and 12 months, or by a specific length of time that falls within these ranges. In some embodiments, the difference in persistence is measured by comparing the length of time that the administered cells can be detected after administration. In some embodiments, the improvement in persistence is measured in vitro by comparing the survival of engineered and non-engineered cells in the presence of, for example, immune cells such as T cells or NK cells, e.g. at about 72 hours, 5 days, or 7 days after mixing. In some embodiments, in such an in vitro assay, at the time of measurement, between about 1.5 and 10 times as many engineered cells survive as do cells that are not engineered.

In some embodiments, reduction in host rejection and/or increases in persistence of administered cells as disclosed herein are determined by any of a variety of techniques known to the person of ordinary skill in the art. In some embodiments, any one or a combination of the following is used: flow cytometry, PCR e.g. quantitative PCR, and ex vivo coincubation with patient tumor material or with a model tumor cell line expressing the antigen targeted by the CAR-T cell. In some embodiments, qPCR is used to assess the number of CAR T cells that have and do not have the knock-out of interest in order to determine the extent to which the knock-out provides a survival advantage.

BRIEF DESCRIPTION OF THE DRAWINGS

FIG. 1A. Primary T cells were unstimulated or repeatedly stimulated (red dots on timeline) with TransAct in the presence of 100

U/mL IL-2. Events were designated as live, dead, or debris based on forward scatter, side scatter, and 7-AAD uptake as evaluated by flow cytometry. FIG. 1B. Quantification of surface CD69 and FasR expression over a timecourse of repeated stimulation. FIG. 1C. Quantification of live cells, dead cells, and debris over a timecourse of repeated stimulation. Data in FIGS. 1B and 1C are mean+SD from three technical replicates.

FIG. 3A. Flow cytometry pseudo-colored dot plots showing FasR expression in activated primary T cells with or without electroporation of Cas9-complexed FasR sgRNA. FIG. 3B. Quantification of FasR KO efficiency in activated primary T cells. Mean+SD is shown for three technical replicates.

FIG. 5A. Schematic cartoon of wild-type FasL vector insert generated. Mutant derivatives generated are designated above the schematic. FIG. 5B. Flow cytometry pseudocolored dot plots showing primary T cells one week after concurrent electroporation with Cas9-complexed FasR sgRNA and transduction (without purifi-cation for FasR knockout) with MND-driven lentivectors delivering BFP and a derivative of FasL. Donor is HLA-A2+. wt, wild-type. NTD, untransduced.

FIG. 8A. Activated NK cells completely killed β2m knockout cells that were either untransduced or transduced with inactive FasL. By contrast, β2m knockout cells were protected from NK cell-mediated killing when they expressed an active deriva-tive of FasL. FIG. 8B. As hypothesized, the mechanism of this protection was FasL-mediated counterattack, as live NK cell counts were dramatically reduced in incubations includ-ing T cells armed with active FasL. This killing was specific for FasR+ NK cells, as they were extirpated from these samples and all remaining NK cells were FasR− (data not shown).

FIG. 9A. Cartoon depiction of cells used in assay with gene edits and transduced genes indicated. FIG. 9B. Non-specific effector cells (lacking F5 TCR) did not deplete antigen+graft/product cells at a ratio of 3:1. By contrast, specific effector cells (expressing F5 TCR) depleted antigen+graft/product cells in a dose-dependent manner. Cell populations in which FasR KO cells were present were depleted to a significantly lesser extent (p<0.01, multiple t test analysis) than cell populations replete for FasR, indicating FasR KO provides protection from antigen-specific T cell-mediated killing.

DETAILED DESCRIPTION

Figure 1A:
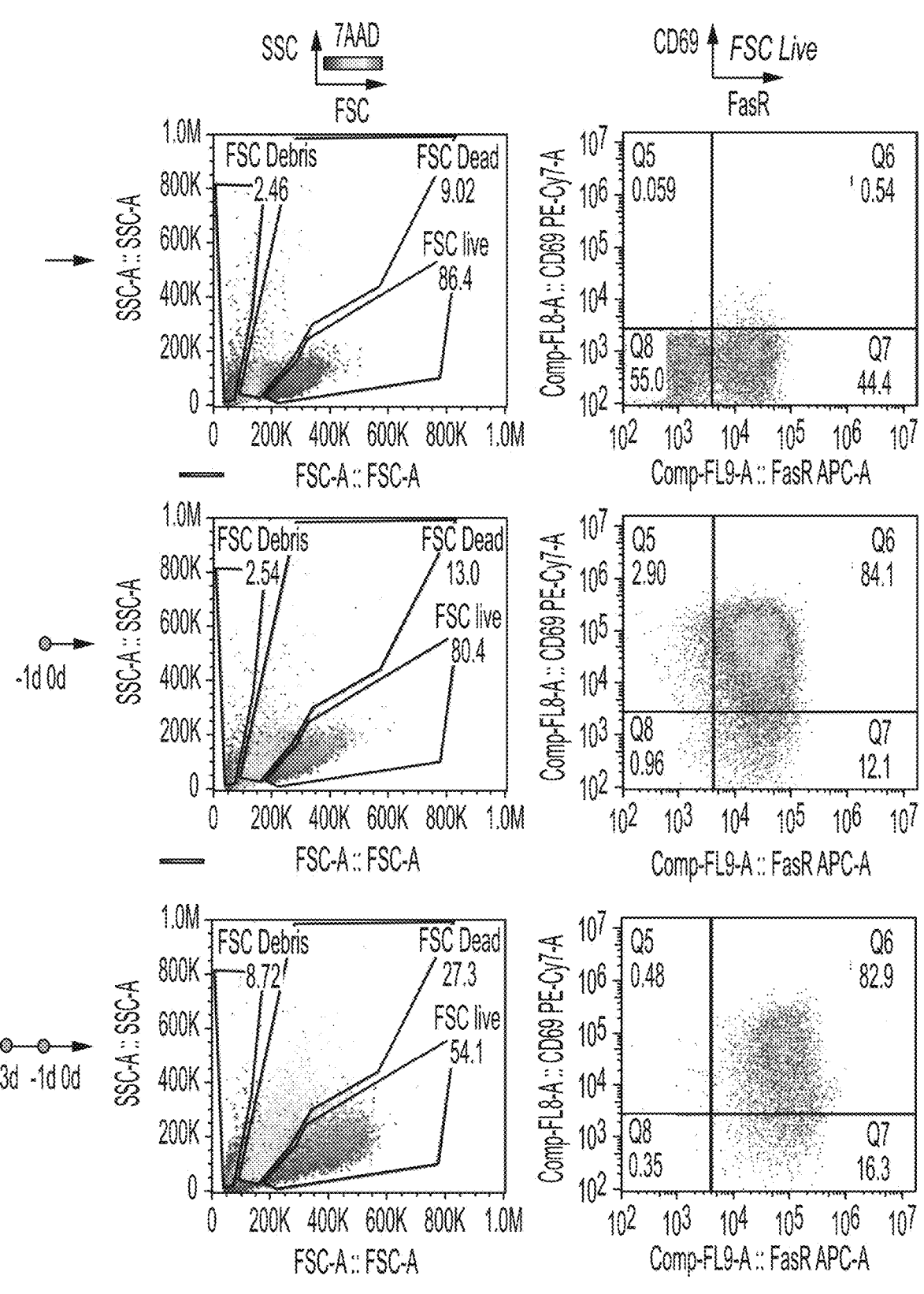
FIGS. 1A-1C. Stimulated T cells express FasR and repeat stimulation results in activation-induced cell death.
Figure 1A:
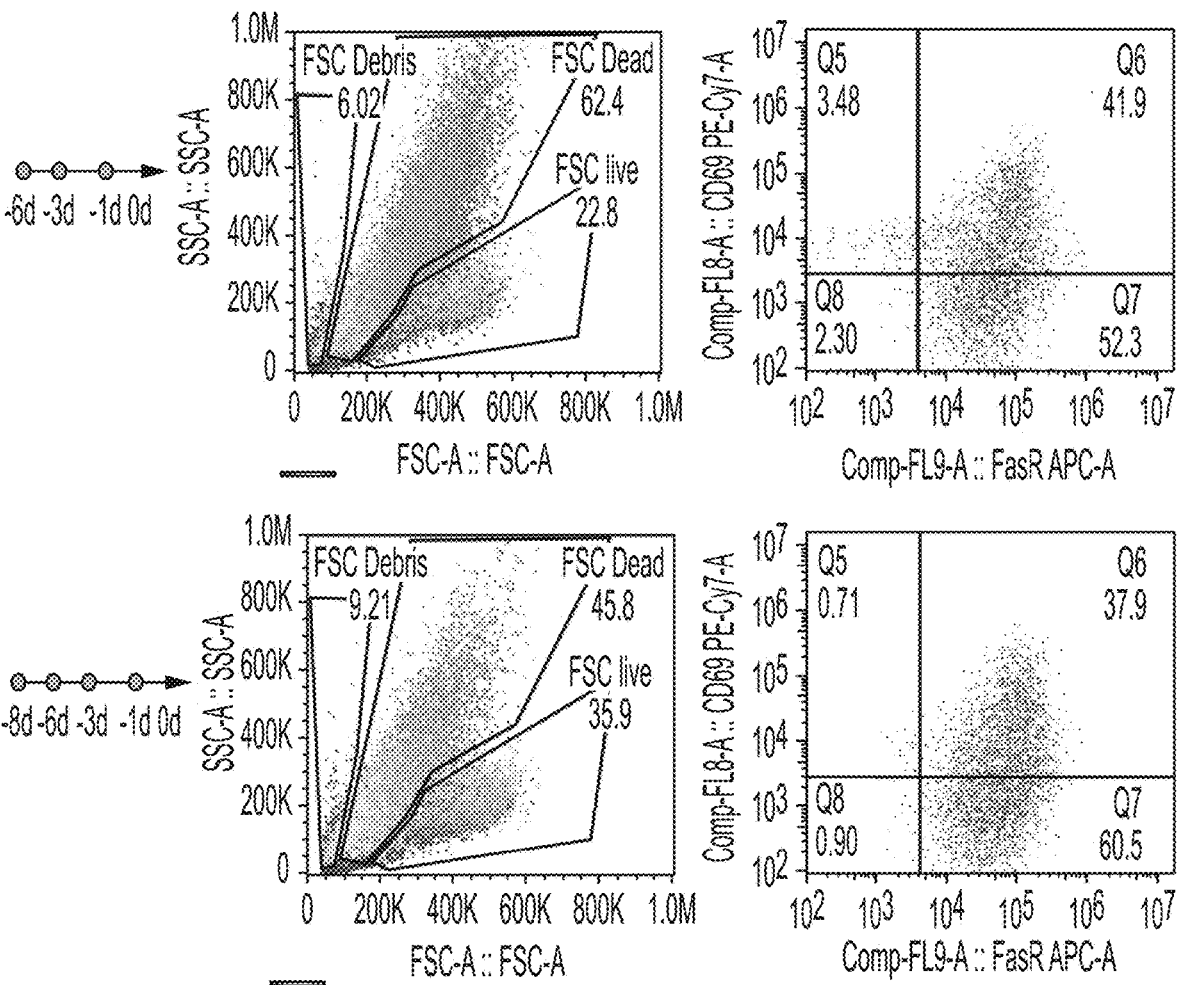

The present disclosure provides, among other things, compositions, methods and related materials, e.g. expression vectors and compositions, for improving therapies that entail the administration of allogeneic cells to a patient. One aspect of the disclosure is an immune cell e.g. a T cell that is modified in two respects: first, it is modified so that it expresses FasL protein or a FasL protein derivative (e.g. from an expression vector comprising a polynucleotide that encodes FasL protein or a FasL protein derivative), and second, it is modified so that it expresses FasR at a reduced level (e.g. by genetically modifying the cell using, for example, any known gene editing techniques that employ, including but not limited to known homologous recombi-nation techniques and techniques that employ any one or more of meganucleases, TALEN, zinc fingers, shRNA, Cas-CLOVER, and a CRISPR/Cas system to partially or wholly delete the FasR gene locus). In some embodiments, the immune cell e.g. T cell is modified in a third respect so that it expresses an antigen binding protein e.g. a chimeric antigen receptor (CAR) (e.g. from an expression vector comprising a polynucleotide that encodes the antigen bind-ing protein e.g. CAR). Thus, for example, the present disclosure provides an improved method of CAR T-cell therapy that comprises administering immune cells e.g. T cells that comprise the three modifications of CAR expres-sion, FasL protein or FasL derivative protein expression, and reduced FasR expression. It thus further provides an improved method of allogeneic CAR T-cell therapy in which AICD is reduced and/or persistence e.g. therapeutic persis-tence of the administered cells comprising the three modifications is increased relative to administered cells that are the same except they are not modified with respect to FasR expression.

General Techniques

The practice of the disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995). Gene editing techniques that employ, for example, meganucleases, TALEN, zinc fingers, shRNA, Cas-CLOVER, and a CRISPR/Cas system, are within the skill of the art and explained fully in the literature, such as T. Gaj et al., Genome-Editing Technologies: Principles and Applications, *Cold Spring Hart Perspect Biol* 2016; 8:a023754 and citations therein.

Definitions

As used herein "autologous" means that cells, a cell line, or population of cells used for treating subjects are originating from said subject.

As used herein "allogeneic" means that cells or population of cells used for treating subjects are not originating from said subject but from a donor.

As used herein, the term "endogenous" refers to any material from or produced inside an organism, cell, tissue or system.

As used herein, the term "exogenous" refers to any material introduced from or produced outside an organism, cell, tissue or system.

As used herein, "immune cell" refers to a cell of hematopoietic origin functionally involved in the initiation and/or execution of innate and/or adaptive immune response. Examples of immune cells include T cells, e.g., alpha/beta T cells and gamma/delta T cells, B cells, natural killer (NK) cells, natural killer T (NKT) cells, mast cells, and myeloic-derived phagocytes.

As used herein, the term "expression" refers to the transcription and/or translation of a particular nucleotide sequence driven by a promoter.

As used herein, "expression vector" refers to a vector comprising a recombinant polynucleotide comprising expression control sequences operatively linked to a nucleotide sequence to be expressed. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

As used herein, "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter).

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

"Promoter" and "promoter sequence" are used interchangeably and refer to a DNA sequence capable of controlling the expression of a coding sequence or functional RNA. In general, a coding sequence is located 3' to a promoter sequence. It is understood by those skilled in the art that different promoters may direct the expression of a gene in different tissues or cell types, or at different stages of development, or in response to different environmental or physiological conditions.

In any of the vectors of the present disclosure, the vector optionally comprises a promoter disclosed herein.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) disclosed herein.

The term "extracellular ligand-binding domain" as used herein refers to an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. The term "stalk domain" is used herein to refer to any oligo- or polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

A "co-stimulatory molecule" as used herein refers to the cognate binding partner on a T cell that specifically binds with a co-stimulatory ligand, thereby mediating a co-stimulatory response by the cell, such as, but not limited to proliferation. Co-stimulatory molecules include, but are not limited to an MEW class I molecule, BTLA and Toll ligand receptor. Examples of costimulatory molecules include CD27, CD28, CD8, 4-1 BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1 BBL, OX40L, inducible costimulatory ligand (ICOS-L), intercellular adhesion molecule (ICAM, CD30L, CD40, CD70, CD83, HLA-G, MICA, M1 CB, HVEM, lymphotoxin β receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1 BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also antigen-binding fragments thereof (such as Fab, Fab', F(ab')2, and Fv), and any other modified configuration of the immunoglobulin molecule that comprises an antigen recognition site including, for example without limitation, single chain (scFv) and domain antibodies (including, for example, shark and camelid antibodies), and fusion proteins comprising an antibody. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., lgG1, lgG2, lgG3, lgG4, lgA1 and lgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen-binding fragment" or "antigen binding portion" of an antibody, as used herein, refers to one or more fragments of an intact antibody that retain the ability to specifically bind to a given antigen. Antigen binding functions of an antibody can be performed by fragments of an intact antibody. Examples of binding fragments encompassed within the term "antigen binding fragment" of an antibody include Fab; Fab'; F(ab')2; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "specifically binds" to a target is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. It is also understood that by reading this definition, for example, an antibody (or moiety or epitope) that specifically binds to a first target may or may not specifically bind to a second target. As such, "specific binding" does not necessarily require (although it can include) exclusive binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1 156-1 166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

Antibodies disclosed herein can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

As used herein, "transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure. The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present disclosure. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein, "treatment" is an approach for obtaining beneficial or desired clinical results. For purposes of this disclosure, beneficial or desired clinical results include, but are not limited to, one or more of the following: reducing the proliferation of (or destroying) neoplastic or cancerous cells, inhibiting metastasis of neoplastic cells, shrinking or decreasing the size of tumor, remission of a disease (e.g., cancer), decreasing symptoms resulting from a disease (e.g., cancer), increasing the quality of life of those suffering from a disease (e.g., cancer), decreasing the dose of other medications required to treat a disease (e.g., cancer), delaying the progression of a disease (e.g., cancer), curing a disease (e.g., cancer), and/or prolong survival of subjects having a disease (e.g., cancer).

"Ameliorating" means a lessening or improvement of one or more symptoms as compared to not administering a treatment. "Ameliorating" also includes shortening or reduction in duration of a symptom. As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various diseases or conditions (such as for example cancer), decreasing the dose of other medications required to treat the disease, enhancing the effect of another medication, and/or delaying the progression of the disease. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, a "subject" is any mammal, e.g a human, or a monkey. Mammals include, but are not limited to, farm animals, sport animals, pets, primates, horses, dogs, cats, mice and rats. In an exemplary embodiment, the subject is a human. In an exemplary embodiment, the subject is a monkey, e.g. a cynomolgus monkey.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "pharmaceutically acceptable carrier" or "pharmaceutically acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions disclosed herein comprising such carriers are formulated by well-known conventional methods (see, for example, Remington's Pharmaceutical Sciences, 18th edition, A. Gennaro, ed., Mack Publishing Co., Easton, PA, 1990; and Remington, The Science and Practice of Pharmacy 21 st Ed. Mack Publishing, 2005).

As used herein, "alloreactivity" refers to the ability of T cells to recognize MEW complexes that were not encountered during thymic development. Alloreactivity manifests itself clinically as hostversus graft rejection and graft versus host disease.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of and/or "consisting essentially of" are also provided.

Where aspects or embodiments of the present disclosure are described in terms of a Markush group or other grouping of alternatives, the disclosed subject matter encompasses not only the entire group listed as a whole, but each member of the group individually and all possible subgroups of the main group, but also the main group absent one or more of the group members. The present disclosure also envisages the explicit exclusion of one or more of any of the group members of the disclosed subject matter.

Unless otherwise defined, all technical and scientific terms used herein have the same meaning as commonly understood by one of ordinary skill in the art to which the present disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the subject matter disclosed herein. The materials, methods, and examples are illustrative only and not intended to be limiting.

An "antigen binding protein" comprises one or more antigen binding domains. An "antigen binding domain" as used herein means any polypeptide that binds a specified target antigen. In some embodiments, the antigen binding domain binds to an antigen on a tumor cell. In some embodiments, the antigen binding domain binds to an antigen on a cell involved in a hyperproliferative disease or to a viral or bacterial antigen.

Antigen binding domains include, but are not limited to, antibody binding regions that are immunologically functional fragments. The term "immunologically functional fragment" (or "fragment") of an antigen binding domain is a species of antigen binding domain comprising a portion (regardless of how that portion is obtained or synthesized) of an antibody that lacks at least some of the amino acids present in a full-length chain, but which is still capable of specifically binding to a target antigen. Such fragments are biologically active in that they bind to the target antigen and can compete with other antigen binding domains, including intact antibodies, for binding to a given epitope.

Immunologically functional immunoglobulin fragments include, but are not limited to, scFv fragments, Fab fragments (Fab', F(ab')2, and the like), one or more complementarity determining regions ("CDRs"), a diabody (heavy chain variable domain on the same polypeptide as a light chain variable domain, connected via a short peptide linker that is too short to permit pairing between the two domains on the same chain), domain antibodies, bivalent antigen binding domains (comprises two antigen binding sites), multispecific antigen binding domains, and single-chain antibodies. These fragments can be derived from any mammalian source, including but not limited to human, mouse, rat, camelid or rabbit. As will be appreciated by one of skill in the art, an antigen binding domain can include non-protein components.

The variable regions typically exhibit the same general structure of relatively conserved framework regions (FR) joined by the 3 hypervariable regions (CDRs). The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3.

In some embodiments, antigen binding domains comprise one or more complementarity binding regions (CDRs) present in the full-length light or heavy chain of an antibody, and in some embodiments comprise a single heavy chain and/or light chain or portion thereof. These fragments can be produced by recombinant DNA techniques or can be produced by enzymatic or chemical cleavage of antigen binding domains, including intact antibodies.

In some embodiments, the antigen binding domain is an antibody or fragment thereof, including one or more of the complementarity determining regions (CDRs) thereof. In some embodiments, the antigen binding domain is a single chain variable fragment (scFv), comprising light chain CDRs CDR1, CDR2 and CDR3, and heavy chain CDRs CDR1, CDR2 and CDR3.

The assignment of amino acids to each of the framework, CDR, and variable domains is typically in accordance with numbering schemes of Kabat numbering (see, e.g., Kabat et al. in Sequences of Proteins of Immunological Interest, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) J Mol Biol 273: 927-948; Chothia et al., (1992) J Mol Biol 227: 799-817; Tramontano et al., (1990) J Mol Biol 215(1): 175-82; and U.S. Pat. No. 7,709,226), contact numbering, or the AbM scheme (Antibody Modeling program, Oxford Molecular).

In some embodiments, the antigen binding domain is a recombinant antigen receptor. The term "recombinant antigen receptor" as used herein refers broadly to a non-naturally occurring surface receptor that comprises an extracellular antigen-binding domain or an extracellular ligand-binding domain, a transmembrane domain and an intracellular domain. In some embodiments, the recombinant antigen receptor is a chimeric antigen receptor (CAR). Chimeric antigen receptors (CARs) are well-known in the art. A CAR is a fusion protein that comprises an antigen recognition moiety, a transmembrane domain and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)).

In some embodiments, the intracellular domain of a recombinant antigen receptor comprises a co-stimulatory domain and an ITAM-containing domain. In some embodiments, the intracellular domain of a recombinant antigen receptor comprises an intracellular protein or a functional variant thereof (e.g., truncation(s), insertion(s), deletion(s) or substitution(s)).

The term "extracellular ligand-binding domain" or "extracellular antigen-binding domain" as used herein refers to a polypeptide that is capable of binding a ligand or an antigen or capable of interacting with a cell surface molecule, such as a ligand or a surface antigen. For example, the extracellular ligand-binding or antigen-binding domain may be chosen to recognize a ligand that acts as a cell surface marker on target cells associated with a particular disease state, e.g., a tumor-specific antigen. In some embodiments, the antigen-binding domain comprises an antibody, or an antigen binding fragment or an antigen binding portion of an antibody. In some embodiments, the antigen binding domain comprises an Fv or scFv, an Fab or scFab, an F(ab')2 or a scF(ab')2, an Fd, a monobody, a affibody, a camelid antibody, a VHH antibody, a single domain antibody, or a darpin. In some embodiments, the ligand-binding domain comprises a partner of a binding pair, such as a ligand that binds to a surface receptor, or an ectodomain of a surface receptor that binds to a ligand.

The term "stalk domain" or "hinge domain" are used interchangeably herein to refer to any polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

Vectors

Expression vectors and administration of polynucleotide compositions are further described herein.

In another aspect, the present disclosure provides a method of making any of the polynucleotides described herein.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof. Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:1 1-17; Robinson, E. D., 1971, Comb. Theor. 1 1:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/m\), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. an allele is any one of several forms of a gene occupying a given chromosomal locus. The instant disclosure encompasses alleles of the genes comprising the polynucleotide sequences provided herein. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratgene, and Invitrogen.

Expression vectors generally are replicable polynucleotide constructs that contain a polynucleotide according to the present disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a FasL protein, FasL derivative protein or an antigen binding protein e.g. a CAR disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, cause a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an imRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). Those skilled in the art will recognize that, in view of the degeneracy of the genetic code, considerable sequence variation is possible among these polynucleotide molecules. In some embodiments, nucleic acid sequences of the present disclosure are codon-optimized for expression in mammalian cells, preferably for expression in human cells. Codon-optimization refers to the exchange in a sequence of interest of codons that are generally rare in highly expressed genes of a given species for codons that are generally frequent in highly expressed genes of such species, such codons encoding the same amino acids as the codons that are being exchanged.

Methods of preparing immune cells for use in immunotherapy are provided herein. In some embodiments, the methods comprise introducing a FasL protein or FasL protein derivative and an antigen binding protein e.g. a CAR into immune cells, and expanding the cells. In some embodiments, the present disclosure relates to a method of engineering an immune cell comprising: providing a cell and expressing a FasL protein or FasL protein derivative, and expressing at the surface of the cell at least one antigen binding protein e.g. a CAR. In some embodiments, the method comprises: transfecting the cell with at least one polynucleotide encoding a FasL protein or FasL protein derivative, and at least one polynucleotide encoding an antigen binding protein e.g. a CAR, and expressing the polynucleotides in the cell. In some embodiments, the method further comprises: transfecting the cell with at least one polynucleotide encoding a FasL protein or FasL protein derivative, at least one polynucleotide encoding an antigen binding protein e.g. a CAR, and at least one polynucleotide encoding an NK cell antagonist, and expressing the polynucleotides in the cell.

In some embodiments, the polynucleotides encoding the FasL protein or FasL protein derivative and the antigen binding protein e.g. a CAR are present in one or more expression vectors for stable expression in the cells. In some embodiments, the polynucleotides are present in viral vectors for stable expression in the cells. In some embodiments, the viral vectors may be for example, lentiviral vectors or adenoviral vectors.

In some embodiments, polynucleotides encoding polypeptides according to the present disclosure can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Also provided herein are methods of transfecting an immune cell e.g. a T cell. In some embodiments, the method comprises: contacting a T cell with RNA and applying to the T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V per centimeter with a pulse width of about 100 ms and a pulse interval of about 100 ms between the electrical pulse of step (b) and the first electrical pulse of step (c); and (e) three electrical pulses with a voltage of about 1600 V with a pulse width of about 10 ms and a pulse interval of 2 ms between each of three electrical pulses. In some embodiments, a method of transfecting a T cell comprises contacting said T cell with RNA and applying to the T cell an agile pulse sequence comprising: (a) an electrical pulse with a voltage of about 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250 to 3000 V per centimeter, e.g. of 2250, 2300, 2350, 2400, 2450, 2500, 2550, 2400, 2450, 2500, 2600, 2700, 2800, 2900 or 3000V per centimeter with a pulse width of 100 ms and a pulse interval of 100 ms between the electrical pulse of step (b) and the first electrical pulse of step (c); and (e) 4 electrical pulses with a voltage of about 1600 V with a pulse width of about 10 ms and a pulse interval of about 2 ms between each of three electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, the method can further comprise a step of genetically modifying a cell by inactivating or reducing the expression level of at least one gene expressing, for example without limitation, FasR, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRa, TCRβ, β2-microglobulin (132m"), CD52, GR, deoxycytidine kinase (DCK), PD-1, and CTLA-4. In some embodiments the method comprises inactivating or reducing the expression level of one or more genes by introducing into the cells a rare-cutting endonu-clease able to selectively inactivate a gene by selective DNA cleavage. In some embodiments the rare-cutting endonu-clease can be, for example, a transcription activator-like effector nuclease (TALE-nuclease or TALEN), a megaTAL nuclease or a Cas9 endonuclease.

In another aspect, a step of genetically modifying immune cells e.g. T cells can comprise: modifying immune cells e.g. T cells by inactivating at least one gene expressing a target for an immunosuppressive agent, and; expanding the cells, optionally in the presence of the immunosuppressive agent. An immunosuppressive agent is an agent that suppresses immune function by one of several mechanisms of action. An immunosuppressive agent can diminish the extent and/or voracity of an immune response. Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immuno-suppressive antimetabolites. Some cytotoxic immunosup-pressants act by inhibiting DNA synthesis. Others may act through activation of T cells or by inhibiting the activation of helper cells. The methods according to the present dis-closure allow conferring immunosuppressive resistance to e.g., T cells for immunotherapy by inactivating the target of the immunosuppressive agent in the T cells. As non-limiting examples, targets for an immunosuppressive agent can be a receptor for an immunosuppressive agent such as for example without limitation CD52, glucocorticoid receptor (GR), FKBP family gene members, and cyclophilin family gene members.

In a further aspect, the disclosure provides an engineered immune cell comprising the polynucleotide or vector dis-closed herein.

Compositions and methods for expressing FasL protein or a FasL protein derivative in conjunction with downregula-tion of FasR cell surface expression are provide herein. Also provided are uses of such compositions and methods for improving the functional activities of immune cells e.g. T cells, such as CAR-T cells. The methods and compositions provided herein are useful for improving in vivo persistence and therapeutic efficacy of immune cells e.g. T cells such as CAR-T cells.

Immune cells e.g. T cells provided herein express: (i) a FasL protein and (ii) an antigen binding protein e.g. a chimeric antigen receptor (CAR). Advantageously, the immune cells provided herein exhibit improved in vivo persistence relative to cells that do not express the viral protein and/or increased resistance to AICD.

In various embodiments, the FasL protein consists of or comprises the amino acid sequence of, e.g., wild-type human FasL protein as described as "UniprotKB-P48023". Exemplary FasL protein and/or FasL protein derivatives consist of or comprise the amino sequence of UniprotKB-P48023 (SEQ ID NO:3), FasL delta 2-74 (SEQ ID NO:7), FasL Q130D (SEQ ID NO:10), FasL C82A (SEQ ID NO:8) and FasL SLEKQ126-130→EEAAA (SEQ ID NO:9) ("SLEKQ" and "EEAAA" disclosed as SEQ ID NOs: 32 and 33, respectively).

In certain embodiments, the FasL protein comprises an amino acid sequence which comprises at least 70%, for example at least 80%, or at least 90%, 95%, 97%, or 99% sequence identity with the amino acid sequence of FasL wild-type-UniprotKB-P48023. In certain embodiments, the FasL protein derivative comprises an amino acid sequence which comprises at least 70%, for example at least 80%, or at least 90%, 95%, 97%, or 99% sequence identity with the amino acid sequence of FasL Acyto (a.k.a. FasL delta 2-74), FasL C82A, FasL SLEKQ→EEAAA (SEQ ID NOs: 32 and 33, respectively) (i.e., FasL SLEKQ126-130→EEAAA (SEQ ID NOs: 32 and 33, respectively)), or FasL Q130D.

In certain embodiments, a nucleic acid of the present disclosure encodes a FasL protein that comprises an amino acid sequence which comprises at least 70%, for example at least 80%, or at least 90%, 95%, 97%, or 99% sequence identity with the amino acid sequence of FasL wild-type-UniprotKB-P48023. In certain embodiments, a nucleic acid of the present disclosure encodes a FasL protein derivative that comprises an amino acid sequence which comprises at least 70%, for example at least 80%, or at least 90%, 95%, 97%, or 99% sequence identity with the amino acid sequence of FasL Acyto (a.k.a. FasL delta 2-74), FasL C82A, FasL SLEKQ→EEAAA (SEQ ID NO: 32 and 33, respectively) (a.k.a. FasL SLEKQ126-130→EEAAA (SEQ ID NO: 32 and 33, respectively)), or FasL Q130D.

In some embodiments, an immune cell e.g., T cell pro-vided herein further is modified e.g., genetically modified to express FasR at a reduced level relative to a comparable cell that has not been so modified. For example, the immune cells can be genetically modified to knock out all or part of the FasR locus such that functional FasR is not expressed at the cell's surface, e.g., by deleting or disrupting genomic DNA that comprises the coding sequence of FasR and/or the genomic DNA that comprises the FasR transcriptional con-trol and/or promoter and/or activation elements.

In some embodiments, cell surface expression levels of FasR on immune cells e.g. T cells of the present disclosure may be decreased by at least about 30%, 35%, 40%, 45%, 50%, 55%, 60%, 65%, 70%, 75%, 80%, 85%, 90%, 95%, 99%, or 100% relative to cell surface expression levels on comparable cells not modified to reduce FasR expression. Surface FasR expression can be measured by binding of a fluorescently labeled anti-FasR/CD95 antibody and flow cytometry to determine mean fluorescence intensity on a per-cell basis across a population of cells. KO efficiency was roughly 50% with KO cells exhibiting 1-2 logs lower fluorescence intensity for FasR staining.

In some embodiments, an immune cell e.g., a T cell of the present disclosure, comprises e.g. expresses a polypeptide that consists of or comprises one or more amino acid sequence listed in Table 1.

TABLE 1

<u>Exemplary Protein Sequences</u>

| Polypeptide | Amino Acid Sequence | SEQ ID NO: |
|---|---|---|
| BFP | MSELIKENMHMKLYMEGTVDNHHFKCTSEGEGKPYEGTQ TMRIKVVEGGPLPFAFDILATSFLYGSKTFINHTQGIPDFFK QSFPEGFTWERVTTYEDGGVLTATQDTSLQDGCLIYNVKIR GVNFTSNGPVMQKKTLGWEAFTETLYPADGGLEGRNDMA LKLVGGSHLIANIKTTYRSKKPAKNLKMPGVYYVDYRLER IKEANNETYVEQHEVAVARYCDLPSKLGHKLN | 1 |
| P2A | GGSGGRAKRATNFSLLKQAGDVEENPGP | 2 |
| FasL wild-type-UniprotKB-P48023 | MQQPFNYPYPQIYWVDSSASSPWAPPGTVLPCPTSVPRRPG QRRPPPPPPPPPLPPPPPPPPLPPLPLPPLKKRGNHSTGLCLLV MFFMVLVALVGLGLGMFQLFHLQKELAELRESTSQMHTA SSLEKQIGHPSPPPEKKELRKVAHLTGKSNSRSMPLEWEDT YGIVLLSGVKYKKGGLVINETGLYFVYSKVYFRGQSCNNL PLSHKVYMRNSKYPQDLVMMEGKMMSYCTTGQMWARSS YLGAVFNLTSADHLYVNVSELSLVNFEESQTFFGLYKL | 3 |
| FasL cytoplasmic domain | MQQPFNYPYPQIYWVDSSASSPWAPPGTVLPCPTSVPRRPG QRRPPPPPPPPPLPPPPPPPPLPPLPLPPLKKRGNHSTG | 4 |
| FasL transmembrane domain | LCLLVMFFMVLVALVGLGLGMF | 5 |
| FasL TM ectodomain | QLFHLQKELAELRESTSQMHTASSLEKQIGHPSPPPEKKELR KVAHLTGKSNSRSMPLEWEDTYGIVLLSGVKYKKGGLVIN ETGLYFVYSKVYFRGQSCNNLPLSHKVYMRNSKYPQDLV MMEGKMMSYCTTGQMWARSSYLGAVFNLTSADHLYVNV SELSLVNFEESQTFFGLYKL | 6 |
| FasL Δcyto (a.k.a. FasL delta 2-74) | MGNHSTGLCLLVMFFMVLVALVGLGLGMFQLFHLQKELA ELRESTSQMHTASSLEKQIGHPSPPPEKKELRKVAHLTGKS NSRSMPLEWEDTYGIVLLSGVKYKKGGLVINETGLYFVYS KVYFRGQSCNNLPLSHKVYMRNSKYPQDLVMMEGKMMS YCTTGQMWARSSYLGAVFNLTSADHLYVNVSELSLVNFEE SQTFFGLYKL | 7 |
| FasL C82A | MQQPFNYPYPQIYWVDSSASSPWAPPGTVLPCPTSVPRRPG QRRPPPPPPPPPLPPPPPPPPLPPLPLPPLKKRGNHSTGLALLV MFFMVLVALVGLGLGMFQLFHLQKELAELRESTSQMHTA SSLEKQIGHPSPPPEKKELRKVAHLTGKSNSRSMPLEWEDT YGIVLLSGVKYKKGGLVINETGLYFVYSKVYFRGQSCNNL PLSHKVYMRNSKYPQDLVMMEGKMMSYCTTGQMWARSS YLGAVFNLTSADHLYVNVSELSLVNFEESQTFFGLYKL | 8 |
| FasL SLEKQ→EEAAA (SEQ ID NO: 32 and 33, respectively) (a.k.a. FasL SLEKQ126-130→ EEAAA (SEQ ID NO: 32 and 33, respectively)) | MQQPFNYPYPQIYWVDSSASSPWAPPGTVLPCPTSVPRRPG QRRPPPPPPPPPLPPPPPPPPLPPLPLPPLKKRGNHSTGLCLLV MFFMVLVALVGLGLGMFQLFHLQKELAELRESTSQMHTA SEEAAAIGHPSPPPEKKELRKVAHLTGKSNSRSMPLEWEDT YGIVLLSGVKYKKGGLVINETGLYFVYSKVYFRGQSCNNL PLSHKVYMRNSKYPQDLVMMEGKMMSYCTTGQMWARSS YLGAVFNLTSADHLYVNVSELSLVNFEESQTFFGLYKL | 9 |
| FasL Q130D | MQQPFNYPYPQIYWVDSSASSPWAPPGTVLPCPTSVPRRPG QRRPPPPPPPPPLPPPPPPPPLPPLPLPPLKKRGNHSTGLCLLV MFFMVLVALVGLGLGMFQLFHLQKELAELRESTSQMHTA SSLEKDIGHPSPPPEKKELRKVAHLTGKSNSRSMPLEWEDT YGIVLLSGVKYKKGGLVINETGLYFVYSKVYFRGQSCNNL PLSHKVYMRNSKYPQDLVMMEGKMMSYCTTGQMWARSS YLGAVFNLTSADHLYVNVSELSLVNFEESQTFFGLYKL | 10 |
| FasL F275L (inactive FasL) | MQQPFNYPYPQIYWVDSSASSPWAPPGTVLPCPTSVPRRPG QRRPPPPPPPPPLPPPPPPPPLPPLPLPPLKKRGNHSTGLCLLV MFFMVLVALVGLGLGMFQLFHLQKELAELRESTSQMHTA SSLEKQIGHPSPPPEKKELRKVAHLTGKSNSRSMPLEWEDT YGIVLLSGVKYKKGGLVINETGLYFVYSKVYFRGQSCNNL | 11 |

TABLE 1-continued

| | Exemplary Protein Sequences | |
| --- | --- | --- |
| Polypeptide | Amino Acid Sequence | SEQ ID NO: |
| | PLSHKVYMRNSKYPQDLVMMEGKMMSYCTTGQMWARSS YLGAVFNLTSADHLYVNVSELSLVNFEESQTLFGLYKL | |
| WPRE | NQPLDYKICERLTGILNYVAPFTLCGYAALMPLYHAIASRM AFIFSSLYKSWLLSLYEELWPVVRQRGVVCTVFADATPTG WGIATTCQLLSGTFAFPLPIATAELIAACLARCWTGARLLG TDNSVVLSGKLTSFPWLLACVATWILRGTSFCYVPSALNPA DLPSRGLLPALRPLPRLRLRPQTSRISLWAASPP | 12 |

TABLE 2

| | Exemplary nucleotide sequences | |
| --- | --- | --- |
| Name | Nucleic Acid Sequence | SEQ ID NO: |
| MND | TAGTCCAATTTGTTAAAGACAGGATATCAGTGGTCCAGG CTCTAGTTTTGACTCAACAATATCACCAGCTGAAGCCTAT AGAGTACGAGCCATAGATAAAATAAAAGATTTTATTTAG TCTCCAGAAAAAGGGGGGAATGAAAGACCCCACCTGTAG GTTTGGCAAGCTAGGATCAAGGTCAGGAACAGAGAAACA GGAGAATATGGGCCAAACAGGATATCTGTGGTAAGCAGT TCCTGCCCCGCTCAGGGCCAAGAACAGTTGGAACAGGAG AATATGGGCCAAACAGGATATCTGTGGTAAGCAGTTCCT GCCCCGCTCAGGGCCAAGAACAGATGGTCCCCAGATGCG GTCCCGCCCTCAGCAGTTTCTAGAGAACCATCAGATGTTT CCAGGGTGCCCCAAGGACCTGAAATGACCCTGTGCCTTA TTTGAACTAACCAATCAGTTCGCTTCTCGCTTCTGTTCGC GCGCTTCTGCTCCCCGAGCTCAATAAAAGAGCCCACAAC CCCTCACTCGGCGCGATC | 13 |
| BFP | atgagcgagctgattaaggagaacatgcacatgaagctgtacatggagggcaccgtggacaa ccatcacttcaagtgcacatccgagggcgaaggcaagccctacgagggcacccagaccatg agaatcaaggtggtcgagggcgggccctctcccttcgccttcgacatcctggctactagcttcct ctacggcagcaagaccttcatcaaccacacccagggcatccccgacttcttcaagcagtccttc cctgagggatcacatgggagagagtcaccacatacgaagacggggcgtgctgaccgctac ccaggacaccagcctccaggacggctgcctcatctacaacgtcaagatcagaggggtgaactt cacatccaacggccctgtgatgcagaagaaaacactcggctgggaggccttcaccgagacgc tgtaccccgctgacggcccctggaaggcagaaacgacatggccctgaagctcgtgggcgg gagccatctgatcgcaaacatcaagaccacatatgatccaagaaacccgctaagaacctcaa gatgcctggcgtctactatgtggactacagactggaaagaatcaaggaggccaacaacgaga cctacgtcgagcagcacgaggtggcagtggccagatactgcgacctccctagcaaactgggg cacaagcttaat | 14 |
| P2A | ggaggctccggcggccgcgcaaaacgtgcaacgaatttcagcctgctgaagcaggccgggg acgtcgaggagaatcccgggcca | 15 |
| FasL wild-type | atgcagcagcctttcaactatccttatcctcagatctattgggtcgattctagcgcctcttctccttg ggcaccaccagggactgtcttgccatgcccgactagcgtgccacggagaccaggccagcgt cgacctcccccacctccacccccccctccctgccaccaccacccccaccacctcccttcca cccttgccacttcctccgcttaagaaacggggaaaccacagcactggctcctctgcctgttcat gttcttcatggtgctggttgcactggtgggactgggattggggatgttccagctgttccacttgca gaaggagttggcagaactgagggaaagcactagccagatgcacaccgcctcaagcttggag aagcagatcggtcacccaagcccccccccagaaaagaaggagctgaggaaggtcgcacac ctcaccggtaaatccaattcccggtcaatgcccctggagtgggaagacaccatggcatcgttct gctttcaggcgtcaaatacaagaaaggagggctggttatcaatgaaacagggctgtatttcgttt attccaaggtctactttcggggggcagtcctgtaacaatctccctctcagccacaaagtctacatga ggaacagcaaataccccaggatctggttatgatggaaggggaagatgatgagctactgcacta ccggccagatgtgggccaggagttcctacctgggtgccgtcttcaaccttacttccgcagacca tctgtacgtcaacgtgagtgaactgtccctggtgaactttgaggagagtcagacctttttcgggct gtataaactg | 16 |
| FasL cytoplasmic domain | atgcagcagcctttcaactatccttatcctcagatctattgggtcgattctagcgcctcttctccttg ggcaccaccagggactgtcttgccatgcccgactagcgtgccacggagaccaggccagcgt cgacctcccccacctccacccccccctccctgccaccaccacccccaccacctcccttcca cccttgccacttcctccgcttaagaaacggggaaaccacagcactggc | 17 |
| FasL trans-membrane domain | ctctgcctgttggtcatgttcttcatggtgctggttgcactggtgggactgggattggggatgttc | 18 |

TABLE 2-continued

Exemplary nucleotide sequences

| Name | Nucleic Acid Sequence | SEQ ID NO: |
|---|---|---|
| FasL TM ectodomain | cagctgttccacttgcagaaggagttggcagaactgagggaaagcactagccagatgcacac cgcctcaagcttggagaagcagatcggtcacccaagcccccccccagaaaagaaggagctg aggaaggtcgcacacctcaccggtaaatccaattcccggtcaatgcccctggagtgggaaga cacctatggcatcgttctgctttcaggcgtcaaatacaagaaaggagggctggttatcaatgaaa cagggctgtatttcgtttattccaaggtctactttcggggggcagtcctgtaacaatctccctctcag ccacaaagtctacatgaggaacagcaaataccccccaggatctggttatgatggaagggaagat gatgagctactgcactaccggccagatgtgggccaggagttcctacctgggtgccgtcttcaac cttacttccgcagaccatctgtacgtcaacgtgagtgaactgtccctggtgaactttgaggagag tcagacctttttcgggctgtatataaactg | 19 |
| FasL Acyto | atgggcaaccacagcaccggcctgtgcctgctggtgatgttcttcatggtgctggtggccctgg tgggcctgggcctgggcatgttccagctgttccacctgcagaaggagctggcgagctgaga gagagcaccagccagatgcacaccgccagcagcctggagaagcagatcggccacccccagc ccccccccgagaagaaggagctgagaaaggtggcccacctgaccggcagagcaacagc agaagcatgcccctggagtgggaggacacctacggcatcgtgctgctgagcggcgtgaagta caagaagggcggcctggtgatcaacgagaccgggcctgtacttcgtgtacagcaaggtgactt cagaggccagagctgcaacaacctgcccctgagccacaaggtgtacatgagaaacagcaag tacccccaggacctggtgatgatggagggcaagatgatgagctactgcaccaccggccagat gtgggccagaagcagctacctgggcgccgtgttcaacctgaccagcgccgaccacctgtacg tgaacgtgagcgagctgagcctggtgaacttcgaggagagccagaccttcttcggcctgtaca agctg | 20 |
| FasL C82A | atgcagcagcctttcaactatccttatcctcagatctattgggtcgattctagcgcctcttctccttg ggcaccaccagggactgtcttgccatgcccgactagcgtgccacggagaccaggccagcgt cgacctccccacctccaccccccccctccctgccaccaccaccccaccacctcccccttcca cccttgccacttcctccgcttaagaaacggggaaaccacagcactggcctcgccctgttggtca tgttcttcatggtgctggttgcactggtggggactgggattggggatgttccagctgttccacttgca gaaggagttggcagaactgagggaaagcactagccagatgcacaccgcctcaagcttggag aagcagatcggtcacccaagcccccccccagaaaagaaggagctgaggaaggtcgcacac ctcaccggtaaatccaattcccggtcaatgcccctggagtgggaagacacctatggcatcgttct gattcaggcgtcaaatacaagaaaggagggctggttatcaatgaaacagggctgtatttcgttt attccaaggtctactttcggggggcagtcctgtaacaatctccctctcagccacaaagtctacatga ggaacagcaaataccccccaggatctggttatgatggaagggaagatgatgagctactgcacta ccggccagatgtgggccaggagttcctacctgggtgccgtcttcaaccttacttccgcagacca tctgtacgtcaacgtgagtgaactgtccctggtgaactttgaggagagtcagacctttttcgggct gtataaactg | 21 |
| FasL SLEKQ→ EEAAA (SEQ ID NO: 32 and 33, respectively) | atgcagcagcctttcaactatccttatcctcagatctattgggtcgattctagcgcctcttctccttg ggcaccaccagggactgtcttgccatgcccgactagcgtgccacggagaccaggccagcgt cgacctccccacctccaccccccccctccctgccaccaccaccccaccacctcccccttcca cccttgccacttcctccgcttaagaaacggggaaaccacagcactggcctcgcctctgcctggtcat gttcttcatggtgctggttgcactggtggggactgggattggggatgttccagctgttccacttgca gaaggagttggcagaactgagggaaagcactagccagatgcacaccgcctcagaggaagcc gctgccatcggtcacccaagcccccccccagaaaagaaggagctgaggaaggtcgcacacc tcaccggtaaatccaattcccggtcaatgcccctggagtgggaagacacctatggcatcgttct gctttcaggcgtcaaatacaagaaaggagggctggttatcaatgaaacagggctgtatttcgttt attccaaggtctactttcggggggcagtcctgtaacaatctccctctcagccacaaagtctacatga ggaacagcaaataccccccaggatctggttatgatggaagggaagatgatgagctactgcacta ccggccagatgtgggccaggagttcctacctgggtgccgtcttcaaccttacttccgcagacca tctgtacgtcaacgtgagtgaactgtccctggtgaactttgaggagagtcagacctttttcgggct gtataaactg | 22 |
| FasL Q130D | atgcagcagcctttcaactatccttatcctcagatctattgggtcgattctagcgcctcttctccttg ggcaccaccagggactgtcttgccatgcccgactagcgtgccacggagaccaggccagcgt cgacctccccacctccaccccccccctccctgccaccaccaccccaccacctcccccttcca cccttgccacttcctccgcttaagaaacggggaaaccacagcactggcctctgcctgttggtcat gttcttcatggtgctggttgcactggtggggactgggattggggatgttccagctgttccacttgca gaaggagttggcagaactgagggaaagcactagccagatgcacaccgcctcaagcttggag aaggacatcggtcacccaagcccccccccagaaaagaaggagctgaggaaggtcgcacac ctcaccggtaaatccaattcccggtcaatgcccctggagtgggaagacacctatggcatcgttct gctttcaggcgtcaaatacaagaaaggagggctggttatcaatgaaacagggctgtatttcgttt attccaaggtctactttcggggggcagtcctgtaacaatctccctctcagccacaaagtctacatga ggaacagcaaataccccccaggatctggttatgatggaagggaagatgatgagctactgcacta ccggccagatgtgggccaggagttcctacctgggtgccgtcttcaaccttacttccgcagacca tctgtacgtcaacgtgagtgaactgtccctggtgaactttgaggagagtcagacctttttcgggct gtataaactg | 23 |
| FasL F275L | atgcagcagcctttcaactatccttatcctcagatctattgggtcgattctagcgcctcttctccttg ggcaccaccagggactgtcttgccatgcccgactagcgtgccacggagaccaggccagcgt cgacctccccacctccaccccccccctccctgccaccaccaccccaccacctcccccttcca cccttgccacttcctccgcttaagaaacggggaaaccacagcactggcctctgcctgttggtcat gttcttcatggtgctggttgcactggtggggactgggattggggatgttccagctgttccacttgca gaaggagttggcagaactgagggaaagcactagccagatgcacaccgcctcaagcttggag aagcagatcggtcacccaagcccccccccagaaaagaaggagctgaggaaggtcgcacac ctcaccggtaaatccaattcccggtcaatgcccctggagtgggaagacacctatggcatcgttct | 34 |

TABLE 2-continued

Exemplary nucleotide sequences

| Name | Nucleic Acid Sequence | SEQ ID NO: |
|---|---|---|
| | gctttcaggcgtcaaatacaagaaaggagggctggttatcaatgaaacagggctgtatttcgttt attccaaggtctactttcggggggcagtcctgtaacaatctccctctcagccacaaagtctacatga ggaacagcaaatacccccaggatctggttatgatggaaggggaagatgatgagctactgcacta ccggccagatgtgggccaggagttcctacctgggtgccgtcttcaaccttacttccgcagacca tctgtacgtcaacgtgagtgaactgtccctggtgaactttgaggagagtcagaccctgttcgggc tgtataaactg | |
| WPRE | aatcaacctctggattacaaaatttgtgaaagattgactggtattcttaactatgttgctccttttacg ctatgtggatacgctgattaatgcattgtatcatgctattgatcccgtatggctttcattttctcctc cttgtataaatcctggttgctgtctctttatgaggagttgtggcccgttgtcaggcaacgtggcgtg gtgtgcactgtgtttgctgacgcaacccccactggttggggcattgccaccacctgtcagctcct ttccgggactttcgctttccccctccctattgccacggcggaactcatcgccgcctgccttgccc gctgctggacaggggctcggctgttgggcactgacaattccgtggtgttgtcggggaagctga cgtcctttccatggctgctcgcctgtgttgccacctggattctgcgcgggacgtccttctgctacg tcccttcggccctcaatccagcggaccttccttcccgcggcctgctgccggctctgcggcctctt ccgcgtcttcgccttcgccctcagacgagtcggatctccctttgggccgcctccccgcctg | 24 |
| GlyGly Ser GlyGly-linked furin cleavage site ("GlyGly SerGlyGly" disclosed as SEQ ID NO: 35) | ggaggctccggcggccgcgcaaaacgt | 25 |
| 0673-V pLVX-MND-BFP-P2A-FasL_WPRE_updated_codopt_20191205 | tggaagggctaattcactcccaaagaagacaagatatccttgatctgtggatctaccacacacaa ggctacttccctgattagcagaactacacaccagggccaggggtcagatatccactgacctttg gatggtgctacaagctagtaccagttgagccagataaggtagaagaggccaataaaggagag aacaccagcttgttacaccctgtgagcctgcatgggatggatgacccggagagagaagtgtta gagtggaggfttgacagccgcctagcatttcatcacgtggcccggagctgcatccggagtact tcaagaactgctgatatcgagcttgctacaagggactttccgctggggactttccagggaggcg tggcctgggcgggactggggagtggcgagccctcagatcctgcatataagcagctgctttttgc ctgtactgggtctctctggttagaccagatctgagcctgggagctctctggctaactagggaacc cactgcttaagcctcaataaagcttgccttgagtgcttcaagtagtgtgtgcccgtctgttgtgtga ctctggtaactagagatccctcagaccccttttagtcagtgtggaaaatctctagcagtggcgccc gaacagggacttgaaagcgaaagggaaaccagaggagctctctcgacgcaggactcggctt gctgaagcgcgcacggcaagaggcgaggggcggcgactggtgagtacgccaaaaattttga ctagcggaggctagaaggagagagatgtgggtgcgagagcgtcagtattaagcggggggagaat tagatcgcgatgggaaaaaattcggttaaggccagggggaaagaaaaaatataaattaaaaca tatagtatgggcaagcagggagctagaacgattcgcagttaatcctggcctgttagaaacatca gaaggctgtagacaaatactgggacagctacaaccatcccttcagacaggatcagaagaactt agatcattatataatacagtagcaaccctctattgtgtgcatcaaaggatagagataaaagacac caaggaagctttagacaagatagaggaagagcaaaacaaaagtaagaccaccgcacagcaa gcggccggccgctgatcttcagacctggaggaggagatatgagggacaattggagaagtgaa ttatataaatataaagtagtaaaaattgaaccattaggagtagcacccaccaaggcaaagagaa gagtggtgcagagagaaaaaagagcagtgggaataggagattgttccttgggttatgggag cagcaggaagcactatgggcgcagcgtcaatgacgctgacggtacaggccagacaattattgt ctggtatagtgcagcagcagaacaatttgctgagggctattgaggcgcaacagcatctgttgca actcacagtctggggcatcaagcagctccaggcaagaatcctggctgtggaaagatacctaaa ggatcaacagctcctggggatttggggttgctctggaaaactcatttgcaccactgctgtgccttg gaatgctagttggagtaataaatctctggaacagatttggaatcacacgacctggatggagtgg gacagagaaattaacaattacacaagcttaatacactccttaattgaagaatcgcaaaaccagca agaaaagaatgaacaagaattattggaattagataaatgggcaagtttgtggaattggtttaacat aacaaattggctgtggtatataaaattattcataatgatagtaggaggcttggtaggtttaagaata gttttgctgtactttctatagtgaatagagttaggcagggatattattcaccattatcgtttcagaccca cctcccaaccccgaggggacccgacaggcccgaaggaatagaagaagaaggtggagaga gagacagagacagatccattcgattagtgaacggatctcgacggtatcgcctttaaaagaaaag gggggattgggggtacagtgcaggggaaagaatagtagacataatagcaacagacataca aactaaagaattacaaaaacaaattacaaaaattcaaaattttcgggtttattacagggacagcag agatccagtttatcgatTAGTCCAATTGTTAAAGACAGGATATCAG TGGTCCAGGCTCTAGTTTTGACTCAACAATATCACCAGCT GAAGCCTATAGAGTACGAGCCATAGATAAAATAAAAGAT TTTATTTAGTCTCCAGAAAAAGGGGGGAATGAAAGACCC CACCTGTAGGTTTGGCAAGCTAGGATCAAGGTCAGGAAC AGAGAAACAGGAGAATATGGGCCAAACAGGATATCTGTG GTAAGCAGTTCCTGCCCCGCTCAGGGCCAAGAACAGTTG GAACAGGAGAATATGGGCCAAACAGGATATCTGTGGTAA GCAGTTCCTGCCCCGCTCAGGGCCAAGAACAGATGGTCC CCAGATGCGGTCCCGCCCTCAGCAGTTTCTAGAGAACCAT CAGATGTTTCCAGGGTGCCCCAAGGACCTGAAATGACCC TGTGCCTTATTTGAACTAACCAATCAGTTCGCTTCTCGCTT CTGTTCGCGCGCTTCTGCTCCCCGAGCTCAATAAAAGAGC | 26 |

TABLE 2-continued

Exemplary nucleotide sequences

| Name | Nucleic Acid Sequence | SEQ ID NO: |
|---|---|---|
| | CCACAACCCCTCACTCGGCGCGATCggatctatttccggtgaattccgcc<br>accatgagcgagctgattaaggagaacatgcacatgaagctgtacatggagggcaccgtgga<br>caaccatcacttcaagtgcacatccgagggcgaaggcaagccctacgagggcacccagacc<br>atgagaatcaaggtggtcgagggcggccctctcccttcgccttcgacatcctggctactagctt<br>cctctacggcagcaagaccttcatcaaccacacccagggcatccccgacttcttcaagcagtcc<br>ttccctgagggcttcacatgggagagagtcaccacatacgaagacgggggcgtgctgaccgc<br>tacccaggacaccagcctccaggacggctgcctcatctacaacgtcaagatcagaggggtga<br>acttcacatccaacggccctgtgatgcagaagaaaacactcggctgggaggccttcaccgaga<br>cgctgtaccccgctgacggcggcctggaaggcagaaacgacatggccctgaagctcgtgggg<br>cggggagccatctgatcgcaaacatcaagaccacatatagatccaagaaacccgctaagaacct<br>caagatgcctggcgtctactatgtggactacagactggaaagaatcaaggaggccaacaacg<br>agacctacgtcgagcagcacgaggtggcagtggccagatactgcgacctccctagcaaactg<br>gggcacaagcttaatggaggctccggcggccgcgcaaaacgtgcaacgaatttcagcctgct<br>gaagcaggccggggacgtcgaggagaatcccgggccaatgcagcagcctttcaactatcctt<br>atcctcagatctattgggtcgattctagcgcctcttctccttgggcaccaccagggactgtcttgc<br>catgcccgactagcgtgccacggagaccaggccagcgtcgacctcccccacctccacccc<br>ccctcccctgccaccaccacccccaccacctcccccttccacccttgccacttcctccgcttaaga<br>aacgggggaaaccacagcactggcctctgcctgttggtcatgttcttcatggtgctggttgcactg<br>gtgggactgggattgggatgttccagctgttccacttgcagaaggagttggcagaactgagg<br>gaaagcactagccagatgcacaccgcctcaagcttggagaagcagatcggtcacccaagccc<br>cccccagaaaagaaggagctgaggaaggtcgcacacctcaccggtaaatccaattcccggt<br>caatgcccctggagtgggaagacacctatggcatcgttctgctttcaggcgtcaaatacaagaa<br>aggagggctggttatcaatgaaacagggctgtatttcgtttattccaaggtctactttcggggggca<br>gtcctgtaacaatctccctctcagccacaaagtctacatgaggaacagcaaataccccccaggat<br>ctggttatgatggaagggaagatgatgagctactgcactaccggccagatgtgggccaggagt<br>tcctacctgggtgccgtcttcaaccttacttccgcagaccatctgtacgtcaacgtgagtgaactg<br>tccctggtgaactttgaggagagtcagacctttttcgggctgtataaaactgtgataggcgcgcc<br>acgcgtctggaacaatcaacctctggattacaaaatttgtgaaagattgactggtattcttaactat<br>gttgctccttttacgctatgtggatacgctgctttaatgccttgtatcatgctattgcttccgtatgg<br>ctttcattttctcctccttgtataaatcctggttgctgtctctttatgaggagttgtggcccgttgtcag<br>gcaacgtggcgtggtgtgcactgtgtttgctgacgcaaccccactggttggggcattgccacc<br>acctgtcagctcctttccgggactttcgctttccccctccctattgccacggcggaactcatcgcc<br>gcctgccttgcccgctgctgacagggggctcggctgttgggcactgacaattccgtggtgttgt<br>cggggaagctgacgtccttccatggctgctcgcctgtgttgccacctggattctgcgcgggac<br>gtccttctgctacgtcccttcggccctcaatccagcggaccttccttcccgcggcctgctgccgg<br>ctctgcgggcctcttccgcgtcttcgccttcgccctcagacgagtcggatctcccctttgggccgcct<br>ccccgcctggaattaattctgcagtcgagacctagaaaaacatggagcaatcacaagtagcaat<br>acagcagctaccaatgctgattgtgcctggctagaagcacaaggaggaggaggaggtgggtttt<br>ccagtcacacctcaggtacctttaagaccaatgacttacaaggcagctgtagatcttagccacttt<br>ttaaaagaaaagaggggggactggaagggctaattcactcccaacgaagacaagatatccttgat<br>ctgtggatctaccacacacaaggctacttccctgattagcagaactacacaccagggccaagg<br>gtcagatatccactgacctttggatggtgctacaagctagtaccagttgagccagataaggtaga<br>agaggccaataaaggagagaacaccagcttgttacaccctgtgagcctgcatgggatggatga<br>cccggagagagaagtgttagagtggaggtttgacagccgcctagcatttcatcacgtggcccg<br>agagctgcatccggagtacttcaagaactgctgatatcgagcttgctacaagggactttccgctg<br>gggactttccaggggaggcgtggcctgggcgggactggggagtggcgagccctcagatcctg<br>catataagcagctgcttttttgcctgtactgggtctctctggttagaccagatctgagcctgggagc<br>tctctggctaactagggaacccactgcttaagcctcaataaagcttgccttgagtgcttcaagtag<br>tgtgtgcccgtctgttgtgtgactctggtaactagagatccctcagacccctttttagtcagtgtggaa<br>aatctctagcagtagtagttcatgtcatcttattattcagtatttataacttgcaaagaaatgaatatc<br>agagagtgagaggccttgacattgctagcgtttaccgtcgacctctagctagagcttggcgtaat<br>catggtcatagctgtttcctgtgtgaaattgttatccgctcacaattccacacaacatacgagccg<br>gaagcataaagtgtaaagcctggggtgcctaatgagtgagctaactcacattaattgcgttgcgc<br>tcactgcccgctttccagtcgggaaacctgtcgtgccagctgcattaatgaatcggccaacgcg<br>cggggagaggcggtttgcgtattgggcgctcttccgcttcctcgctcactgactcgctgcgctc<br>ggtcgttcggctgcggcgagcggtatcagctcactcaaaggcggtaatacggttatccacaga<br>atcaggggataacgcaggaaagaacatgtgagcaaaaggccagcaaaaggccaggaaccg<br>taaaaaggccgcgttgctggcgtttttccataggctccgcccccctgacgagcatcacaaaaat<br>cgacgctcaagtcagaggtggcgaaacccgacaggactataaagataccaggcgtttcccct<br>ggaagctccctcgtgcgctctcctgttccgaccctgccgcttaccggatacctgtccgcctttctc<br>ccttcgggaagcgtggcgctttctcatagctcacgctgtaggtatctcagttcggtgtaggtcgtt<br>cgctccaagctgggctgtgtgcacgaaccccccgttcagcccgaccgctgcgccttatccggt<br>aactatcgtcttgagtccaacccggtaagacacgacttatcgccactggcagcagccactggta<br>acaggattagcagagcgaggtatgtaggcggtgctacagagttcttgaagtggtggcctaacta<br>cggctacactagaagaacagtatttggtatctgcgctctgctgaagccagttaccttcggaaaaa<br>gagttggtagctcttgatccggcaaacaaaccaccgctggtagcggtggtttttttgtttgcaagc<br>agcagattacgcgcagaaaaaaaggatctcaagaagatcctttgatcttttctacggggtctgac<br>gctcagtggaacgaaaactcacgttaagggattttggtcatgagattatcaaaaaggatcttcac<br>ctagatccttttaaattaaaaatgaagttttaaatcaatctaaagtatatatgagtaaacttggtctga<br>cagttaccaatgcttaatcagtgaggcacctatctcagcgatctgtctatttcgttcatccatagttg<br>cctgactccccgtcgtgtagataactacgatacgggagggcttaccatctggccccagtgctgc<br>aatgataccgcgagacccacgctcaccggctccagatttatcagcaataaaccagccagccgg<br>aagggccgagcgcagaagtggtcctgcaactttatccgcctccatccagtctattaattgttgcc<br>gggaagctagagtaagtagttcgccagttaatagtttgcgcaacgttgttgccattgctacaggc<br>atcgtggtgtcacgctcgtcgtttggtatggcttcattcagctccggttcccaacgatcaaggcga | |

TABLE 2-continued

Exemplary nucleotide sequences

| Name | Nucleic Acid Sequence | SEQ ID NO: |
|---|---|---|
| | gttacatgatcccccatgttgtgcaaaaaagcggttagctccttcggtcctccgatcgttgtcaga agtaagttggccgcagtgttatcactcatggttatggcagcactgcataattctcttactgtcatgc catccgtaagatgcttttctgtgactggtgagtactcaaccaagtcattctgagaatagtgtatgcg gcgaccgagttgctcttgcccggcgtcaatacgggataataccgcgccacatagcagaacttta aaagtgctcatcattggaaaacgttcttcggggcgaaaactctcaaggatcttaccgctgttgag atccagttcgatgtaacccactcgtgcacccaactgatcttcagcatcttttactttcaccagcgttt ctgggtgagcaaaaacaggaaggcaaaatgccgcaaaaaagggaataagggcgacacgga aatgttgaatactcatactcttcctttttcaatattattgaagcatttatcagggttattgtctcatga gcggatacatatttgaatgtatttagaaaaataaacaaataggggttccgcgcacatttccccgaaa gtgccacctgacgtcgacggatcgggagatcaacttgtttattgcagcttataatggttacaaata aagcaatagcatcacaaatttcacaaataaagcattttttttcactgcattctagttgtggtttgtccaa actcatcaatgtatcttatcatgtctggatcaaactggataactcaagctaaccaaaatcatcccaaa cttcccaccccatacctattaccactgccaattacctgtggtttcatttactctaaacctgtgattcc tctgaattattttcattttaaagaaattgtatttgttaaatatgtactacaaacttagtagt | |
| 0674-V pLVX- MND- BFP-P2A- FasL_F275L_ WPRE_ updated_ codopt_ 20191205 | tggaagggctaattcactcccaaagaagacaagatatccttgatctgtggatctaccacacacaa ggctacttccctgattagcagaactacacaccagggccaggggtcagatatccactgacctttg gatggtgctacaagctagtaccagttgagccagataaggtagaagaggccaataaaggagag aacaccagcttgttacaccctgtgagcctgcatgggatggatgacccggagagagaagtgtta gagtggaggtttgacagccgcctagcattcatcacgtggcccgagagctgcatccggagtact tcaagaactgctgatatcgagcttgctacaagggactttccgctggggactttccaggggaggcg tggcctgggcggggactggggagtggcgagccctcagatcctgcatataagcagctgctttttgc ctgtactgggtctctctggttagaccagatctgagcctgggagctctctggctaactagggaacc cactgcttaagcctcaataaaagcttgccttgagtgcttcaagtagtgtgtgcccgtctgttgtgtga ctctggtaactagagatccctcagacccttttagtcagtgtggaaaatctctagcagtggcgccc gaacagggacttgaaagcgaaagggaaaccagaggagctctctcgacgcaggactcggctt gctgaagcgcgcacggcaagaggcgaggggcggcgactggtgagtacgccaaaaattttga ctagcggaggctagaaggagagagatgggtgcgagagcgtcagtattaagcggggggagaat tagatcgcgatgggaaaaattcggttaaggccaggggaaagaaaaaatataaattaaaaca tatagtatgggcaagcagggagctagaacgattcgcagttaatcctggcctgttagaaacatca gaaggctgtagacaaatactgggacagctacaaccatcccttcagacaggatcagaagaactt agatcattatataatacagtagcaacccctctattgtgtgcatcaaaggatagagataaaagacac caaggaagcttagacaagatagaggaagagcaaaacaaaagtaagaccaccgcacagcaa gcggccgccgctgatcttcagacctggaggaggagatatgagggacaattggagaagtgaa ttatataaatataaagtagtaaaaattgaaccattaggagtagcacccaccaaggcaaagagaa gagtggtgcagagagaaaaaagagcagtgggaataggagctttgttccttgggttcttgggag cagcaggaagcactatgggcgcagcgtcaatgacgctgacggtacaggccagacaattattgt ctggtatagtgcagcagcagaacaatttgctgagggctattgaggcgcaacagcatctgttgca actcacagtctggggcatcaagcagctccaggcaagaatcctggctgtggaaagatacctaaa ggatcaacagctcctggggatttggggttgctctggaaaactcatttgcaccactgctgtgccttg gaatgctagttggagtaataaatctctggaacagatttggaatcacacgacctggatggagtgg gacagagaaattaacaattacacaagcttaatacactccttaattgaagaatcgcaaaaccagca agaaaagaatgaacaagaattattggaattagataaatgggcaagtttgtggaattggtttaacat aacaaattggctgtggtatataaaattattcataatgatagtaggaggcttggtaggtttaagaata gttttgctgtactttctatagtgaatagagttaggcagggatattcaccattatcgtttcagaccca cctcccaaccccgaggggacccgacaggcccgaaggaatagaagaagaaggtggagaga gagacagagacagatccattcgattagtgaacggatctcgacggtatcgcctttaaaagaaaag gggggattggggggtacagtgcaggggaaagaatagtagacataatagcaacagacataca aactaaagaattacaaaaacaaattacaaaaattcaaaattttcgggtttattacagggacagcag agatccagtttatcgatTAGTCCAATTTGTTAAAGACAGGATATCAG TGGTCCAGGCTCTAGTTTTGACTCAACAATATCACCAGCT GAAGCCTATAGAGTACGAGCCATAGATAAAATAAAAGAT TTTATTTAGTCTCCAGAAAAAGGGGGGAATGAAAGACCC CACCTGTAGGTTTGGCAAGCTAGGATCAAGGTCAGGAAC AGAGAAACAGGAGAATATGGGCCAAACAGGATATCTGTG GTAAGCAGTTCCTGCCCCGCTCAGGGCCAAGAACAGTTG GAACAGGAGAATATGGGCCAAACAGGATATCTGTGGTAA GCAGTTCCTGCCCCGCTCAGGGCCAAGAACAGATGGTCC CCAGATGCGGTCCCGCCCTCAGCAGTTTCTAGAGAACCAT CAGATGTTTCCAGGGTGCCCCAAGGACCTGAAATGACCC TGTGCCTTATTTGAACTAACCAATCAGTTCGCTTCTCGCTT CTGTTCGCGCGCTTCTGCTCCCCGAGCTCAATAAAAGAGC CCACAACCCCTCACTCGGCGCGATCggatctatttccggtgaattccgcc accatgagcgagctgattaaggagaacatgcacatgaagctgtacatggagggcaccgtgga caaccatcacttcaagtgcacatccgagggcgaaggcaagcccctacgagggcacccagacc atgagaatcaaggtggtcgagggcggcccctctcccctttcgaccatcctggctactagctt cctctacggcagcaagaccttcatcaaccacacccagggcatccccgacttcttcaagcagtcc ttccctgagggcttcacatgggagagagtcaccacatacgaagacgggggcgtgctgaccgc tacccaggacaccagcctccaggacggctgcctcatctacaacgtcaagatcagagggggtga acttcacatccaacggccctgtgatgcagaagaaaactctgggaaggcccttcaccggaga cgctgtaccccgctgacggcggcctggaaggcagaaacgacatggccctgaagctcgtggg cggggagccatctgatcgcaaacatcaagaccacatatagatccaagaaacccgctaagaacct caagatgcctggcgtctactatgtggactacagactggaaagaatcaaggaggccaacaacg agacctacgtcgagcagcacgaggtggcagtggccagatactgcgacctccctagcaaactg gggcacaagcttaatggaggctccggcggccgcgcaaaacgtgcaacgaatttcagcctgct | 27 |

TABLE 2-continued

Exemplary nucleotide sequences

| Name | Nucleic Acid Sequence | SEQ ID NO: |
|------|----------------------|------------|

```
gaagcaggccggggacgtcgaggagaatcccgggccaatgcagcagcctttcaactatcctt
atcctcagatctattgggtcgattctagcgcctcttctccttgggcaccaccagggactgtcttgc
catgcccgactagcgtgccacggagaccaggccagcgtcgacctcccccacctccacccccc
ccctcccctgccaccaccacccccaccacctccccttccacccttgccacttcctccgcttaaga
aacgggggaaaccacagcactggcctctgcctgttggtcatgttcttcatggtgctggttgcactg
gtgggactgggattgggatgttccagctgttccacttgcagaaggagttggcagaactgagg
gaaagcactagccagatgcacaccgcctcaagcttggagaagcagatcggtcacccaagccc
cccccagaaaagaaggagctgaggaaggtcgcacacctcaccggtaaatccaattcccggt
caatgcccctggagtgggaagacacctatggcatcgttctgctttcaggcgtcaaatacaagaa
aggagggctggttatcaatgaaacagggctgtatttcgtttattccaaggtctactttcgggggca
gtcctgtaacaatctccctctcagccacaaagtctacatgaggaacagcaaataccccccaggat
ctggttatgatggaagggaagatgatgagctactgcactactgcactacgacatgtgggccaggagt
tcctacctgggtgccgtatcaaccttacttccgcagaccatctgtacgtcaacgtgagtgaactg
tccctggtgaactttgaggagagtcagaccctgttcgggctgtataaaactgtgatagggcgcgc
cacgcgtctggaacaatcaacctctggattacaaaatttgtgaaagattgactggtattcttaacta
tgttgctccttttacgctatgtggatacgctgcttttaatgcctttgtatcatcgctattgcttcccgtatg
gctttcatttctcctccttgtataaatcctggttgctgtctctttatgaggagttgtgggccgttgtca
ggcaacgtggcgtggtgtgcactgtgtttgctgacgcaaccccccactggttggggcattgccac
cacctgtcagctcctttccgggactttcgctttcccccctcccattgccacggcggaactcatcgc
cgcctgccttgcccgctgctggacaggggctcggctgttgggcactgacaattccgtggtgttg
tcggggaagctgacgtcctttccatggctgctcgcctgtgttgccacctggattctgcgcgggac
gtccttctgctacgtcccttcggccctcaatccagcggaccttccttcccgcggcctgctgccgg
ctctgcggcctcttccgcgtcttcgccttcgccctcagacgagtcggatctcccctttgggccgcct
ccccgcctggaattaattctgcagtcgagacctagaaaaacatggagcaatcacaagtagcaat
acagcagctaccaatgctgattgtgcctggctagaagcacaagaggaggaggaggtgggtttt
ccagtcacacctcaggtacctttaagaccaatgacttacaaggcagctgtagatcttagccacttt
ttaaaagaaaagaggggactggaagggctaattcactcccaacgaagacaagatatccttgat
ctgtggatctaccacacacaaggctacttccctgattagcagaactacacaccagggccaggg
gtcagatatccactgacctttggatggtgctacaagctagtaccagttgagccagataaggtaga
agaggccaataaaggagagaacaccagcttgttacaccctgtgagcctgcatgggatggatga
cccggagagagaagtgttagagtggaggtttgacagccgcctagcatttcatcacgtggcccg
agagctgcatccggagtacttcaagaactgctgatatcgagcttgctacaagggactttccgctg
gggactttccagggaggcgtggcctgggcgggactggggagtggcgagccctcagatcctg
catataagcagctgcttttttgcctgtactgggtctctctggttagaccagatctgagcctgggagc
tctctggctaactagggaacccactgcttaagcctcaataaagcttgccttgagtgcttcaagtag
tgtgtgcccgtctgttgtgtgactctggtaactagagatccctcagacccttttagtcagtgtggaa
aatctctagcagtagtagttcatgtcatcttattattcagtatttataacttgcaaagaaatgaatatc
agagagtgagaggccttgacattgctagcgtttaccgtcgacctctagctagagcttggcgtaat
catggtcatagctgtttcctgtgtgaaattgttatccgctcacaattccacacaacatacgagccg
gaagcataaagtgtaaagcctggggtgcctaatgagtgagctaactcacattaattgcgttgcgc
tcactgcccgctttccagtcgggaaacctgtcgtgccagctgcattaatgaatcggccaacgcg
cggggagaggcggtttgcgtattgggcgctcttccgcttcctcgctcactgactcgctgcgctc
ggtcgttcggctgcggcgagcggtatcagctcactcaaaggcggtaatacggttatccacaga
atcaggggataacgcaggaaagaacatgtgagcaaaaggccagcaaaaggccaggaaccg
taaaaaggccgcgttgctggcgtttttccataggctccgcccccctgacgagcatcacaaaaat
cgacgctcaagtcagaggtggcgaaacccgacaggactataaagataccaggcgtttcccct
ggaagctccctcgtgcgctctcctgttccgaccctgccgcttaccggatacctgtccgcctttctc
ccttcgggaagcgtggcgctttctcatagctcacgctgtaggtatctcagttcggtgtaggtcgtt
cgctccaagctgggctgtgtgcacgaacccccgttcagcccgaccgctgcgccttatccggt
aactatcgtcttgagtccaacccggtaagacacgacttatcgccactggcagcagccactggta
acaggattagcagagcgaggtatgtaggcggtgctacagagttcttgaagtggtggcctaacta
cggctacactagaagaacagtatttggtatctgcgctctgctgaagccagttaccttcggaaaaa
gagttggtagctcttgatccggcaaacaaaccaccgctggtagcggtggtttttttgtttgcaagc
agcagattacgcgcagaaaaaaaggatctcaagaagatcctttgatcttttctacggggtctgacg
gctcagtggaacgaaaactcacgttaagggattttggtcatgagattatcaaaaaggatcttcac
ctagatccttttaaattaaaaatgaagttttaaatcaatctaaagtatatatgagtaaacttggtctga
cagttaccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgg
aagggccgagcgcagaagtggtcctgcaactttatccgcctccatccagtctattaattgttgcc
gggaagctagagtaagtagttcgccagttaatagtttgcgcaacgttgttgccattgctacaggc
atcgtggtgtcacgctcgtcgtttggtatggcttcattcagctccggttcccaacgatcaaggcga
gttacatgatcccccatgttgtgcaaaaaagcggttagctccttcggtcctccgatcgttgtcaga
agtaagttggccgcagtgttatcactcatggttatggcagcactgcataattctcttactgtcatgc
catccgtaagatgcttttctgtgactggtgagtactcaaccaagtcattctgagaatagtgtatgcg
gcgaccgagttgctcttgcccggcgtcaatacgggataataccgcgccacatagcagaacttta
aaagtgctcatcattggaaaacgttcttcggggcgaaaactctcaaggatcttaccgctgttgag
atccagttcgatgtaacccactcgtgcacccaactgatcttcagcatcttttactttcaccagcgttt
ctgggtgagcaaaaacaggaaggcaaaatgccgcaaaaaagggaataagggcgacacgga
aatgttgaatactcatactcttcctttttcaatattattgaagcatttatcagggttattgtctcatga
gcggatacatatttgaatgtatttagaaaaataaacaaataggggttccgcgcacatttccccgaaaa
gtgccacctgacgtcgacggatcgggagatcaacttgtttattgcagcttataatggttacaaata
aagcaatagcatcacaaatttcacaaataaagcatttttttcactgcattctagttgtggtttgtccaa
actcatcaatgtatcttatcatgtctggatcaactggataactcaagctaaccaaaatcatcccaaa
```

TABLE 2-continued

Exemplary nucleotide sequences

| Name | Nucleic Acid Sequence | SEQ ID NO: |
|------|----------------------|------------|
| | cttcccaccccataccctattaccactgccaattacctgtggtttcatttactctaaacctgtgattcc<br>tctgaattattttcattttaaagaaattgtatttgttaaatatgtactacaaacttagtagt | |
| 0675-V<br>pLVX-<br>MND-<br>BFP-P2A-<br>FasL_<br>deleteICD_<br>WPRE | tggaagggctaattcactcccaaagaagacaagatatccttgatctgtggatctaccacacacaa<br>ggctacttccctgattagcagaactacacaccagggccaggggtcagatatccactgacctttg<br>gatggtgctacaagctagtaccagttgagccagataaggtagaagaggccaataaaggagag<br>aacaccagcttgttacaccctgtgagcctgcatgggatggatgacccggagagagaagtgtta<br>gagtggaggtttgacagccgcctagcatttcatcacgtggcccgagagctgcatccggagtact<br>tcaagaactgctgatatcgagcttgctacaagggactttccgctggggactttccagggaggcg<br>tggcctgggcggggactggggagtggcgagccctcgagatcctgcatataagcagctgctttttgc<br>ctgtactgggtctctctggttagaccagatctgagcctgggagctctctggctaactagggaacc<br>cactgcttaagcctcaataaagcttgccttgagtgcttcaagtagtgtgtgcccgtctgttgtgtga<br>ctctggtaactagagatccctcagaccctttagtcagtgtggaaaatctctagcagtggcgccc<br>gaacagggacttgaaagcgaaagggaaaccagaggagctctctcgacgcaggactcggctt<br>gctgaagcgcgcacggcaagaggcgaggggcggcgactggtgagtacgccaaaaattttga<br>ctagcggaggctagaaggagagagatgggtgcgagagcgtcagtattaagcgggggagaat<br>tagatcgcgatgggaaaaaattcggttaaggccaggggggaaagaaaaaatatataattaaaaca<br>tatagtatgggcaagcagggagctagaacgattcgcagttaatcctggcctgttagaaacatca<br>gaaggctgtagacaaatactgggacagctacaaccatcccttcagacaggatcagaagaactt<br>agatcattatataatacagtagcaaccctctattgtgtgcatcaaaggatagagataaaagacac<br>caaggaagctttagacaagatagaggaagagcaaaacaaaagtaagaccaccgcacagcaa<br>gcggccggccgctgatcttcagacctggaggaggagatatgagggacaattggagaagtgaa<br>ttatataaatataaagtagtaaaaattgaaccattaggagtagcacccaccaaggcaaagagaa<br>gagtggtgcagagagaaaaaagagcagtgggaataggagcttgttccttgggttatggggag<br>cagcaggaagcactatgggcgcagcgtcaatgacgctgacggtacaggccagacaattattgt<br>ctggtatagtgcagcagcagaacaatttgctgagggctattgaggcgcaacagcatctgttgca<br>actcacagtctggggcatcaagcagctccaggcaagaatcctggctgtggaaagatacctaaa<br>ggatcaacagctcctggggatttggggttgctctggaaaactcatttgcaccactgctgtgccttg<br>gaatgctagttggagtaataaatctctggaacagatttggaatcacacgacctggatggagtgg<br>gacagagaaattaacaattacacaagcttaatacactccttaattgaagaatcgcaaaaccagca<br>agaaaagaatgaacaagaattattggaattagataaatgggcaagtttgtggaattggtttaacat<br>aacaaattggctgtggtatataaaattattcataatgatagtaggaggcttggtaggtttaagaata<br>gtttttgctgtactttctatagtgaatagagttaggcaggcagtattcaccattatcgtttcagaccca<br>cctcccaaccccgaggggacccgacaggcccgaaggaatagaagaagaaggtggagaga<br>gagacagagacagatccattcgattagtgaacggatctcgacggtatcgccttttaaaagaaaag<br>gggggattggggggtacagtgcaggggaaagaatagtagacataatagcaacagacataca<br>aactaaagaattacaaaaacaaattcaaaattttcgggtttattacagggacagcag<br>agatccagtttatcgatTAGTCCAATTTGTTAAAGACAGGATATCAG<br>TGGTCCAGGCTCTAGTTTTGACTCAACAATATCACCAGCT<br>GAAGCCTATAGAGTACGAGCCATAGATAAAATAAAAGAT<br>TTTATTTAGTCTCCAGAAAAAGGGGGGAATGAAAGACCC<br>CACCTGTAGGTTTGGCAAGCTAGGATCAAGGTCAGGAAC<br>AGAGAAACAGGAGAATATGGGCCAAACAGGATATCTGTG<br>GTAAGCAGTTCCTGCCCCGCTCAGGGCCAAGAACAGTTG<br>GAACAGGAGAATATGGGCCAAACAGGATATCTGTGGTAA<br>GCAGTTCCTGCCCCGCTCAGGGCCAAGAACAGATGGTCC<br>CCAGATGCGGTCCCGCCCTCAGCAGTTTCTAGAGAACCAT<br>CAGATGTTTCCAGGGTGCCCCAAGGACCTGAAATGACCC<br>TGTGCCTTATTTGAACTAACCAATCAGTTCGCTTCTCGCTT<br>CTGTTCGCGCGCTTCTGCTCCCCGAGCTCAATAAAAGAGC<br>CCACAACCCCTCACTCGGCGCGATCggatctatttccggtgaattccgcc<br>accatgagcgagctgattaaggagaacatgcacatgaagcgtacatggagggcaccgtgga<br>caaccatcacttcaagtgcacatccgagggcgaaggcaagcccctacgagggcacccagacc<br>atgagaatcaaggtggtcgagggcggccctctccccttcgccttcgacatcctggctactagctt<br>cctctacggcagcaagaccttcatcaaccacacccagggcatccccgacttcttcaagcagtcc<br>ttccctgagggcttcacatgggagagagtcaccacatacgaagacgggggcgtgctgaccgc<br>tacccaggacaccagcctccaggacggctgcctcatctacaacgtcaagatcagaggggtga<br>acttcacatccaacggccctgtgatgcagaagaaaacactcggctgggaggccttcaccgaga<br>cgctgtaccccgctgacggcggcctggaaggcagaaacgacatggcctgaagctcgtgggg<br>cggggagccatctgatcgcaaacatcaagaccacatatagatccaagaaacccgctaagaacct<br>caagatgcctggcgtctactatgtggactacagactggaaagaatcaaggaggccaacaacg<br>agacctacgtcgagcagcacgaggtggcagtggccagatactgcgacctccctagcaaactg<br>gggcacaagcttaatggaggctccggcggccgcgcaaaacgtgcaacgaatttcagcctgct<br>gaagcaggccggggacgtcgaggagaatcccgggccaatgggcaaccacagcaccggcct<br>gtgcctgctggtgatgttcttcatggtgctggtggccctggtgggcctgggcctgggcatgttcc<br>agctgttccacctgcagaagaggagctggccgagctgagagagagacaccagcccagatgcacac<br>cgccagcagcctggagaagcagatcggccacccagcccccccccccgagaagaaggagct<br>gagaaaggtggcccacctgaccggcaagagcaacagcagaagcatgcccctggagtgggga<br>ggacacctacggcatcgtgctgctgagcggcgtgaagtacaagaagggcggcctggtgatca<br>acgagaccggcctgtacttcgtgtacagcaaggtgtacttcagaggccagagctgcaacaacc<br>tgcccctgagccacaaggtgtacatgagaaacagcaagtaccccccaggacctggtgatgatg<br>gagggcaagatgatgagctactgcaccaccggccagatgtgggccagaagcagctacctgg<br>gcgccgtgttcaacctgaccagcgccgaccacctgtacgtgaacgtgagcgagctgagcctg<br>gtgaacttcgaggagagccagaccttcttcggcctgtacaagctgtgatagggcgcgccacgc<br>gtctggaacaatcaacctctggattacaaaatttgtgaaagattgactggtattcttaactatgttgc | 28 |

TABLE 2-continued

<u>Exemplary nucleotide sequences</u>

| Name | Nucleic Acid Sequence | SEQ ID NO: |
|------|----------------------|------------|
| | tcctttacgctatgtggatacgctgctttaatgcctttgtatcatgctattgcttccgtatggctt<br>tcattttctcctccttgtataaatcctggttgctgtctctttatgaggagttgtggcccgttgtcagg<br>caacgtggcgtggtgtgcactgtgtttgctgacgcaacccccactggttggggcattgccaccacct<br>gtcagctcctttccgggactttcgctttccccctccctattgccacggcggaactcatcgccgcct<br>gccttgcccgctgctggacagggctcggctgttgggcactgacaattccgtggtgttgtcggg<br>gaagctgacgtccttccatggctgctcgcctgtgttgccacctggattctgcgcgggacgtcctt<br>ctgctacgtcccttcggccctcaatccagcggaccttccttcccgcggcctgctgccggctctgc<br>ggcctcttccgcgtcttcgccttcgccctcagacgagtcggatctcccttgggccgcctccccg<br>cctggaattaattctgcagtcgagacctagaaaaacatggagcaatcacaagtagcaatacagc<br>agctaccaatgctgattgtgcctggctagaagcacaagaggaggaggaggtgggtttttccagt<br>cacacctcaggtacctttaagaccaatgacttacaaggcagctgtagatcttagccacttttttaaa<br>agaaaagaggggactggaagggctaattcactcccaacgaagacaagatatccttgatctgtg<br>gatctaccacacacaaggctacttccctgattagcagaactacacaccagggccaggggtcag<br>atatccactgacctttggatggtgctacaagctagtaccagttgagccagataaggtagaagag<br>gccaataaaggagagaacaccagcttgttacaccctgtgagcctgcatgggatggatgacccg<br>gagagagaagtgttagagtggaggtttgacagccgcctagcatttcatcacgtggcccgagag<br>ctgcatccggagtacttcaagaactgctgatatcgagcttgctacaagggactttccgctgggga<br>ctttccagggaggcgtggcctgggcgggactggggagtggcgagccctcagatcctgcatat<br>aagcagctgctttttgcctgtactgggtctctctggttagaccagatctgagcctgggagctctct<br>ggctaactagggaacccactgcttaagcctcaataaagcttgccttgagtgcttcaagtagtgtgt<br>gcccgtctgttgtgtgactctggtaactagagatccctcagacccttttagtcagtgtggaaaatct<br>ctagcagtagtagttcatgtcatcttattattcagtatttataacttgcaaagaaatgaatatcagag<br>agtgagaggccttgacattgctagcgtttaccgtcgacctctagctagagcttggcgtaatcatg<br>gtcatagctgtttcctgtgtgaaattgttatccgctcacaattccacacaacatacgagccggaag<br>cataaagtgtaaagcctggggtgcctaatgagtgagctaactcacattaattgcgttgcgctcact<br>gcccgctttccagtcgggaaacctgtcgtgccagctgcattaatgaatcggccaacgcgcggg<br>gagaggcggtttgcgtattgggcgctcttccgcttcctcgctcactgactcgctgcgctcggtcg<br>ttcggctgcggcgagcggtatcagctcactcaaaggcggtaatacggttatccacagaatcag<br>gggataacgcaggaaagaacatgtgagcaaaaggccagcaaaaggccaggaaccgtaaaa<br>aggccgcgttgctggcgtttttccataggctccgcccccctgacgagcatcacaaaaatcgacg<br>ctcaagtcagaggtggcgaaacccgacaggactataaagataccaggcgtttccccctggaa<br>gctccctcgtgcgctctcctgttccgaccctgccgcttaccggatacctgtccgcctttctcccttc<br>gggaagcgtggcgctttctcatagctcacgctgtaggtatctcagttcggtgtaggtcgttcgctc<br>caagctgggctgtgtgcacgaaccccccgttcagcccgaccgctgcgccttatccggtaactat<br>cgtcttgagtccaacccggtaagacacgacttatcgccactggcagcagccactggtaacagg<br>attagcagagcgaggtatgtaggcggtgctacagagttcttgaagtggtggcctaactacggct<br>acactagaagaacagtatttggtatctgcgctctgctgaagccagttaccttcggaaaaagagtt<br>ggtagctcttgatccggcaaacaaaccaccgctggtagcggtggtttttttgtttgcaagcagca<br>gattacgcgcagaaaaaaaggatctcaagaagatcctttgatcttttctacggggtctgacgctc<br>agtggaacgaaaactcacgttaagggattttggtcatgagattatcaaaaaggatcttcacctag<br>atccttttaaattaaaaatgaagttttaaatcaatctaaagtatatatgagtaaacttggtctgacagt<br>taccaatgcttaatcagtgaggcacctatctcagcgatctgtctatttcgttcatccatagttgcctg<br>actccccgtcgtgtagataactacgatacgggagggcttaccatctggccccagtgctgcaatg<br>ataccgcgagacccacgctcaccggctccagatttatcagcaataaaccagccagccggaag<br>ggccgagcgcagaagtggtcctgcaactttatccgcctccatccagtctattaattgttgccggg<br>aagctagagtaagtagttcgccagttaatagtttgcgcaacgttgttgccattgctacaggcatcg<br>tggtgtcacgctcgtcgtttggtatggcttcattcagctccggttcccaacgatcaaggcgagtta<br>catgatcccccatgttgtgcaaaaaagcggttagctccttcggtcctccgatcgttgtcagaagta<br>agttggccgcagtgttatcactcatggttatggcagcactgcataattctcttactgtcatgccatc<br>cgtaagatgcttttctgtgactggtgagtactcaaccaagtcattctgagaatagtgtatgcggcg<br>accgagttgctcttgcccggcgtcaatacgggataataccgcgccacatagcagaactttaaaa<br>gtgctcatcattggaaaacgttcttcggggcgaaaactctcaaggatcttaccgctgttgagatcc<br>agttcgatgtaacccactcgtgcacccaactgatcttcagcatcttttactttcaccagcgtttctgg<br>gtgagcaaaaacaggaaggcaaaatgccgcaaaaaagggaataaggggcgacacggaaatg<br>ttgaatactcatactcttcctttttcaatattattgaagcatttatcagggttattgtctcatgagcgg<br>atacatatttgaatgtatttagaaaaataaacaaataggggttccgcgcacatttccccgaaaagtgc<br>cacctgacgtcgacggatcgggagatcaacttgtttattgcagcttataatggttacaaataaagc<br>aatagcatcacaaatttcacaaataaagcattttttttcactgcattctagttgtggtttgtccaaactc<br>atcaatgtatcttatcatgtctggatcaactggataactcaagctaaccaaaatcatcccaaacttc<br>ccacccataccctattaccactgccaattacctgtggificatttactctaaacctgtgattcctctg<br>aattattttcattttaaagaaattgtatttgttaaatatgtactacaaacttagtagt | |
| 0676-V<br>pLVX-<br>MND-<br>BFP-P2A-<br>FasL_Q130D_<br>WPRE | tggaagggctaattcactcccaaagaagacaagatatccttgatctgtggatctaccacacacaa<br>ggctacttccctgattagcagaactacacaccagggccaggggtcagatatccactgacctttg<br>gatggtgctacaagctagtaccagttgagccagataaggtagaagaggccaataaaggagag<br>aacaccagcttgttacaccctgtgagcctgcatgggatggatgacccggagagagaagtgtta<br>gagtggaggtttgacagccgcctagcatttcatcacgtggcccgagagctgcatccggagtact<br>tcaagaactgctgatatcgagcttgctacaagggactttccgctggggactttccagggaggcg<br>cgctgtacccgctgacggcggcctggaaggcagaaacgacatggccctgaagctcgtggg<br>cgggagccatctgatcgcaaacatcaagaccacatatagatccaagaaaacccgctaagaacct<br>caagatgcctggcgtctactatgtggactacgactggaaagaatcaaggaggccaacaacg<br>agacctacgtcgagcagcacgaggtggcagtggccagatactgcgacctccctagcaaactg<br>gggcacaagcttaatggaggctccggcggccgcgcaaacgtgcaacgaatttcagcctgct<br>gaagcaggccggggacgtcgaggagaatcccgggccaatgcagcagcctttcaactatcctt<br>atcctcagatctattgggtcgattctagcgcctcttctccttgggcaccaccagggactgtcttgc | 29 |

TABLE 2-continued

Exemplary nucleotide sequences

| Name | Nucleic Acid Sequence | SEQ ID NO: |
|---|---|---|
| | catgcccgactagcgtgccacggagaccaggccagcgtcgacctcccccacctccacccccc cccctcccctgccaccaccaccccaccacctccccttccacccttgccacttcctccgcttaaga aacggggaaaccacagcactggcctctgcctgttggtcatgttcttcatggtgctggttgcactg gtgggactgggattggggatgttccagctgttccacttgcagaaggagttggcagaactgagg gaaagcactagccagatgcacaccgcctcaagcttggagaaggacatcggtcacccaagccc cccccccagaaaagaaggagctgaggaaggtcgcacacctcaccggtaaatccaattcccggt caatgcccctggagtgggaagacacctatggcatcgttctgctttcaggcgtcaaatacaagaa aggagggctggttatcaatgaaacagggctgtatttcgtttattccaaggtctactttcggggggca gtcctgtaacaatctccctctcagccacaaagtctacatgaggaacagcaaataccccccaggat ctggttatgatggaagggaagatgatgagctactgcactaccggccagatgtgggccaggagt tcctacctgggtgccgtcttcaaccttacttccgcagaccatctgtacgtcaacgtgagtgaactg tccctggtgaactttgaggagagtcagaccttttctcgggctgtataaactgtgatagggcgcgcc acgcgtctggaacaatcaacctctggattacaaaatttgtgaaagattgactggtattcttaactat gttgctccttttacgctatgtggatacgctgctttaatgcctttgtatcatgctattgcttcccgtatgg cttttcattttctcctccttgtataaatcctggttgctgtctctttatgaggagttgtggcccgttgtcag gcaacgtggcgtggtgtgcactgtgtttgctgacgcaacccccactggttggggcattgccacc acctgtcagctcctttccgggactttcgctttccccctccctattgccacggcggaactcatcgcc gcctgccttgcccgctgctggacaggggctcggctgttgggcactgacaattccgtggtgttgt cggggaagctgacgtcctttccatggctgctcgcctgtgttgccacctggattctgcgcgggac gtccttctgctacgtccdtcggccctcaatccagcggacctcottcccgcggcctgctgccgg ctctgcggcctcttccgcgtcttcgccttcgccctcagacgagtcggatctcccttttgggccgcct ccccgcctggaattaattctgcagtcgagacctagaaaaacatggagcaatcacaagtagcaat acagcagctaccaatgctgattgtgcctggctagaagcacaagaggaggagaggtgggttttt ccagtcacacctcaggtacctttaagaccaatgacttacaaggcagctgtagatcttagccacttt ttaaaagaaaagaggggactggaagggctaattcactcccaacgaagacaagatatccttgat ctgtggatctaccacacacaaggctacttccctgattagcagaactacacaccagggccaggg gtcagatatccactgacctttggatggtgctacaagctagtaccagttgagccagataaggtaga agaggccaataaaggagagaacaccagcttgttacaccctgtgagcctgcatgggatggatga cccggagagagaagtgttagagtggaggtttgacagccgcctagcatttcatcacgtggcccg agagctgcatccggagtacttcaagaactgctgatatcgagcttgctacaagggactttccgctg gggactttccagggaggcgtggcctgggcgggactggggagtggcgagccctcagatcctg catataagcagctgctttttgcctgtactgggtctctctggttagaccagatctgagcctgggagc tctctggctaactagggaacccactgcttaagcctcaataaagcttgccttgagtgcttcaagtag tgtgtgcccgtctgttgtgtgactctggtaactagagatccctcagacccttttagtcagtgtggaa aatctctagcagtagtagttcatgtcatcttattattcagtatttataaacttgcaaagaaatgaatatc agagagtgagaggccttgacattgctagcgtttaccgtcgacctctagctagagcttggcgtaat catggtcatagctgtttcctgtgtgaaattgttatccgctcacaattccacacaacatacgagccg gaagcataaagtgtaaagcctggggtgcctaatgagtgagctaactcacattaattgcgttgcgc tcactgcccgctttccagtcgggaaacctgtcgtgccagctgcattaatgaatcggccaacgcg cggggagaggcggtttgcgtattgggcgctcttccgcttcctcgctcactgactcgctgcgctc ggtcgttcggctgcggcgagcggtatcagctcactcaaaggcggtaatacggttatccacaga atcagggggataacgcaggaaagaacatgtgagcaaaaggccagcaaaaggccaggaaccg taaaaaggccgcgttgctggcgtttttccataggctccgcccccctgacgagcatcacaaaaat cgacgctcaagtcagaggtggcgaaacccgacaggactataaagataccaggcgtttccccct ggaagctccctcgtgcgctctcctgttccgaccctgccgcttaccggatacctgtccgcctttctc ccttcgggaagcgtggcgctttctcatagctcacgctgtaggtatctcagttcggtgtaggtcgtt cgctccaagctgggctgtgtgcacgaacccccccgttcagcccgaccgctgcgccttatccggt aactatcgtcttgagtccaacccggtaagacacgacttatcgccactggcagcagccactggta acaggattagcagagcgaggtatgtaggcggtgctacagagttcttgaagtggtggcctaacta cggctacactagaagaacagtatttggtatctgcgctctgctgaagccagttaccttcggaaaaa gagttggtagctcttgatccggcaaacaaaccaccgctggtagcggtggtttttttgtttgcaagc agcagattacgcgcagaaaaaaaggatctcaagaagatcctttgatcttttctacggggtctgac gctcagtggaacgaaaactcacgttaagggattttggtcatgagattatcaaaaaggatcttcac ctagatccttttaaattaaaaatgaagttttaaatcaatctaaagtatatatgagtaaacttggtctga cagttaccaatgcttaatcagtgaggcacctatctcagcgatctgtctatttcgttcatccatagttg cctgactccccgtcgtgtagataactacgatacgggagggcttaccatctggccccagtgctgc aatgataccgcgagacccacgctcaccggctccagatttatcagcaataaaccagccagccgg aagggccgagcgcagaagtggtcctgcaactttatccgcctccatccagtctattaattgttgcc gggaagctagagtaagtagttcgccagttaatagtttgcgcaacgttgttgccattgctacaggc atcgtggtgtcacgctcgtcgtttggtatggcttcattcagctccggttcccaacgatcaaggcga gttacatgatcccccatgttgtgcaaaaaagcggttagctccttcggtcctccgatcgttgtcaga agtaagttggccgcagtgttatcactcatggttatggcagcactgcataattctcttactgtcatgc catccgtaagatgcttttctgtgactggtgagtactcaaccaagtcattctgagaatagtgtatgcg gcgaccgagttgctatgcccggcgtcaatacgggataataccgcgccacatagcagaacttta aaagtgctcatcattggaaaacgttcttcggggcgaaaactctcaaggatcttaccgctgttgag atccagttcgatgtaacccactcgtgcacccaactgatcttcagcatcttttactttcaccagcgttt ctgggtgagcaaaaacaggaaggcaaaatgccgcaaaaaagggaataagggcgacacgga aatgttgaatactcatactcttcctttttcaatattattgaagcatttatcagggttattgtctcatga gcggatacatatttgaatgtatttagaaaaataaacaaataggggttccgcgcacatttccccgaaa gtgccacctgacgtcgacggatcaggggagtcaacttgtttattgcagcttataatggttacaaata aagcaatagcatcacaaatttcacaaataaagcatttttttcactgcattctagttgtggtttgtccaa actcatcaatgtatcttatcatgtctggatcaactggataactcaagctaaccaaaatcatcccaaa cttcccacccataccctattaccactgccaattacctgtggtttcatttactctaaacctgtgattcc tctgaattattttcattttaaagaaattgtatttgttaaatatgtactacaaacttagtagt | |

TABLE 2-continued

Exemplary nucleotide sequences

| Name | Nucleic Acid Sequence | SEQ ID NO: |
|------|----------------------|------------|
| 0677-V pLVX- MND- BFP-P2A- FasL_C82A_ WPRE_ updated_ codopt_ 20191205 | tggaagggctaattcactcccaaagaagacaagatatccttgatctgtggatctaccacacacaa ggctacttccctgattagcagaactacacaccagggccaggggtcagatatccactgacctttg gatggtgctacaagctagtaccagttgagccagataaggtagaagaggccaataaaggagag aacaccagcttgttacaccctgtgagcctgcatgggatggatgacccggagagagaagtgtta gagtggaggtttgacagccgcctagcatttcatcacgtggcccgagagctgcatccggagtact tcaagaactgctgatatcgagcttgctacaagggactttccgctggggactttccagggaggcg tggcctgggcgggactggggagtggcgagccctcagatcctgcatataagcagctgctttttgc ctgtactgggtctctctggttagaccagatctgagcctgggagctctctggctaactagggaacc cactgcttaagcctcaataaagcttgccttgagtgcttcaagtagtgtgtgcccgtctgttgtgtga ctctggtaactagagatccctcagacccttttagtcagtgtggaaaatctctagcagtggcgccc gaacagggacttgaaagcgaaagggaaaccagaggagctctctcgacgcaggactcggctt gctgaagcgcgcacggcaagaggcgaggggcggcgactggtgagtacgccaaaaattttga ctagcggaggctagaaggagagagatgggtgcgagagcgtcagtattaagcgggggagaat tagatcgcgatgggaaaaaattcggttaaggccaggggaaagaaaaaatatasaattaaaaca tatagtatgggcaagcagggagctagaacgattcgcagttaatcctggcctgttagaaacatca gaaggctgtagacaaatactgggacagctacaaccatcccttcagacaggatcagaagaactt agatcattatataatacagtagcaacccctctattgtgtgcatcaaaggatagagataaaagacac caaggaagcttttagacaagatagaggaagagcaaaacaaaagtaagaccaccgcacagcaa gcggccgccgctgatcttcagacctggaggaggagatatgagggacaattggagaagtgaa ttatataaatataaagtagtaaaaattgaaccattaggagtagcacccaccaaggcaaagagaa gagtggtgcagagagaaaaaagagcagtgggaataggagctttgttccttgggttcttgggag cagcaggaagcactatgggcgcagcgtcaatgacgctgacggtacaggccagacaattattgt ctggtatagtgcagcagcagaacaatttgctgagggctattgaggcgcaacagcatctgttgca actcacagtctggggcatcaagcagctccaggcaagaatcctggctgtgtggaaagatacctaaa ggatcaacagctcctggggatttggggttgctctggaaaactcatttgcaccactgctgtgccttg gaatgctagttggagtaataaatctctggaacagatttggaatcacacgacctggatggagtgg gacagagaaattaacaattacacaagcttaatacactccttaattgaagaatcgcaaaaccagca agaaaagaatgaacaagaattattggaattagataaatgggcaagtttgtggaattggtttaacat aacaaattggctgtgtatataaaaattattcataatgatagtaggaggcttggtaggtttaagaata gtttttgctgtactttctatagtgaatagagttaggcagggatatattcaccattatcgtttcagaccca cctcccaaccccgaggggacccgacaggcccgaaggaatagaagaagaaggtggagaga gagacagagacagatccattcgattagtgaacggatctcgacggtatcgcctttaaaagaaaag ggggattggggggtacagtgcaggggaaagaatagtagacataatagcaacagacatacac aactaaagaattacaaaaacaaattacaaaaattcaaaattttcgggtttattacagggacagcag agatccagtttatcgatTAGTCCAATTTGTTAAAGACAGGATATCAG TGGTCCAGGCTCTAGTTTTGACTCAACAATATCACCAGCT GAAGCCTATAGAGTACGAGCCATAGATAAAATAAAAGAT TTTATTTAGTCTCCAGAAAAAGGGGGGAATGAAAGACCCC CACCTGTAGGTTTGGCAAGCTAGGATCAAGGTCAGGAAC AGAGAAACAGGAGAATATGGGCCAAACAGGATATCTGTG GTAAGCAGTTCCTGCCCCGCTCAGGGCCAAGAACAGTTG GAACAGGAGAATATGGGCCAAACAGGATATCTGTGGTAA GCAGTTCCTGCCCCGCTCAGGGCCAAGAACAGATGGTCC CCAGATGCGGTCCCGCCCCTCAGCAGTTTCTAGAGAACCAT CAGATGTTTCCAGGGTGCCCCAAGGACCTGAAATGACCC TGTGCCTTATTTGAACTAACCAATCAGTTCGCTTCTCGCTT CTGTTCGCGCGCTTCTGCTCCCCGAGCTCAATAAAAGAGC CCACAACCCCTCACTCGGCGCGATCggatctatttccggtgaattccgcc accatgagcgagctgattaaggagaacatgcacatgaagctgtgtacatggagggcaccgtgga caaccatcacttcaagtgcacatccgagggcgaaggcaagcccacgagggcacccagacc atgagaatcaaggtggtcgagggcgggccctctcccttcgccttcgacatcctggctactagctt cctctacggcagcaagacctttcatcaaccacacccagggcatccccgacttcttcaagcagtcc ttccctgagggcttcacatgggagagagtcaccacatacgaagacggggggcgtgctgaccgc tacccaggacaccagcctccaggacggctgcctcatctacaacgtcaagatcagagggtcgag acttcacatccaacggccctgtgatgcagaagaaaacactcggctgggaggccttcaccgaga cgctgtaccccgctgacggcggcctggaagcagaaacgacatggccctgaagctcgtgggg cgggagccatctgatcgcaaacatcaagaccacatatagatccaagaaacccgctaagaacct caagatgcctggcgtctactatgtggactacagactggaaagaatcaaggaggccaacaacg agacctacgtcgagcagcacgaggtggcagtggccagatactgcgacctccctagcaaactg gggcacaagcttaatggaggctccggcggccgcgcaaaacgtgcaacgaatttcagcctgct gaagcaggccggggacgtcgaggagaatcccgggcaatgcagcagcctttcaactatcctt atcctcagatctcattgggtcgattctagcgcctcttctccttgggcaccaccaggggacctgcttgc catgcccgactagcgtgccacggagaccaggccagcgtcgacctccccacctccacccccc ccctccctgccaccaccaccccaccacctcccttccacccttgccacttcctccgcttaaga aacggggaaaccacagcactggcctcgccctgttggtcatgttcttcatggtgctggttgcactg gtgggactgggattggggatgttccagctgttccacttgcagaaggagttggcagaactgagg gaaagcactagccagatgcacaccgcctcaagcttggagaagcagatcggtcacccaagccc ccccccagaaaagaaggagctgaggaaggtcgcacacctcaccggtaaatccaattcccggt caatgcccctggagtgggaagacacctatggcatcgttctgctttcaggcgtcaaatacaagaa aggagggctggttatcaatgaaacagggctgtatttcgtttattccaaggtctacttttcggggggca gtcctgtaacaatctccctctcagccacaaagtctacatgaggaacagcaaatacccccaggat ctggttatgatggaagggaagatgatgagctactgcactaccggccagatgtgggccaggagt tcctacctgggtgccgtcttcaaccttacttccgcagaccatctgtacgtcaacgtgagtgaactg tccctggtgaactttgaggagtcagaccttttttcgggctgtataaactgtgataggggcgcgcc acgcgtctggaacaatcaacctctgattacaaaatttgtgaaagattgactggtattcttaactat | 30 |

TABLE 2-continued

Exemplary nucleotide sequences

| Name | Nucleic Acid Sequence | SEQ ID NO: |
|------|----------------------|------------|
| | gttgctccttttacgctatgtggatacgctgctttaatgcctttgtatcatgctattgcttcccgtat<br>ggctttcattttctcctccttgtataaatcctggttgctgtctctttatgaggagttgtggcccgttg<br>tcaggcaacgtggcgtggtgtgcactgtgtttgctgacgcaaccccactggttggggcattgccacc<br>acctgtcagctcctttccgggactttcgctttccccctccctattgccacggcggaactcatcgcc<br>gcctgccttgcccgctgctggacagggggctcggctgttgggcactgacaattccgtggtgttgt<br>cggggaagctgacgtcctttccatggctgctcgcctgtgttgccacctggattctgcgcgggac<br>gtccttctgctacgtcccttcggccctcaatccagcggacctccttcccgcggcctgctgccgg<br>ctctgcggcctcttccgcgtcttcgccttcgccctcagacgagtcggatctcccttggggccgcct<br>ccccgcctggaattaattctgcagtcgagacctagaaaaacatggagcaatcacaagtagcaat<br>acagcagctaccaatgctgattgtgcctggctagaagcacaagaggaggaggaggtgggtttt<br>ccagtcacacctcaggtacctttaagaccaatgacttacaaggcagctgtagatcttagccacttt<br>ttaaaagaaaagaggggactggaagggctaattcactcccaacgaagacaagatatccttgat<br>ctgtggatctaccacacacaaggctacttccctgattagcagaactacacaccagggccaggg<br>gtcagatatccactgacctttggatggtgctacaagctagtaccagttgagccagataaggtaga<br>agaggccaataaaggagagaacaccagcttgttacaccctgtgagcctgcatgggatggatga<br>cccggagagagaagtgttagagtggaggtttgacagccgcctagcatttcatcacgtggcccg<br>agagctgcatccggagtacttcaagaactgctgatatcgagcttgctacaagggactttccgctg<br>gggactttccagggaggcgtggcctgggcgggactggggagtggcgagccctcagatcctg<br>catataagcagctgctttttgcctgtactgggtctctctggttagaccagatctgagcctgggagc<br>tctctggctaactagggaacccagctgcttaagcctcaataaagcttgccttgagtgcttcaagtag<br>tgtgtgcccgtctgttgtgtgactctggtaactagagatccctcagacccttttagtcagtgtggaa<br>aatctctagcagtagtagttcatgtcatcttattattcagtatttataacttgcaaagaaatgaatatc<br>agagagtgagaggccttgacattgctagcgtttaccgtcgacctctagctagagcttggcgtaat<br>catggtcatagctgtttcctgtgtgaaattgttatccgctcacaattccacacaacatacgagccg<br>gaagcataaagtgtaaagcctggggtgcctaatgagtgagctaactcacattaattgcgttgcgc<br>tcactgcccgctttccagtcgggaaacctgtcgtgccagctgcattaatgaatcggccaacgcg<br>cggggagaggcggtttgcgtattgggcgctcttccgcttcctcgctcactgactcgctgcgctc<br>ggtcgttcggctgcggcgagcggtatcagctcactcaaaggcggtaatacggttatccacaga<br>atcaggggataacgcaggaaagaacatgtgagcaaaaggccagcaaaaggccaggaaccg<br>taaaaaggccgcgttgctggcgtttttccataggctccgcccccctgacgagcatcacaaaaat<br>cgacgctcaagtcagaggtggcgaaacccgacaggactataaagataccaggcgtttcccct<br>ggaagctccctcgtgcgctctcctgttccgaccctgccgcttaccggatacctgtccgcctttctc<br>ccttcgggaagcgtggcgctttctcatagctcacgctgtaggtatctcagttcggtgtaggtcgtt<br>cgctccaagctgggctgtgtgcacgaacccccccgttcagcccgaccgctgcgccttatccggt<br>aactatcgtcttgagtccaacccggtaagacacgacttatcgccactggcagcagccactggta<br>acaggattagcagagcgaggtatgtaggcggtgctacagagttcttgaagtggtggcctaacta<br>cggctacactagaagaacagtatttggtatctgcgctctgctgaagccagttaccttcggaaaaa<br>gagttggtagctcttgatccggcaaacaaaccaccgctggtagcggtggtttttttgtttgcaagc<br>agcagattacgcgcagaaaaaaaggatctcaagaagatcctttgatcttttctacggggtctgac<br>gctcagtggaacgaaaactcacgttaagggattttggtcatgagattatcaaaaaggatcttcac<br>ctagatccttttaaattaaaaatgaagttttaaatcaatctaaagtatatatgagtaaaacttggtctga<br>cagttaccaatgcttaatcagtgaggcacctatctcagcgatctgtctatttcgttcatccatagttg<br>cctgactccccgtcgtgtagataactacgatacgggagggcttaccatctggccccagtgctgc<br>aatgataccgcgagacccacgctcaccggctccagatttatcagcaataaaccagccagccgg<br>aagggccgagcgcagaagtggtcctgcaactttatccgcctccatccagtctattaattgttgcc<br>gggaagctagagtaagtagttcgccagttaatagtttgcgcaacgttgttgccattgctacaggc<br>atcgtggtgtcacgctcgtcgtttggtatggcttcattcagctccggttcccaacgatcaaggcga<br>gttacatgatcccccatgttgtgcaaaaaagcggttagctccttcggtcctccgatcgttgtcaga<br>agtaagttggccgcagtgttatcactcatggttatggcagcactgcataattctcttactgtcatgc<br>catccgtaagatgcttttctgtgactggtgagtactcaaccaagtcattctgagaatagtgtatgcg<br>gcgaccgagttgctatgccggcgtcaatacgggataataccgcgccacatagcagaacttta<br>aaagtgctcatcattggaaaacgttcttcggggcgaaaactctcaaggatcttaccgctgttgag<br>atccagttcgatgtaacccactcgtgcacccaactgatcttcagcatcttttactttcaccagcgttt<br>ctgggtgagcaaaaacaggaaggcaaaatgccgcaaaaaagggaataagggcgacacgga<br>aatgttgaatactcatactcttcctttttcaatattattgaagcatttatcagggttattgtctcatga<br>gcggatacatatttgaatgtatttagaaaaataaacaaataggggttccgcgcacatttccccgaaaa<br>gtgccacctgacgtcgacggatcgggagatcaacttgtttattgcagcttataatggttacaaata<br>aagcaatagcatcacaaatttcacaaataaagcatttttttcactgcattctagttgtggtttgtccaa<br>actcatcaatgtatcttatcatgtctggatcaactggataactcaagctaaccaaaatcatcccaaa<br>cttccccaccccatacccattaccactgccaattacctgtggtttcatttactctaaacctgtgattcc<br>tctgaattattttcattttaaagaaattgtatttgttaaatatgtactacaaacttagtagt | |
| 916-V<br>pLVX-<br>MND-<br>BFP-P2A-<br>FasL_EEAAA_<br>WPRE<br>("EEAAA"<br>disclosed<br>as SEQ ID<br>NO: 33) | ggaagggctaattcactcccaaagaagacaagatatccttgatctgtggatctaccacacacaa<br>ggctacttccctgattagcagaactacacaccagggccaggggtcagatatccactgacctttg<br>gatggtgctacaagctagtaccagttgagccagataaggtagaagaggccaataaaggagag<br>aacaccagcttgttacaccctgtgagcctgcatgggatggatgacccggagagagaagtgtta<br>gagtggaggtttgacagccgcctagcatttcatcacgtggcccgagagctgcatccggagtact<br>tcaagaactgctgatatcgagcttgctacaagggactttccgctggggactttccagggaggcg<br>tggcctgggcgggactggggagtggcgagccctcagatcctgcatataagcagctgctttttgc<br>ctgtactgggtctctctggttagaccagatctgagcctgggagctctctggctaactagggaaccc<br>cactgcttaagcctcaataaagcttgccttgagtgcttcaagtagtgtgtgcccgtctgttgtgtga<br>ctctggtaactagagatccctcagacccttttagtcagtgtggaaaatctctagcagtggcgccc<br>gaacagggacttgaaagcgaaagggaaaccagaggagctctctcgacgcaggactcggctt<br>gctgaagcgcgcacggcaagaggcgaggggcggcgactggtgagtacgccaaaaattttga<br>ctagcggaggctagaaggagagagatgggtgcgagagcgtcagtattaagcgggggagaat | 31 |

TABLE 2-continued

Exemplary nucleotide sequences

| Name | Nucleic Acid Sequence | SEQ ID NO: |
|------|----------------------|------------|
| | tagatcgcgatgggaaaaaattcggttaaggccaggggggaaagaaaaaatataaattaaaaca | |
| | tatagtatgggcaagcagggagctagaacgattcgcagttaatcctggcctgttagaaacatca | |
| | gaaggctgtagacaaatactgggacagctacaaccatcccttcagacaggatcagaagaactt | |
| | agatcattatataatacagtagcaaccctctattgtgtgcatcaaaggatagagataaaagacac | |
| | caaggaagctttagacaagatagaggaagagcaaaacaaaagtaagaccaccgcacagcaa | |
| | gcggccggccgctgatcttcagacctggaggaggagatatgagggacaattggagaagtgaa | |
| | ttatataaatatataaagtagtaaaaattgaaccattaggagtagcacccaccaaggcaaagagaa | |
| | gagtggtgcagagagaaaaaagagcagtgggaataggagattgttccttgggttatgggag | |
| | cagcaggaagcactatgggcgcagcgtcaatgacgctgacggtacaggccagacaattattgt | |
| | ctggtatagtgcagcagcagaacaatttgctgagggctattgaggcgcaacagcatctgttgca | |
| | actcacagtctggggcatcaagcagctccaggcaagaatcctggctgtggaaagatacctaaa | |
| | ggatcaacagctcctggggatttggggttgctctggaaaactcatttgcaccactgctgtgccttg | |
| | gaatgctagttggagtaataaatctctggaacagatttggaatcacacgacctggatggagtgg | |
| | gacagagaaattaacaattacacaagcttaatacactccttaattgaagaatcgcaaaaccagca | |
| | agaaaagaatgaacaagaattattggaattagataaatgggcaagtttgtggaattggtttaacat | |
| | aacaaattggctgtggtatataaaattattcataatgatagtaggaggcttggtaggtttaagaata | |
| | gtttttgctgtactttctatagtgaatagagttaggcagggatattcaccattatcgtttcagaccca | |
| | cctcccaaccccgaggggacccgacaggcccgaaggaatagaagaagaaggtggagaga | |
| | gagacagagacagatccattcgattagtgaacggatctcgacggtatcgcctttaaaagaaaag | |
| | ggggattggggggtacagtgcaggggaaagaatagtagacataatagcaacagacataca | |
| | aactaaagaattacaaaaacaaattacaaaaattcaaaattttcgggtttattacagggacagcag | |
| | agatccagtttatcgatTAGTCCAATTTGTTAAAGACAGGATATCAG | |
| | TGGTCCAGGCTCTAGTTTTGACTCAACAATATCACCAGCT | |
| | GAAGCCTATAGAGTACGAGCCATAGATAAAATAAAAGAT | |
| | TTTATTTAGTCTCCAGAAAAAGGGGGGAATGAAAGACCC | |
| | CACCTGTAGGTTTGGCAAGCTAGGATCAAGGTCAGGAAC | |
| | AGAGAAACAGGAGAATATGGGCCAAACAGGATATCTGTG | |
| | GTAAGCAGTTCCTGCCCCGCTCAGGGCCAAGAACAGTTG | |
| | GAACAGGAGAATATGGGCCAAACAGGATATCTGTGGTAA | |
| | GCAGTTCCTGCCCCGCTCAGGGCCAAGAACAGATGGTCC | |
| | CCAGATGCGGTCCCGCCCTCAGCAGTTTCTAGAGAACCAT | |
| | CAGATGTTTCCAGGGTGCCCCAAGGACCTGAAATGACCC | |
| | TGTGCCTTATTTGAACTAACCAATCAGTTCGCTTCTCGCTT | |
| | CTGTTCGCGCGCTTCTGCTCCCCGAGCTCAATAAAAGAGC | |
| | CCACAACCCCTCACTCGGCGCGATCggatctatttccggtgaattccgcc | |
| | accatgagcgagctgattaaggagaacatgcacatgaagctgtacatggagggcaccgtgga | |
| | caaccatcacttcaagtgcacatccgagggcgaaggcaagccctacgagggcacccagacc | |
| | atgagaatcaaggtggtcgagggcggccctctcccttcgccttcgacatcctggctactagctt | |
| | cctctacggcagcaagacctttcatcaaccacacccagggcatccccgacttcttcaagcagtcc | |
| | ttccctgagggcttcacatgggagagagtcaccacatacgaagacgggggcgtgctgaccgc | |
| | tacccaggacaccagcctccaggacggctgcctcatctacaacgtcaagatcagagggtga | |
| | acttcacatccaacggccctgtgatgcagaagaaaacactcggctgggaggccttcaccgaga | |
| | cgctgtaccccgctgacggcggcctggaaggcagaaacgacatggccctgaagctcgtggg | |
| | cgggagccatctgatcgcaaacatcaagaccacatatagatccaagaaacccgctaagaacct | |
| | caagatgcctggcgtctactatgtggactacagactggaaagaatcaaggaggccaacaacg | |
| | agacctacgtcgagcagcacgaggtggcagtggccagatactgcgacctccctagcaaactg | |
| | gggcacaagcttaatggaggctccggcggccgcgcaaaacgtgcaacgaatttcagcctgct | |
| | gaagcaggccggggacgtcgaggagaatcccgggccaatgcagcagcctttcaactatcctt | |
| | atcctcagatctctattgggtcgattctagcgcctcttctccttgggcaccaccagggactgtcttgc | |
| | catgcccgactagcgtgccacggagaccaggccagcgtcgacctcccccacctccacccc | |
| | ccctcccctgccaccaccacccccaccacctcccttccacccttgccacttcctccgcttaaga | |
| | aacggggaaaccacagcactggcctctgcctgttggtcatgttcttcatggtgctggttgcactg | |
| | gtgggactgggattggggatgttccagctgttccacttgcagaaggagttggcagaactgagg | |
| | gaaagcactagccagatgcacaccgcctcagaggaagccgctgccatcggtcacccaagcc | |
| | cccccccagaaaagaaggagctgaggaaggtcgcacacctcaccggtaaatccaattcccgg | |
| | tcaatgcccctggagtgggaagacacctatggcatcgttctgctttcaggcgtcaaatacaaga | |
| | aaggagggctggttatcaatgaaacagggctgtatttcgtttattccaaggtctactttcggggc | |
| | agtcctgtaacaatctccctctcagccacaaagtctacatgaggaacagcaaatacccccagga | |
| | tctggttatgatggaagggaagatgatgagctactgcactaccggccagatgtgggccaggag | |
| | ttcctacctgggtgccgtcttcaaccttacttccgcagaccatctgtacgtcaacgtgagtgaact | |
| | gtccctggtgaactttgaggagagtcagacctttttcgggctgtataaactgtgatagggcgcgc | |
| | cacgcgtctggaacaatcaacctctggattacaaaatttgtgaaagattgactgattattcttaacta | |
| | tgttgctcctttacgctatgtggatacgctgctttaatgcctttgtatcatgctattgcttcccgtatg | |
| | gctttcattttctcctccttgtataaatcctggttgctgtctctttatgaggagttgtggcccgttgtca | |
| | ggcaacgtggcgtggtgtgcactgtgtttgctgacgcaaccccccactggttggggcattgccac | |
| | cacctgtcagctcctttccgggactttcgctttccccctccctattgccacggcggaactcatcgc | |
| | cgcctgccttgcccgctgctggacaggggctcggctgttgggcactgacaattccgtggtgttg | |
| | tcggggaagctgacgtcctttccatggctgctcgcctgtgttgccacctggattctgcgcgggac | |
| | gtccttctgctacgtccdtcggccctcaatccagcggaccttccttcccgcggcctgctgccgg | |
| | ctctgcggcctcttccgcgtcttcgccttcgccctcagacgagtcggatctccctttgggccgcct | |
| | ccccgcctggaattaattctgcagtcgagaccctagaaaacatggagcaatcacaagtagcaat | |
| | acagcagctaccaatgctgattgtgcctggctagaagcacaagaggaggaggaggtgggtttt | |
| | ccagtcacacctcaggtacctttaagaccaatgacttacaaggcagctgtagatcttagccacttt | |
| | ttaaaagaaaagaggggactggaagggctaattcactcccaacgaagacaagatatccttgat | |
| | ctgtggatctaccacacacaaggctacttccctgattagcagaactacacaccagggccaggg | |

TABLE 2-continued

Exemplary nucleotide sequences

| Name | Nucleic Acid Sequence | SEQ ID NO: |
|---|---|---|
| | gtcagatatccactgacctttggatggtgctacaagctagtaccagttgagccagataaggtaga | |
| | agaggccaataaaggagagaacaccagcttgttacaccctgtgagcctgcatgggatggatga | |
| | cccggagagagaagtgttagagtggaggtttgacagccgcctagcatttcatcacgtggcccg | |
| | agagctgcatccggagtacttcaagaactgctgatatcgagcttgctacaagggactttccgctg | |
| | gggactttccagggaggcgtggcctgggcgggactggggagtggcgagccctcagatcctg | |
| | catataagcagctgctttttgcctgtactgggtctctctggttagaccagatctgagcctgggagc | |
| | tctctggctaactagggaacccactgcttaagcctcaataaagcttgccttgagtgcttcaagtag | |
| | tgtgtgcccgtctgttgtgtgactctggtaactagagatccctcagacccttttagtcagtgtggaa | |
| | aatctctagcagtagtagttcatgtcatcttattattcagtatttataacttgcaaagaaatgaatatc | |
| | agagagtgagaggccttgacattgctagcgtttaccgtcgacctctagctagagcttggcgtaat | |
| | catggtcatagctgtttcctgtgtgaaattgttatccgctcacaattccacacaacatacgagccg | |
| | gaagcataaagtgtaaagcctggggtgcctaatgagtgagctaactcacattaattgcgttgcgc | |
| | tcactgcccgctttccagtcgggaaacctgtcgtgccagctgcattaatgaatcggccaacgcg | |
| | cggggagaggcggtttgcgtattgggcgctcttccgcttcctcgctcactgactcgctgcgctc | |
| | ggtcgttcggctgcggcgagcggtatcagctcactcaaaggcggtaatacggttatccacaga | |
| | atcaggggataacgcaggaaagaacatgtgagcaaaaggccagcaaaaggccaggaaccg | |
| | taaaaaggccgcgttgctggcgtttttccataggctccgcccccctgacgagcatcacaaaaat | |
| | cgacgctcaagtcagaggtggcgaaacccgacaggactataaagataccaggcgtttccccct | |
| | ggaagctccctcgtgcgctctcctgttccgaccctgccgcttaccggatacctgtccgcctttctc | |
| | ccttcgggaagcgtggcgctttctcatagctcacgctgtaggtatctcagttcggtgtaggtcgtt | |
| | cgctccaagctgggctgtgtgcacgaaccccccgttcagcccgaccgctgcgccttatccggt | |
| | aactatcgtcttgagtccaacccggtaagacacgacttatcgccactggcagcagccactggta | |
| | acaggattagcagagcgaggtatgtaggcggtgctacagagttcttgaagtggtggcctaacta | |
| | cggctacactagaagaacagtatttggtatctgcgctctgctgaagccagttaccttcggaaaaa | |
| | gagttggtagctcttgatccggcaaacaaaccaccgctggtagcggtggtttttttgtttgcaagc | |
| | agcagattacgcgcagaaaaaaaggatctcaagaagatcctttgatcttttctacggggtctgac | |
| | gctcagtggaacgaaaactcacgttaagggattttggtcatgagattatcaaaaaggatcttcac | |
| | ctagatccttttaaattaaaaatgaagttttaaatcaatctaaagtatatatgagtaaacttggtctga | |
| | cagttaccaatgcttaatcagtgaggcacctatctcagcgatctgtctatttcgttcatccatagttg | |
| | cctgactccccgtcgtgtagataactacgatacgggagggcttaccatctggccccagtgctgc | |
| | aatgataccgcgagacccacgctcaccggctccagatttatcagcaataaaccagccagccgg | |
| | aagggccgagcgcagaagtggtcctgcaactttatccgcctccatccagtctattaattgttgcc | |
| | gggaagctagagtaagtagttcgccagttaatagtttgcgcaacgttgttgccattgctacaggc | |
| | atcgtggtgtcacgctcgtcgtttggtatggcttcattcagctccggttcccaacgatcaaggcga | |
| | gttacatgatcccccatgttgtgcaaaaaagcggttagctccttcggtcctccgatcgttgtcaga | |
| | agtaagttggccgcagtgttatcactcatggttatggcagcactgcataattctcttactgtcatgc | |
| | catccgtaagatgcttttctgtgactggtgagtactcaaccaagtcattctgagaatagtgtatgcg | |
| | gcgaccgagttgctcttgcccggcgtcaatacgggataataccgcgccacatagcagaacttta | |
| | aaagtgctcatcattggaaaacgttcttcggggcgaaaactctcaaggatcttaccgctgttgag | |
| | atccagttcgatgtaacccactcgtgcacccaactgatcttcagcatcttttactttcaccagcgttt | |
| | ctgggtgagcaaaaacaggaaggcaaaatgccgcaaaaaagggaataagggcgacacgga | |
| | aatgttgaatactcatactcttcctttttcaatattattgaagcatttatcagggttattgtctcatga | |
| | gcggatacatatttgaatgtatttagaaaaataaacaaataggggttccgcgcacatttccccgaaa | |
| | gtgccacctgacgtcgacggatcgggagatcaacttgtttattgcagcttataatggttacaaata | |
| | aagcaatagcatcacaaatttcacaaataaagcatttttttcactgcattctagttgtggtttgtccaa | |
| | actcatcaatgtatcttatcatgtctggatcaactggataactcaagctaaccaaaatcatcccaaa | |
| | cttcccaccccataccctattaccactgccaattacctgtggtttcatttactctaaacctgtgattcc | |
| | tctgaattattttcattttaaagaaattgtatttgttaaatatgtactacaaacttagtagt | |

In some embodiments, an immune cell e.g., a T cell of the present disclosure comprises and/or expresses a polypeptide that comprises any one or more of the sequences (e.g., expresses) listed in Table 1, and/or comprises and/or expresses a nucleic acid e.g. a vector that comprises any one or more of the nucleic acid sequences listed in Table 2.

In some embodiments, an immune cell e.g., a T cell of the present disclosure comprises and/or expresses a polypeptide that comprises (e.g., expresses) the amino acid sequence of FasL wild-type (UniprotKB-P48023). In some embodiments, an immune cell e.g. T cell of the present disclosure comprises and/or expresses a polypeptide that comprises (e.g. expresses) the amino acid sequence of FasL Acyto (a.k.a. FasL delta 2-74). In some embodiments, an immune cell e.g. T cell of the present disclosure comprises and/or expresses a polypeptide that comprises (e.g. expresses) the amino acid sequence of FasL C82A. In some embodiments, an immune cell e.g., a T cell of the present disclosure comprises and/or expresses a polypeptide that comprises (e.g. expresses) the amino acid sequence of FasL SLEKQ→EEAAA (SEQ ID NOs: 32 and 33, respectively) (a.k.a. FasL SLEKQ126-130→EEAAA (SEQ ID NOs: 32 and 33, respectively)). In some embodiments, an immune cell e.g., a T cell of the present disclosure comprises and/or expresses a polypeptide that comprises (e.g., expresses) the amino acid sequence of FasL Q130D.

In some embodiments, an immune cell e.g., a T cell of the present disclosure comprises and/or expresses a nucleic acid e.g., a vector that comprises any one or more of the nucleic acid sequences listed in Table 2. In some embodiments, an immune cell e.g., a T cell of the present disclosure comprises and/or expresses a nucleic acid e.g., a vector that comprises the nucleic acid sequence of FasL wild-type. In some embodiments, an immune cell e.g., a T cell of the present disclosure comprises and/or expresses a nucleic acid e.g., a vector that comprises the nucleic acid sequence of FasL Acyto. In some embodiments, an immune cell e.g., a T cell of the present disclosure comprises and/or expresses a nucleic acid e.g., a vector that comprises the nucleic acid sequence of FasL C82A. In some embodiments, an immune cell e.g., a T cell of the present disclosure comprises and/or expresses a nucleic acid e.g. a vector that comprises the nucleic acid sequence of FasL SLEKQ→EEAAA (SEQ ID NOs: 32 and 33, respectively). In some embodiments, an immune cell e.g., a T cell of the present disclosure comprises and/or expresses a nucleic acid e.g. a vector that comprises the nucleic acid sequence of FasL Q130D.

In some embodiments, an immune cell e.g., a T cell of the present disclosure comprises and/or expresses a nucleic acid e.g., a vector that comprises any one or more of the nucleic acid sequences listed in Table 2. In some embodiments, an immune cell e.g., a T cell of the present disclosure comprises and/or expresses a nucleic acid e.g., a vector that encodes FasL wild-type. In some embodiments, an immune cell e.g., a T cell of the present disclosure comprises and/or expresses a nucleic acid e.g. a vector that encodes FasL Acyto. In some embodiments, an immune cell e.g., a T cell of the present disclosure comprises and/or expresses a nucleic acid e.g. a vector that encodes FasL C82A. In some embodiments, an immune cell e.g., a T cell of the present disclosure comprises and/or expresses a nucleic acid e.g., a vector that encodes FasL SLEKQ→EEAAA (SEQ ID NOs: 32 and 33, respectively). In some embodiments, an immune cell e.g., a T cell of the present disclosure comprises and/or expresses a nucleic acid e.g. a vector that encodes FasL Q130D.

The present disclosure encompasses modifications to the proteins of the disclosed embodiments shown in Table 1, including functionally equivalent proteins having modifications which do not significantly affect their properties and variants which have enhanced or decreased activity and/or affinity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag.

Substitution variants have at least one amino acid residue in the protein removed and a different residue inserted in its place. Conservative substitutions are shown in Table 3 under the heading of "conservative substitutions." If such substitutions result in a change in biological activity, then more substantial changes, denominated "exemplary substitutions" in Table 3, or as further described below in reference to amino acid classes, may be introduced and the products screened.

TABLE 3

Amino Acid Substitutions

| Original residue (naturally occurring amino acid) | Conservative substitutions | Exemplary subsitutions |
|---|---|---|
| Ala (A) | Val | Val; Leu; He |
| Arg (R) | Lys | Lys; Gin; Asn |
| Asn (N) | Gln | Gln; His; Asp; Lys; Arg |
| Asp (D) | Glu | Glu; Asn |
| Cys (C) | Ser | Ser; Ala |
| Gln (Q) | Asn | Asn; Glu |

TABLE 3-continued

Amino Acid Substitutions

| Original residue (naturally occurring amino acid) | Conservative substitutions | Exemplary subsitutions |
|---|---|---|
| Glu (E) | Asp | Asp; Gin |
| Gly (G) | Ala | Ala |
| His (H) | Arg | Asn; Gin; Lys; Arg |
| He (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

FasL protein and FasL protein derivatives may be synthesized in situ in the cell after introduction of polynucleotides encoding the viral proteins into the cell. Alternatively, FasL protein and FasL protein derivative proteins may be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g., retroviruses e.g., lentiviruses, adenoviruses), liposomes, and the like. Transient transformation methods include, for example without limitation, microinjection, electroporation or particle bombardment. Polynucleotides may be included in vectors, such as for example plasmid vectors or viral vectors.

In some embodiments, an engineered immune cell e.g., a T cell of the present disclosure can comprise at least one FasL protein or FasL protein derivative and at least one CAR. In some embodiments, the engineered immune cell e.g., a T cell is modified e.g., genetically modified to express a reduced level of FasR. In some embodiments, an engineered immune cell e.g., a T cell can comprise at least one FasL protein or FasL protein derivative and two or more different antigen binding proteins, e.g., two or more different CARs, each CAR comprising different extracellular ligand-binding domains.

In some embodiments of an engineered immune cell e.g, a. T cell provided herein, a CAR can comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

The extracellular ligand-binding domain specifically binds to a target of interest. In some embodiments, the target of interest can be any molecule of interest, including, for example, without limitation, BCMA, EGFRvIII, Flt-3, WT-1, CD20, CD23, CD30, CD38, CD70, CD33, CD133, MHC-WT1, TSPAN10, MHC-PRAME, Liv1, ADAM10, CHRNA2, LeY, NKG2D, CS1, CD44v6, ROR1, CD19, Claudin-18.2 (Claudin-18A2, or Claudin18 isoform 2), DLL3 (Delta-like protein 3, *Drosophila* Delta homolog 3, Delta3), Muc 7 (Mucin17, Muc3, Muc3), FAP alpha (Fibroblast Activation Protein alpha), Ly6G6D (Lymphocyte antigen 6 complex locus protein G6d, c6orf23, G6D, MEGT1, NG25), RNF43 (E3 ubiquitin-protein ligase RNF43, RING finger protein 43).

In some embodiments, the extracellular ligand-binding domain comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988). Examples of a linking peptide is the GS linker having the amino acid sequence (GGGGS)$_3$ (SEQ ID NO: 36) or (GGGGS)$_4$ (SEQ ID NO: 37) or GST-SGSGKPGSGEGSTKG (SEQ ID NO: 38), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid or other vector containing a polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The intracellular signaling domain of a CAR according to the disclosure is responsible for intracellular signaling following the binding of extracellular ligand-binding domain to the target resulting in the activation of the immune cell and immune response. The intracellular signaling domain has the ability to activate at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs or ITAMs. ITAMs are well defined signaling motifs found in the intracytoplasmic tail of a variety of receptors that serve as binding sites for syk/zap70 class tyrosine kinases. Examples of ITAM used in the CAR disclosed herein can include as non-limiting examples those derived from TCRζ, FcRγ, FcRβ, FcRε, CD3γ, CD3ε, CD3δ, CD5, CD22, CD79a, CD79b and CD66d. In some embodiments, the intracellular signaling domain of the CAR can comprise the CD3 signaling domain. In some embodiments, the intracellular signaling domain of the CAR of the present disclosure comprises a domain of a co-stimulatory molecule.

In some embodiments, the intracellular signaling domain of a CAR of the present disclosure comprises a part of a co-stimulatory molecule selected from the group consisting of a fragment of 41BB (GenBank: AAA53133) a fragment of CD28 (NP_006130.1) a fragment of OX40, a fragment of CD40, or a fragment of CD27.

CARs are expressed on the surface membrane of the cell. Thus, the CAR can comprise a transmembrane domain. Suitable transmembrane domains for a CAR disclosed herein have the ability to (a) be expressed at the surface of a cell, for example an immune cell such as, for example without limitation, lymphocyte cells (e.g., T cells) or Natural killer (NK) cells, and (b) interact with the ligand-binding domain and intracellular signaling domain for directing a cellular response of an immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a domain of the T cell receptor such as α, β, γ or δ, polypeptide constituting CD3 complex, IL-2 receptor e.g., p55 (α chain), p75 (β chain or γ chain), subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8a chain (e.g., NP_001139345.1). The transmembrane domain can further comprise a stalk domain between the extracellular ligand-binding domain and said transmembrane domain. A stalk domain may comprise up to 300 amino acids, for example, from 10 to 100 amino acids or 25 to 50 amino acids. The stalk region may be derived from all or part of naturally occurring molecules, such as from all or part of the extracellular region of CD8, CD4, or CD28, or from all or part of an antibody constant region. Alternatively, the stalk domain may be a synthetic sequence that corresponds to a naturally occurring stalk sequence or can be an entirely synthetic stalk sequence. In some embodiments said stalk domain is a part of human CD8α chain (e.g., NP_001139345.1). In another particular embodiment, the transmembrane domain comprises a part of the human CD8a chain. In some embodiments, CARs disclosed herein can comprise an extracellular ligand-binding domain that specifically binds BCMA, CD8a human stalk and transmembrane domains, the CD3t signaling domain, and 4-1BB signaling domain. In some embodiments, a CAR can be introduced into an immune cell as a transgene via a vector e.g., a plasmid vector. In some embodiments, the vector e.g. plasmid vector can also contain, for example, a selection marker which provides for identification and/or selection of cells which received the vector.

CAR polypeptides may be synthesized in situ in the cell after introduction of polynucleotides encoding the CAR polypeptides into the cell. Alternatively, CAR polypeptides may be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g., retroviruses (e.g., lentiviruses), adenoviruses), liposomes, and the like. Transient transformation methods include, for example without limitation, microinjection, electroporation or particle bombardment. Polynucleotides may be included in vectors, such as for example plasmid vectors or viral vectors.

Also provided herein are immune cells e.g., T cells such as isolated T cells obtained according to any one of the methods described herein. Any immune cell capable of expressing heterologous DNAs can be used for the purpose of expressing the FasL protein or FasL protein derivative and the CAR of interest. In some embodiments, the immune cell is a T cell. In some embodiments, an immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The isolated cell can also be a dendritic cell, killer dendritic cell, a mast cell, a NK– cell, a B-cell or a T cell selected from the group consisting of inflammatory T-lymphocytes, cytotoxic T-lymphocytes, regulatory T-lymphocytes or helper T-lymphocytes. In some embodiments, the cell can be derived from the group consisting of CD4+ T-lymphocytes and CD8+ T-lymphocytes. In some embodiments, the immune cells e.g. T cells such as isolated T cells are further modified e.g. genetically modified using any gene mutation or gene editing technique, including but not limited to known homologous recombination techniques and techniques that employ any one or more of meganucleases, TALEN, zinc fingers, shRNA, Cas-CLOVER, and a CRISPR/Cas system to, e.g., partially or wholly delete the FasR gene locus, and/or using one or more known knockdown methods e.g. those that employ any of various RNA-based techniques (e.g. anti-sense RNA, miRNA, siRNA) so that they express a reduced level of FasR relative to comparable cells not so modified.

A second aspect of the disclosure is an immune cell e.g. a T cell that is modified so that it expresses FasR at a reduced level (e.g. by genetically modifying the cell using any gene mutation or gene editing technique, including but not limited to known homologous recombination techniques and techniques that employ any one or more of meganucleases, TALEN, zinc fingers, shRNA, Cas-CLOVER, and a CRISPR/Cas system to, e.g., partially or wholly delete the FasR gene locus). In embodiments of both aspects, the immune cell e.g., a T cell, is further modified so that it comprises and/or expresses an antigen binding protein e.g., a chimeric antigen receptor (CAR) (e.g., from an expression vector comprising a polynucleotide that encodes the antigen binding protein e.g. CAR).

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a subject diagnosed with cancer or from a subject diagnosed with an infection. In some embodiments, cells can be part of a mixed population of cells which present different phenotypic characteristics.

Also provided herein are cell lines obtained from a modified e.g. transformed immune cell e.g. T cell according to any of the methods described herein. In some embodiments, an immune cell e.g., a T cell according to the present disclosure comprises a polynucleotide encoding a FasL protein or FasL protein derivative. In some embodiments, an immune cell e.g., a T cell according to the present disclosure comprises a polynucleotide encoding a FasL protein or FasL protein derivative and a polynucleotide encoding a CAR. In some embodiments, an immune cell e.g., a T cell according to the present disclosure comprises a polynucleotide encoding a FasL protein or FasL protein derivative, a polynucleotide encoding a CAR, and is modified e.g., genetically modified, so that it expresses FasR at a reduced level.

The immune cells, e.g., T cells of the present disclosure can be activated and expanded, either prior to or after modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. Immune cells, e.g., T cells can be expanded in vitro or in vivo. Generally, the immune cells of the present disclosure can be expanded, for example, by contact with an agent that stimulates a CD3 TCR complex and a co-stimulatory molecule on the surface of the immune cells to create an activation signal for the cell. For example, chemicals such as calcium ionophore A23187, phorbol 12-myristate 13-acetate (PMA), or mitogenic lectins like phytohemagglutinin (PHA) can be used to create an activation signal for the immune cell e.g., T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate medium (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, a TGFβ, and TNF, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM V, DMEM, MEM, α-MEM, F-12, X-Vivo 10, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). Immune cells e.g. T cells that have been exposed to varied stimulation times may exhibit different characteristics.

In some embodiments, the cells of the present disclosure can be expanded by co-culturing with tissue or cells. The cells can also be expanded in vivo, for example in the subject's blood after administrating the cell into the subject.

In another aspect, the present disclosure provides compositions (such as pharmaceutical compositions) comprising any of the cells disclosed herein. In some embodiments, the composition comprises a T cell comprising a polynucleotide encoding a FasL protein or FasL protein derivative and a polynucleotide encoding an antigen binding protein e.g. CAR. In some embodiments, the cell is modified to express a reduced level of FasR. The compositions comprise, for example, an immune cell e.g. T cell of the present disclosure, e.g. an immune cell that expresses an antigen binding protein e.g. a CAR and a FasL protein and/or FasL protein derivative, and optionally that functionally expresses FasR at a reduced level relative to comparable cells not modified with respect to FasR expression level, or comprise a population of cells that comprises an immune cell e.g. T cell of the present disclosure, and one or more pharmaceutically acceptable carriers or excipients.

In some embodiments, primary cells isolated from a donor are manipulated as described herein to provide a population of cells of which a subpopulation (e.g., a proportion less than 100%, such as 10%, 20%, 30%) of the resulting cells comprise all or a fraction of the desired modifications. Such a resulting population comprising a mixture of cells that comprise all or a fraction of the modifications and cells that do not can be used in the methods of treatment of the present disclosure and to prepare the compositions of the present disclosure. Alternatively, this population of cells (the "starting population") can be manipulated by known methods e.g. cell sorting and/or expansion of cells that have the desired modifications, to provide a population of cells that is enriched for those cells comprising one or more of the desired modifications (e.g., enriched for cells that express the desired antigen binding protein, for cells that express a FasL protein and/or FasL protein derivative, and/or enriched for cells that express FasR at a reduced level relative to comparable cells not modified with respect to FasR expression level), that is, that comprises a higher percentage of such modified cells than did the starting population. The population enriched for the modified cells can then be used in the methods of treatment disclosed herein and to prepare the compositions of the present disclosure, for example. In some embodiments, the enriched population of cells contains or contains at least 40%, 50%, 60%, 70%, 80%, 90%, 95%, or 99% cells that have one or more of the modifications. In other embodiments, the proportion of cells of the enriched population of cells that comprise one or more of the modifications is at least 30% higher than the proportion of cells of the starting population of cells that comprise the desired modifications.

Methods of Treating

Immune cells, e.g., T cells obtained by the methods described above, or cell lines derived from such immune cells or T cells, can be used as a medicament. In some embodiments, such a medicament can be used for treating a disorder such as for example a viral disease, a bacterial disease, a cancer, an inflammatory disease, an immune disease, or an aging-associated disease. In some embodiments, the cancer can be selected from the group consisting of gastric cancer, sarcoma, lymphoma, leukemia, head and neck cancer, thymic cancer, epithelial cancer, salivary cancer, liver cancer, stomach cancer, thyroid cancer, lung cancer, ovarian cancer, breast cancer, prostate cancer, esophageal cancer, pancreatic cancer, glioma, leukemia, multiple myeloma, renal cell carcinoma, bladder cancer, cervical cancer, choriocarcinoma, colon cancer, oral cancer, skin cancer, and melanoma. In some embodiments, the subject is a previously treated adult subject with locally advanced or metastatic melanoma, squamous cell head and neck cancer (SCHNC), ovarian carcinoma, sarcoma, or relapsed or refractory classic Hodgkin's Lymphoma (cHL).

In some embodiments, immune cells e.g. T cells according to the present disclosure, or a cell line derived from the immune cells e.g. T cells, can be used in the manufacture of a medicament for treatment of a disorder in a subject in need thereof. In some embodiments, the disorder can be, for example, a cancer, an autoimmune disorder, or an infection.

In certain embodiments, the FasR functional expression level, or the functional expression level of any other gene that is knocked down or knocked out according to the present disclosure, in an engineered immune cell of this disclosure is decreased by or by at least about 25%, 30%, 35%, 40%, 45%, 50%, 55%, 60%, 65%, 70%, 75%, 80%, 85%, 90%, 95%, 99%, or 100% relative to the corresponding expression level in a non-genetically-modified engineered immune cell. In some embodiments, the engineered immune cell disclosed herein functionally expresses FasR, or any other gene that is knocked down or knocked out according to the present disclosure, at a level not greater than 75%, not greater than 50%, not greater than 25%, not greater than 10% or at a level of 0% of the expression level in non-engineered immune cells that otherwise are the same as the engineered immune cells, e.g. comprise the same components as the engineered immune cells. In some embodiments, both alleles of one gene are knocked out, so that gene's expression level in the engineered immune cell disclosed herein is 0% of that of a corresponding non-engineered cell. In some embodiments, one of the two alleles of a gene is knocked out, so that gene's expression level in the engineered immune cell disclosed herein is 50% or about 50% (e.g. if a compensatory mechanism causes greater than normal expression of the remaining allele) of that of a corresponding non-engineered cell. Intermediate levels of expression may be observed if, for example, expression is reduced by some means other than knock-out, as described herein. In some embodiments, a population of engineered immune cells of the invention comprises a mixture of cells wherein some of the cells have both alleles altered or knocked out, some of the cells have only one allele altered or knocked out, and/or some of the cells have neither an allele altered or knocked out.

In some embodiments, the FasR expression level, or of any other gene the expression level of which is manipulated according to the present disclosure, in the engineered cells of the present disclosure may be measured directly by assaying the cells for gene products and their properties using standard techniques known to those of skill in the art (e.g. RT-qPCR, nucleic acid sequencing, antibody staining, or some combination of techniques). In some embodiments, the functional expression level of FasR is measured by determining the expression level of FasR on the surface of the engineered immune cell by standard techniques known in the art, e.g. flow cytometry. These measurements may be compared to corresponding measurements made on comparable cells that have not been engineered to reduce the functional expression level of FasR. In a population of cells that comprises an engineered cell e.g. engineered immune cell of the invention, a pooled sample of the material being measured, e.g. RNA or protein or cells, will reflect the fact that some of the cells do not express the gene of interest, having had both alleles knocked out, for example, some of the cells express the gene of interest at 50% or about 50% relative to corresponding non-engineered cells, having had only one allele knocked out, and, if the population comprises non-engineered cells, that some of the cells express a normal level of the gene of interest.

The functional expression level of FasR expression in engineered immune cells of the present disclosure may also be assayed, for example, by measuring the degree to which the engineered immune cells survive in the presence of effector cells, e.g., T cells or NK cells, in comparison to the degree to which non-engineered, but otherwise comparable e.g. identical, immune cells survive under the same conditions.

In some embodiments, administering an engineered immune cell, e.g. an engineered T cell as disclosed herein, or administering a population of cells comprising such engineered immune cells e.g. engineered T cells, reduces host rejection of the administered cell or population of cells relative to a comparable but non-engineered cell or comparable population that does not comprise such engineered cells. In some embodiments, administering an engineered immune cell, e.g., an engineered T cell of this disclosure comprising an antigen binding protein, e.g., a CAR and in which FasR expression level is reduced, or administering a population of cells comprising such engineered immune cells e.g. engineered T cells, reduces host rejection of the administered cell or population of cells relative to a comparable but non-engineered cell or population that does not comprise such engineered cells. For example, such administration reduces host rejection by between 1% and 99%, e.g. between 5% and 95%, between 10% and 90%, between 50% and 90%, e.g. by 10%, 20%, 30%, 40%, 50%, 60%, 70%, 80%, or 90% as compared to host rejection of cells that are the same but which are not engineered to express FasR at a reduced level. In some embodiments, host rejection is reduced by over 90%.

In some embodiments, administering an immune cell e.g., a T cell of this disclosure comprising an antigen binding protein, e.g., a CAR and in which FasR functional expression level is reduced, or administering a population of cells comprising such immune cells, e.g., T cells, enhances or improves the persistence and/or increases the persistence of the cells as compared to the persistence of cells that are the same but which are not engineered to express FasR at a reduced level. In some embodiments, persistence is increased by, for example, between 1 and 7 days, by between 1 and 12 weeks (e.g., between 1 and 4 weeks, 4 and 8 weeks, or 8 and 12 weeks), or by between 1 and 12 months, or by a specific length of time that falls within these ranges. In some embodiments, the difference in persistence is measured by comparing the half-life of the administered cells in the population or composition, wherein, for example, the half-life is increased by, for example, between 1 and 7 days, by between 1 and 12 weeks (e.g. between 1 and 4 weeks, 4 and 8 weeks, or 8 and 12 weeks), or by between 1 and 12 months, or by a specific length of time that falls within these ranges. In some embodiments, the difference in persistence is measured by comparing the length of time that the administered cells can be detected after administration. In some embodiments, the improvement in persistence is measured in vitro by comparing the survival of engineered and non-engineered cells in the presence of, for example, immune cells such as T cells or NK cells, e.g., at about 72 hours, 5 days, or 7 days after mixing. In some embodiments, in such an in vitro assay, between about 1.5 and 10 times as many engineered cells survive as do cells that are not engineered at the time of measurement.

In some embodiments, reduction in host rejection and/or increases in persistence of administered cells as disclosed herein are determined by any of a variety of techniques known to the person of ordinary skill in the art. In some embodiments, any one or a combination of the following is use: flow cytometry, PCR e.g. quantitative PCR, and ex vivo coincubation with patient tumor material or with a model tumor cell line expressing the antigen targeted by the CAR-T cell. In some embodiments, qPCR is used to assess the number of CAR T cells that have and do not have the knock-out of interest in order to determine the extent to which the knock-out provides a survival advantage.

In some embodiments, the immune cells e.g., T cells provided herein can be administered parenterally in a subject. In some embodiments, the subject is a human.

In some embodiments, the method can further comprise administering an effective amount of a second therapeutic agent. In some embodiments, the second therapeutic agent is, for example, crizotinib, palbociclib, an anti-CTLA4 antibody, an anti-4-1 BB antibody, a PD-1 antibody, or a PD-L1 antibody.

Also provided is the use of any of the immune cells e.g. T cells provided herein in the manufacture of a medicament for the treatment of cancer or for inhibiting tumor growth or progression in a subject in need thereof.

In certain embodiments, the FasR expression level in a genetically-modified engineered immune cell of the present disclosure is decreased by or by at least about 30%, 35%, 40%, 45%, 50%, 55%, 60%, 65%, 70%, 75%, 80%, 85%, 90%, 95%, 99%, or 100% relative to the FasR expression level in a non-genetically-modified engineered immune cell. In some embodiments, the FasR expression level is measured at the cell surface. In some embodiments, cell surface expression levels of FasR may be measured by flow cytometry. Surface FasR can be measured by binding of a fluorescently labeled anti-FasR/CD95 antibody and flow cytometry to determine mean fluorescence intensity on a per-cell basis across a population of cells. KO efficiency was roughly 50% with KO cells exhibiting 1-2 logs lower fluorescence intensity for FasR staining.

In some embodiments, administering an immune cell e.g. T cell of the present disclosure comprising an antigen binding protein e.g. a CAR and a FasL protein or FasL protein derivative and in which FasR expression level is reduced, or administering a population of cells comprising such immune cells e.g. T cells, reduces AICD and/or rejection by between 10% and 90%, e.g. by between 50% and 90%, e.g. by 10%, 20%, 30%, 40%, 50%, 60%, 70%, 80%, or 90% as compared to AICD in cells that are the same but which do not comprise a FasL protein or FasL protein derivative and in which FasR expression level is not reduced. In some embodiments, host cell killing e.g. activation-induced cell death (AICD) is reduced by over 90%. Assays to assess AICD include a repetitive stimulation in vitro assay (e.g., repeated addition of target tumor cells) or in vivo tumor xenograft assays, particularly with FasL-expressing tumors.

In some embodiments, administering an immune cell e.g. T cell of the present disclosure comprising an antigen binding protein e.g. a CAR and a FasL protein or FasL protein derivative and in which FasR expression level is reduced, or administering a population of cells comprising such immune cells, e.g., T cells, enhances or improves the persistence and/or increases the persistence of the cells as compared to the persistence of cells that are the same but which do not comprise a FasL protein or FasL protein derivative and in which FasR expression level is not reduced. In some embodiments, persistence is increased by between 25% and 100%, e.g. by, or by at least, 50%, 60%, 70%, 80%, 90%, 95%, 99%, or 100%, or by a percentage that falls within a range whose endpoints are any two of the recited percentages. In some embodiments, the difference in persistence is measured by comparing the half-life of the administered cells in the population or composition, wherein, for example, the half-life is increased by or by at least 10%, 20%, 30%, 40%, 50%, 75%, 100%, or 200%, or by a percentage that falls within a range whose endpoints are any two of the recited percentages. In some embodiments, the difference in persistence is measured by comparing the length of time that the administered cells can be detected after administration. In some embodiments, the improvement in persistence is measured in vitro by comparing the percentage of cells remaining at a certain time after mixing the cells with activated NK cells, e.g., at about 72 hours, 5 days, or 7 days after mixing. In some embodiments, in such an in vitro assay, between about 1.5 and 10 times as many cells comprising an active FasL protein or FasL protein derivative survive as do cells that do not comprise an active FasL protein or FasL protein derivative (e.g., cells that do not comprise an active FasL protein or FasL protein derivative or that comprise an inactive FasL protein or FasL protein derivative).

In some embodiments, the treatment can be in combination with one or more therapies against cancer selected from the group of antibodies therapy, chemotherapy, cytokines therapy, dendritic cell therapy, gene therapy, hormone therapy, laser light therapy and radiation therapy.

In some embodiments, treatment can be administered to or administrated into subjects undergoing an immunosuppressive treatment. Indeed, the subject matter disclosed herein may rely on cells or a population of cells which have been made resistant to at least one immunosuppressive agent due to the inactivation of a gene encoding a receptor for such immunosuppressive agent. In this aspect, the immunosuppressive treatment may help the selection and expansion of the immune cells, e.g., T cells according to the present disclosure within the subject.

The administration of the cells or population of cells according to the present disclosure may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. In one embodiment, the cell compositions of the present disclosure are administered by intravenous injection.

In some embodiments, the administration of the cells or population of cells can comprise administration of, for example, about $10^4$ to about $10^9$ cells per kg body weight including all integer values of cell numbers within those ranges. In some embodiments the administration of the cells or population of cells can comprise administration of about $10^5$ to about $10^6$ cells per kg body weight including all integer values of cell numbers within those ranges. The cells or population of cells can be administered in one or more doses. In some embodiments, an effective amount of cells can be administered as a single dose. In some embodiments, an effective amount of cells can be administered as more than one dose over a period time. Timing of administration is within the judgment of the managing physician and depends on the clinical condition of the subject. The cells or population of cells may be obtained from any source, such as a blood bank or a donor. While individual needs vary, determination of optimal ranges of effective amounts of a given cell type for a particular disease or conditions is within the skill of the art. An effective amount means an amount which provides a therapeutic or prophylactic benefit. The dosage administered will be dependent upon the age, health and weight of the recipient, the kind of concurrent treatment, if any, the frequency of treatment and the nature of the effect desired. In some embodiments, an effective amount of cells or composition comprising those cells are administered parenterally. In some embodiments, administration can be an intravenous administration. In some embodiments, administration can be directly done by injection within a tumor.

In some embodiments of the present disclosure, cells are administered to a subject in conjunction with (e.g., before, simultaneously or following) any number of relevant treatment modalities, including but not limited to treatment with agents such as monoclonal antibody therapy, CCR2 antagonist (e.g., INC-8761), antiviral therapy, cidofovir and interleukin-2, Cytarabine (also known as ARA-C) or nataliziimab treatment for MS subjects or efaliztimab treatment for psoriasis subjects or other treatments for PML subjects. In some embodiments, BCMA specific CAR-T cells are administered to a subject in conjunction with one or more of the following: an anti-PD-1 antibody (e.g., nivolumab, pembrolizumab, or PF-06801591), an anti-PD-L1 antibody (e.g., avelumab, atezolizumab, or durvalumab), an anti-OX40 antibody (e.g., PF-04518600), an anti-4-1 BB antibody (e.g., PF-05082566), an anti-MCSF antibody (e.g., PD-0360324), an anti-GITR antibody, and/or an anti-TIGIT antibody. In further embodiments, the immune cells e.g. T cells of the present disclosure may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin) (Henderson, Naya et al. Immunology. 1991 July; 73(3): 316-321; Liu, Albers et al. Biochemistry 1992 Apr. 28; 31(16):3896-901; Bierer, Hollander et al. Curr Opin Immunol. 1993 Oct.; 5(5):763-73).

In a further embodiment, the cell compositions of the present disclosure are administered to a subject in conjunction with (e.g., before, simultaneously or following) bone marrow transplantation, T cell ablative therapy using either chemotherapy agents such as fludarabine, external-beam radiation therapy (XRT), cyclophosphamide, or antibodies such as OKT3 or CAMPATH. In some embodiments, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of expanded immune cells of the present disclosure. In some embodiments, expanded cells are administered before or following surgery.

Kits

The present disclosure also provides kits for use in the instant methods. Kits disclosed herein include one or more containers comprising a composition of the present disclosure or an immune cell e.g. a T cell of the present disclosure or a population of cells comprising an immune cell, e.g., a T cell of the present disclosure. In various embodiments, the immune cell, e.g., a T cell, comprises one or more polynucleotide(s) encoding FasL protein or a FasL protein derivative and an antigen binding protein, e.g., a CAR as described herein, and further is modified to express a reduced level of FasR as described herein. The kit further comprises instructions for use in accordance with any of the methods disclosed herein. Generally, these instructions comprise a description of administration of the composition, immune cell, e.g., a T cell or population of cells for the above-described therapeutic treatments.

The instructions relating to the use of the kit components generally include information as to dosage, dosing schedule, and route of administration for the intended treatment. The containers may be unit doses, bulk packages (e.g., multidose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an immune cell e.g. T cell according to the present disclosure, or a population of such cells. The container may further comprise a second pharmaceutically active agent.

Kits may optionally provide additional components such as buffers and interpretive information. Normally, the kit comprises a container and a label or package insert(s) on or associated with the container.

Methods of Sorting and Depletion

In some embodiments, provided are methods for in vitro sorting of a population of immune cells, wherein a subset of the population of immune cells comprises immune cells engineered as described herein to express FasR at a reduced level and/or express an antigen binding protein e.g. a CAR. The method comprises contacting the population of immune cells with a monoclonal antibody specific for an epitope (e.g. mimotope) unique to the engineered cell, e.g. an epitope of the antigen binding protein or a mimotope incorporated into the antigen binding protein, and selecting the immune cells that bind to the monoclonal antibody to obtain a population of cells enriched in engineered immune cells that express the antigen binding protein.

In some embodiments, said monoclonal antibody specific for said epitope is optionally conjugated to a fluorophore. In this embodiment, the step of selecting the cells that bind to the monoclonal antibody can be done by Fluorescence Activated Cell Sorting (FACS).

In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the mAb used in the method for sorting immune cells expressing the antigen binding protein e.g. CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10.

In some embodiments, the population of CAR-expressing immune cells obtained when using the method for in vitro sorting CAR-expressing immune cells described above, comprises at least 70%, 75%, 80%, 85%, 90%, 95% of CAR-expressing immune cells. In some embodiments, the population of CAR-expressing immune cells obtained when using the method for in vitro sorting CAR-expressing immune cells, comprises at least 85% CAR-expressing immune cells.

In some embodiments, the population of CAR-expressing immune cells obtained when using the method for in vitro sorting CAR-expressing immune cells described above shows increased cytotoxic activity in vitro compared with the initial (non-sorted) cell population. In some embodiments, said cytotoxic activity in vitro is increased by 10%, 20%, 30% or 50%. In some embodiments, the immune cells are T-cells.

The CAR-expressing immune cells to be administered to the recipient may be enriched in vitro from the source population. Methods of expanding source populations may include selecting cells that express an antigen such as CD34 antigen, using combinations of density centrifugation, immuno-magnetic bead purification, affinity chromatography, and fluorescent activated cell sorting.

Flow cytometry may be used to quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometry analysis involves two primary steps: 1) labeling selected cell types with one or more labeled markers, and 2) determining the number of labeled cells relative to the total number of cells in the population. In some embodiments, the method of labeling cell types includes binding labeled antibodies to markers expressed by the specific cell type. The antibodies may be either directly labeled with a fluorescent compound or indirectly labeled using, for example, a fluorescent-labeled second antibody which recognizes the first antibody.

In some embodiments, the method used for sorting T cells expressing CAR is the Magnetic-Activated Cell Sorting (MACS). Magnetic-activated cell sorting (MACS) is a method for separation of various cell populations depending on their surface antigens (CD molecules) by using super-paramagnetic nanoparticles and columns. MACS may be used to obtain a pure cell population. Cells in a single-cell suspension may be magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a washing step, the column is removed from the separator, and the magnetically labeled cells are eluted from the column.

A detailed protocol for the purification of a specific cell population such as T-cells can be found in Basu S et al. (2010). (Basu S, Campbell H M, Dittel B N, Ray A. Purification of specific cell population by fluorescence activated cell sorting (FACS). J Vis Exp. (41): 1546).

EXAMPLES

The following examples are offered for illustrative purposes only, and are not intended to limit the scope of the present disclosure in any way. Indeed, various modifications of the present disclosure in addition to those shown and described herein will become apparent to those skilled in the art from the foregoing description and fall within the scope of the appended claims.

Example 1: Validation of FasR Expression on Activated T and NK Cells

Two experiments were performed to confirm that alloreactive T and NK cells will be susceptible to FasL-mediated killing upon activation.

A. In the first experiment, primary T cells were repeatedly stimulated with TransAct in the presence of 100 U/mL IL-2 for up to eight days prior to evaluating activation-induced cell death (via 7-aminoactinomycin D (7-AAD)) and surface expression of FasR and CD69 (see FIGS. 1A-1C). Unstimulated T cells were negative for CD69, approximately 40% FasR+, and exhibited high viability upon thawing. A single stimulation resulted in >80% of cells expressing CD69, >95% of cells expressing FasR, and minimal loss of viability.

Figure 1B:
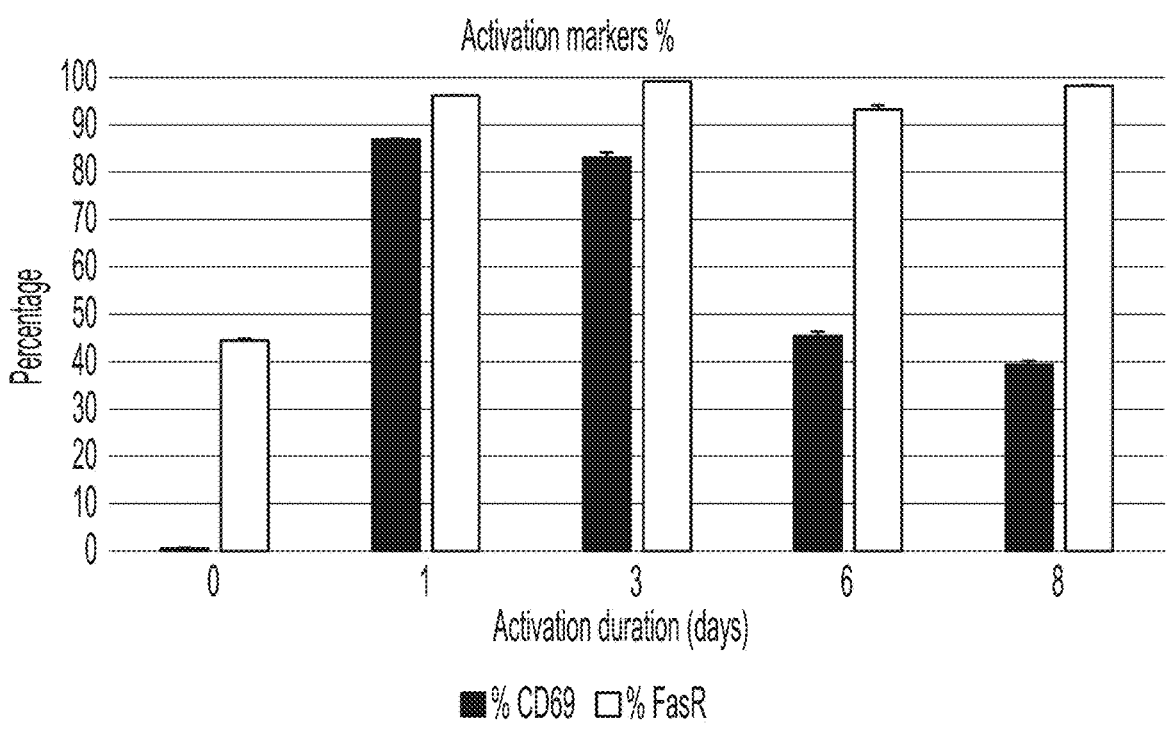
Figure 1C:
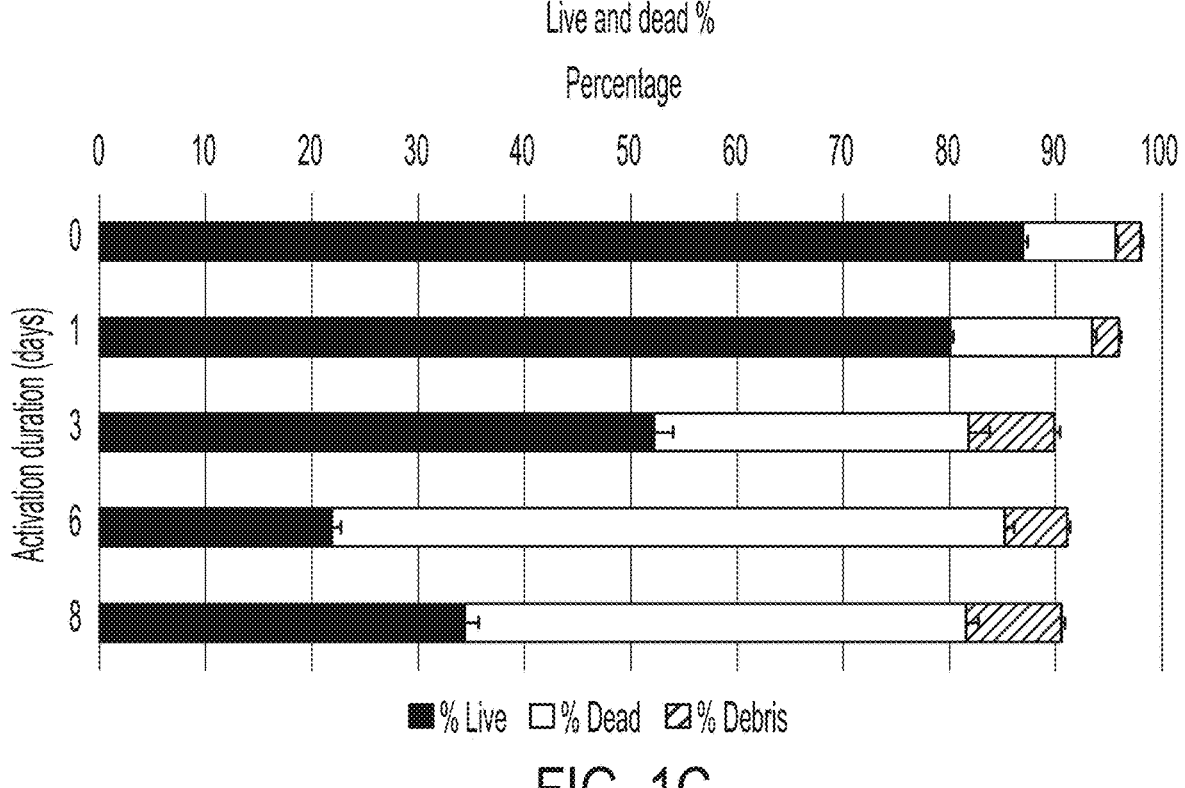

Repeated stimulation—modeling serial killing of cancer cells by a CAR T cell over a course of therapy—resulted in gradual decline of CD69+ cells to about 40%, stable expression of FasR on >95% of cells, and profound (~70-80%) cell death (see FIGS. 1A-1C). Based on these results, activated T cells (including alloreactive T cells attacking cell therapies) should be susceptible to FasL-mediated killing by FasCAR T cells. Additionally, it is expected based on these results that FasR knockout in FasCAR T cells will be necessary to prevent FasL-mediated fratricide and may improve resistance to AICD pursuant to tumor cell engagement.

Figure 2:
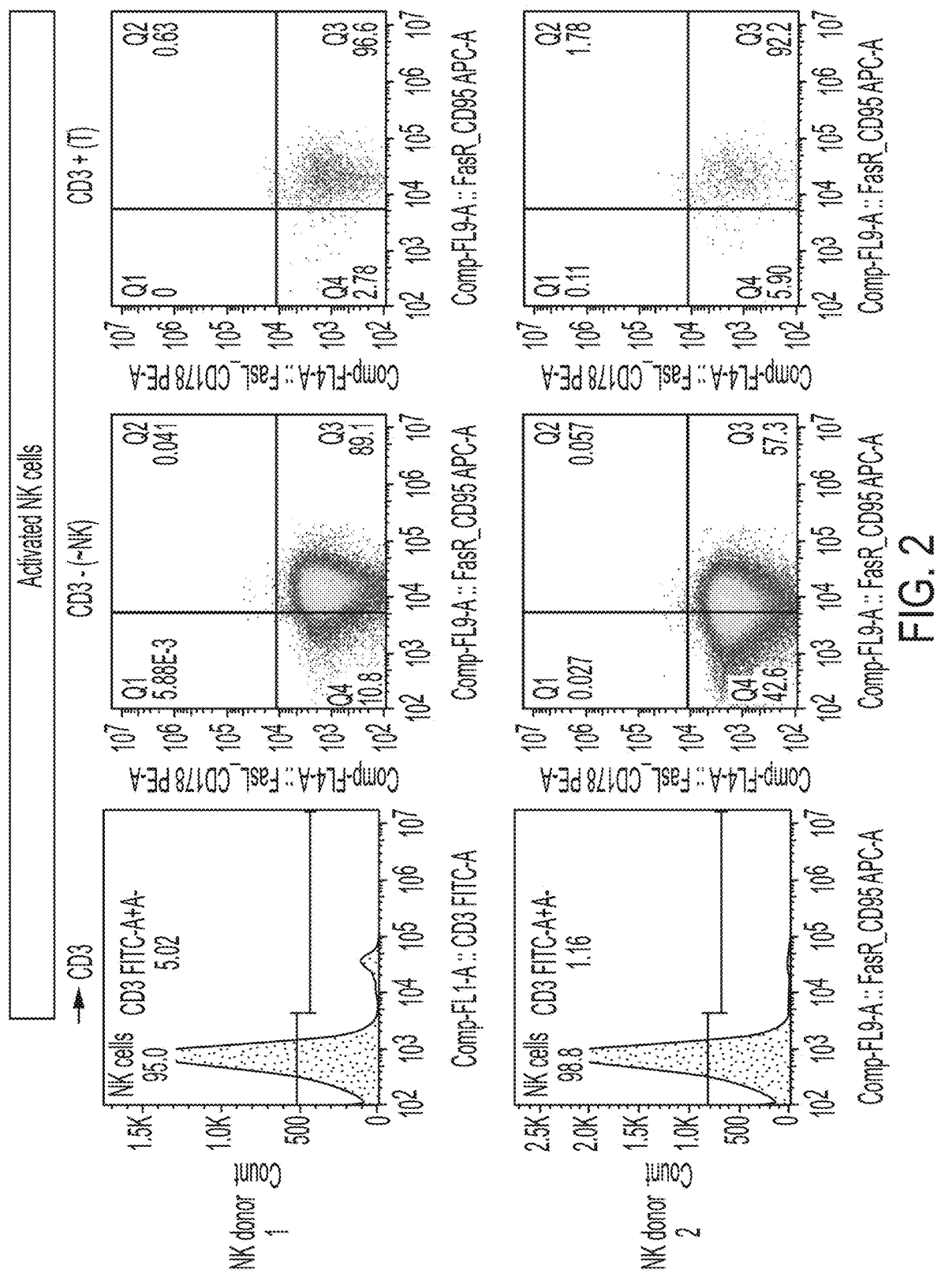
FIG. 2. Cytokine activated NK cells express FasR. NK cells were purified from LRS chambers collected from three donors, activated for 48 hours with 1000 U/mL IL-2 and then surface expression of FasR was evaluated by flow cytometry. Results are compared to FasR⁺ T cells stimulated with TransAct and then expanded for two weeks in the presence of 100 U/mL IL-2.
Figure 2:
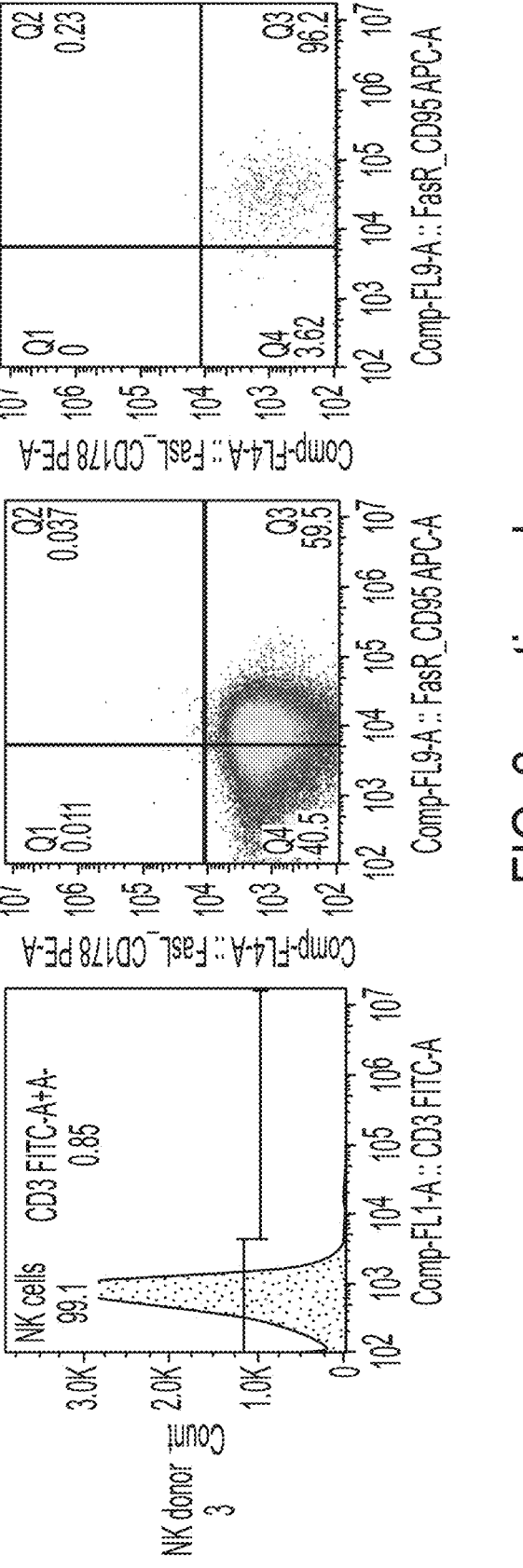
Figure 2:
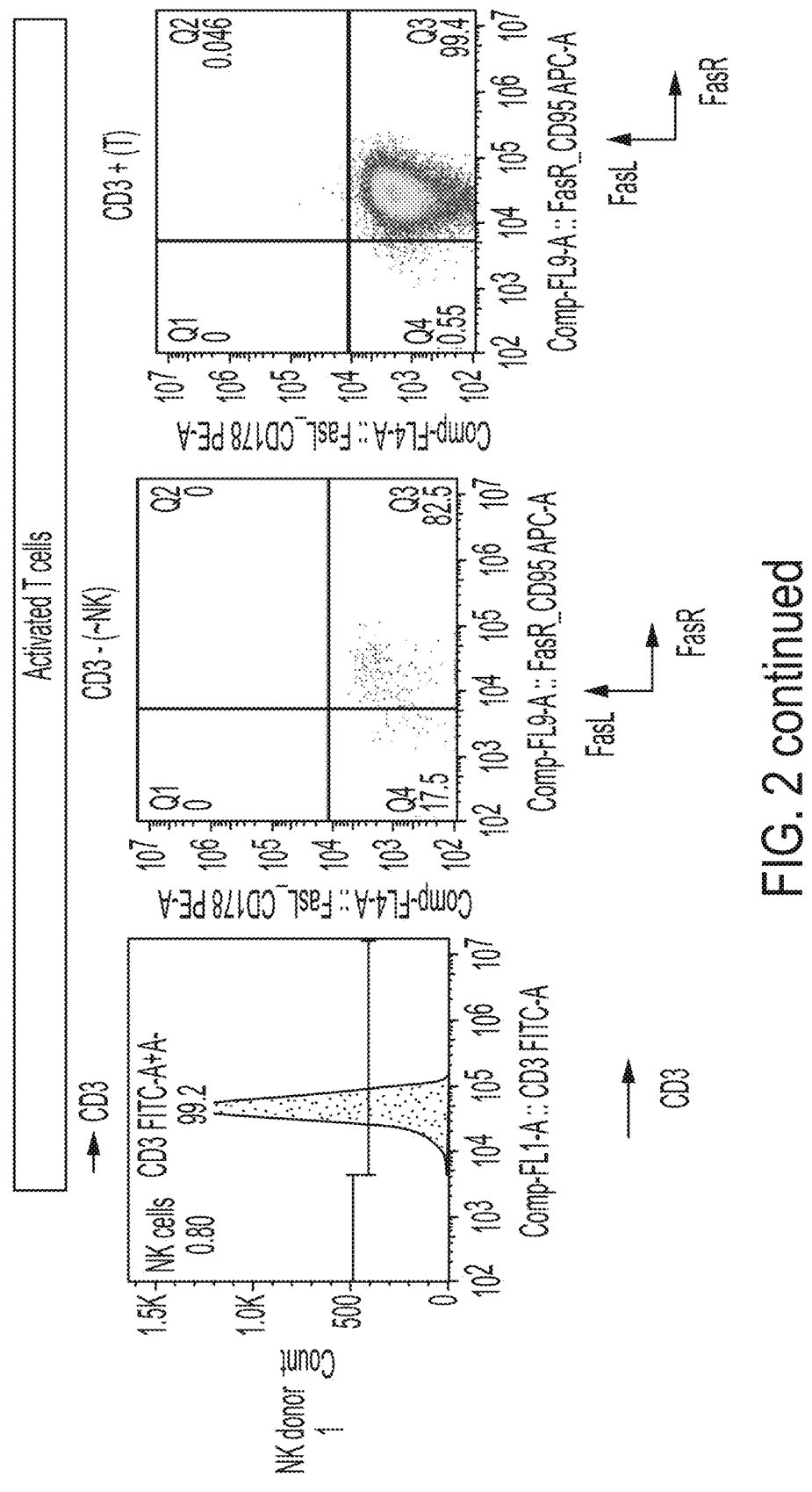

B. In the second experiment, NK cells prepared from freshly collected leukoreduction system (LRS) chambers were activated for 48 hours with 1000 U/mL IL-2 and then their FasR expression was compared to activated FasR+ T cells by flow cytometry (FIG. 2). Cytokine activated NK cells exhibited surface FasR expression, albeit at a lower level than activated T cells. Based on these results, activated NK cells should be susceptible to FasL-mediated killing by FasCAR T cells.

Example 2: Derivation of FasR Knockout, FasL Expressing Cells

A. FasR Knockout

Two modifications were made to improve T cell persistence and reduce AICD: FasR gene knockout and FasL gene delivery.

Figures 3A, 3B:
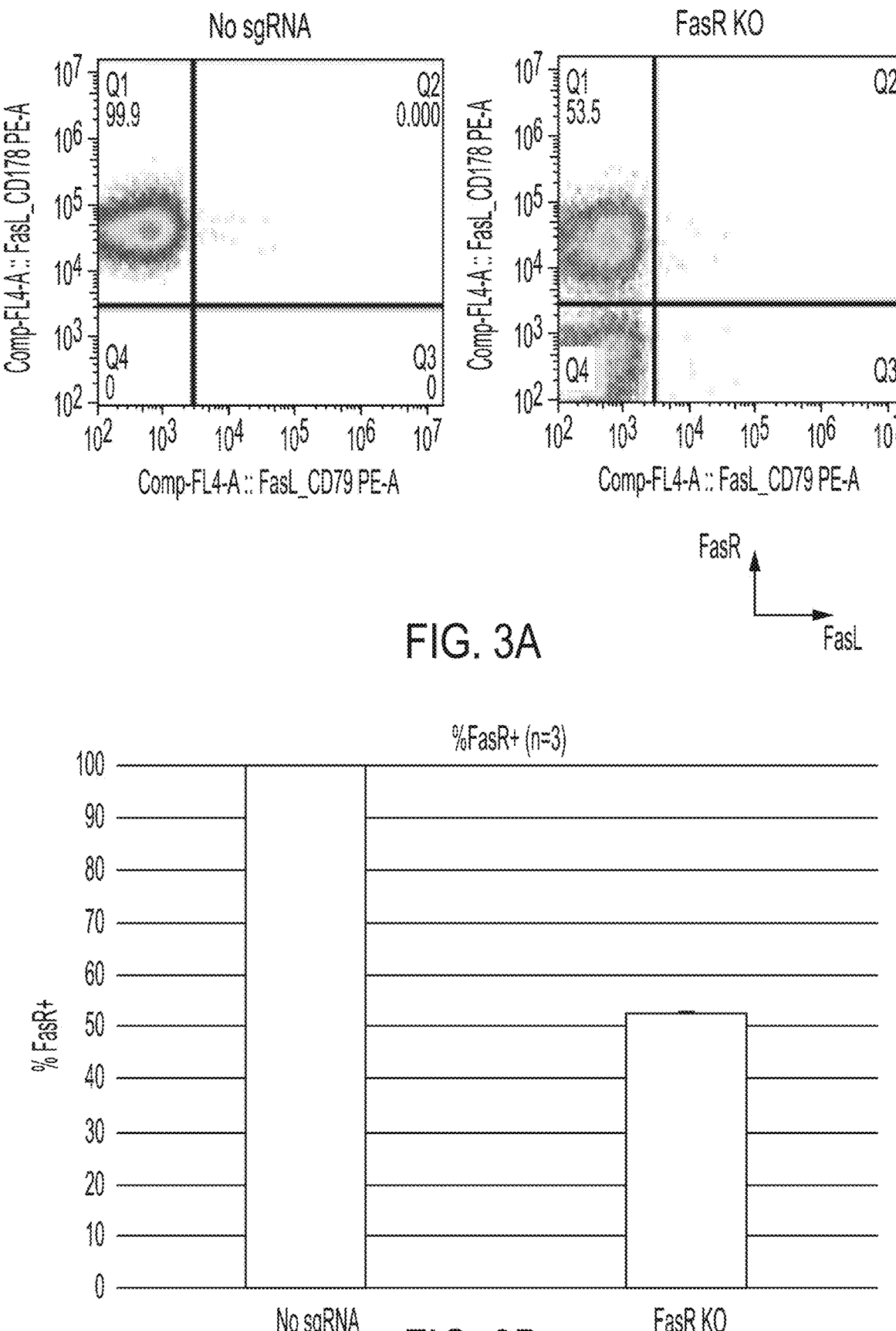
FIGS. 3A-3B. CRISPR-mediated knockout of the FasR gene in primary T cells.

CRISPR-mediated genome editing was used to knock out the FasR gene. Synthego's web tool was used to design single guide RNA (sgRNA) molecules targeting the human FasR gene for CRISPR-mediated knockout. Electroporation of the sgRNA and Cas9 enzyme into activated FasR+ primary T cells resulted in ~50% FasR gene knockout (FIGS. 3A and 3B).

Figure 4:
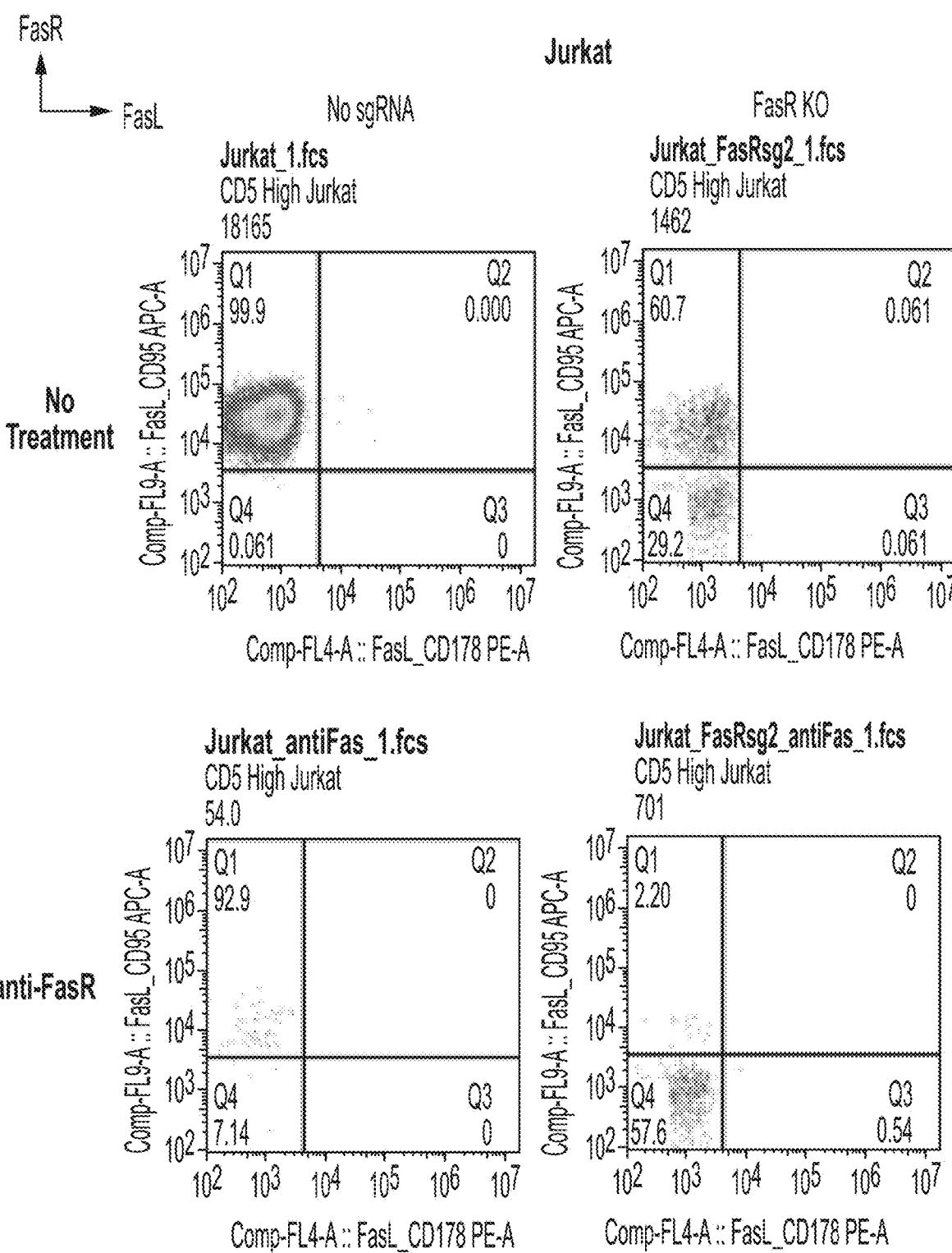
FIG. 4. FasR knockout protects Jurkat T cells from FasR-mediated apoptosis. Flow cytometry pseudocolored dot plots showing Jurkat cells or unpurified FasR KO Jurkat T cells incubated for 72 hours with media, 50 ng/mL apoptosis-inducing anti-FasR antibody (clone CH11), or 50 ng/mL antibody in the presence of 2 μg/mL FasR ectodomain-Fc competitive blocker.
Figure 4:
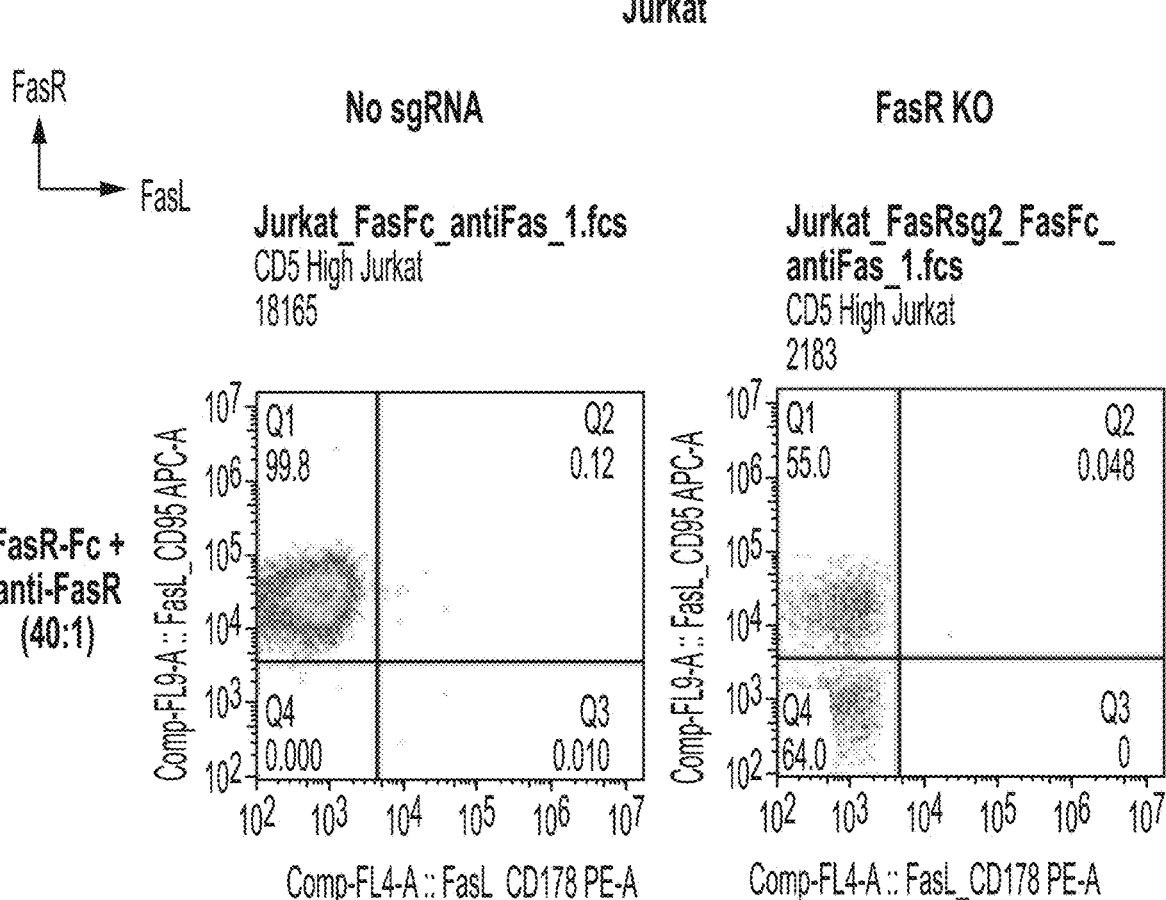

To demonstrate that FasR KO protects T cells from FasR-mediated apoptosis, FasR was knocked out in Jurkat T cells and cell death was evaluated in FasR+ versus FasR KO Jurkat cells following a 72 hour incubation with apoptosis-activating anti-FasR antibody (clone CH11, 50 ng/mL) or with antibody plus a competitive blocker (2 μg/mL FasR ectodomain-Fc) (FIG. 4). Incubation with anti-FasR antibody completely killed FasR+ Jurkat T cells. Competitively blocking antibody-FasR engagement with soluble FasR ectodomain prevented killing of FasR+ Jurkat cells, demonstrating the death via apoptosis was mediated specifically through FasR. By contrast, FasR knockout Jurkat T cells survived antibody incubation in the absence of competitive blockade, indicating the knockout effectively protected these cells from FasR-mediated apoptosis.

B. FasL Expression

Figure 5A:
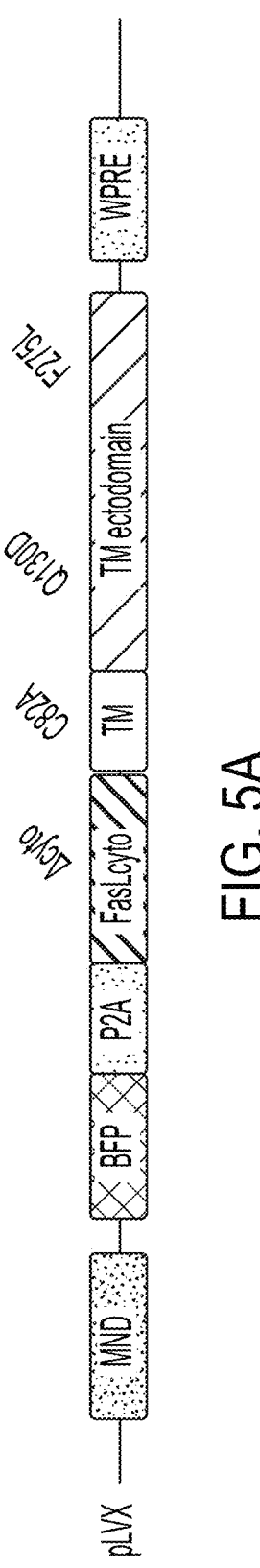
FIGS. 5A-5B. BFP and surface FasL expression on trans-duced primary T cells.
Figure 5B:
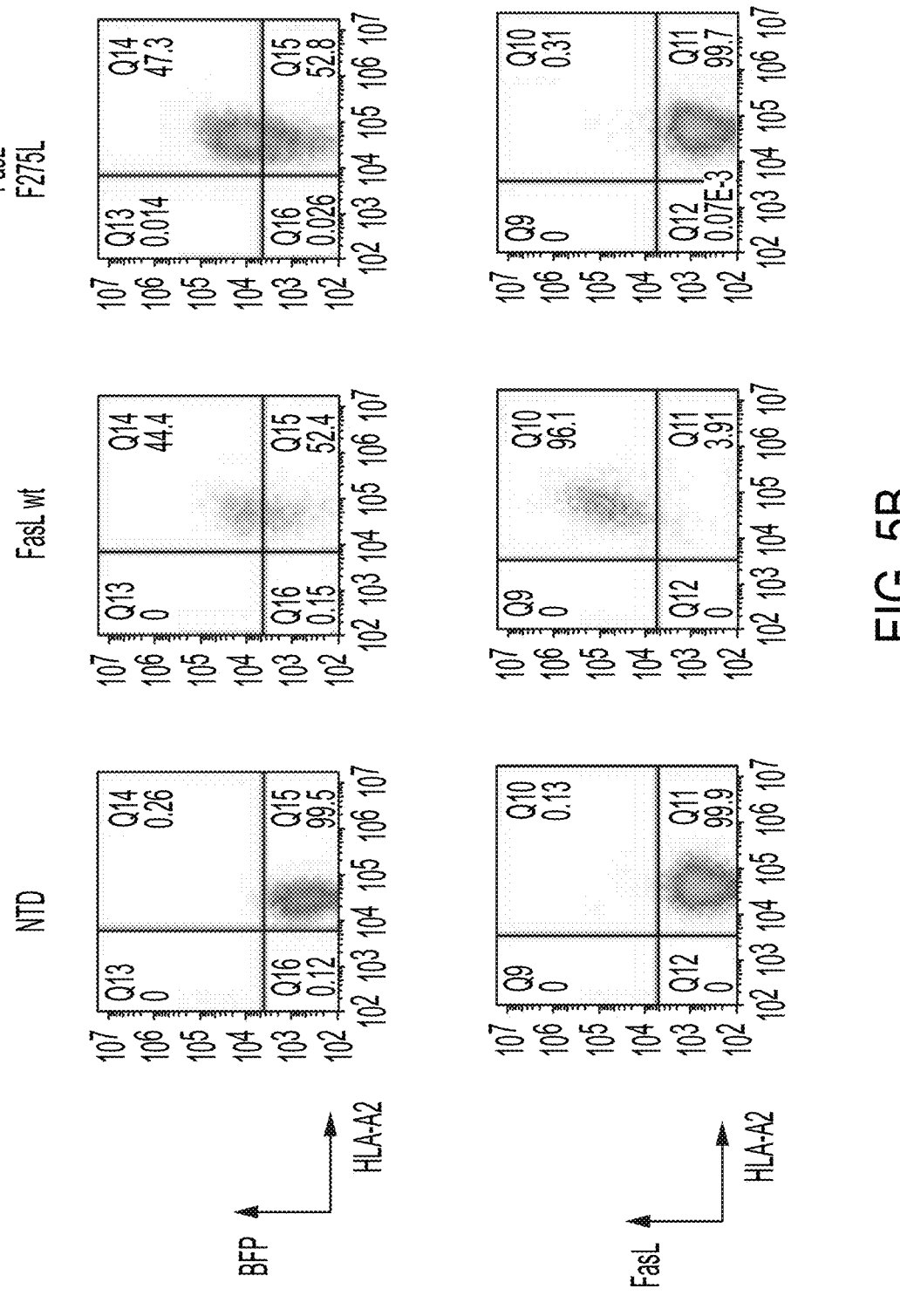
Figure 5B:
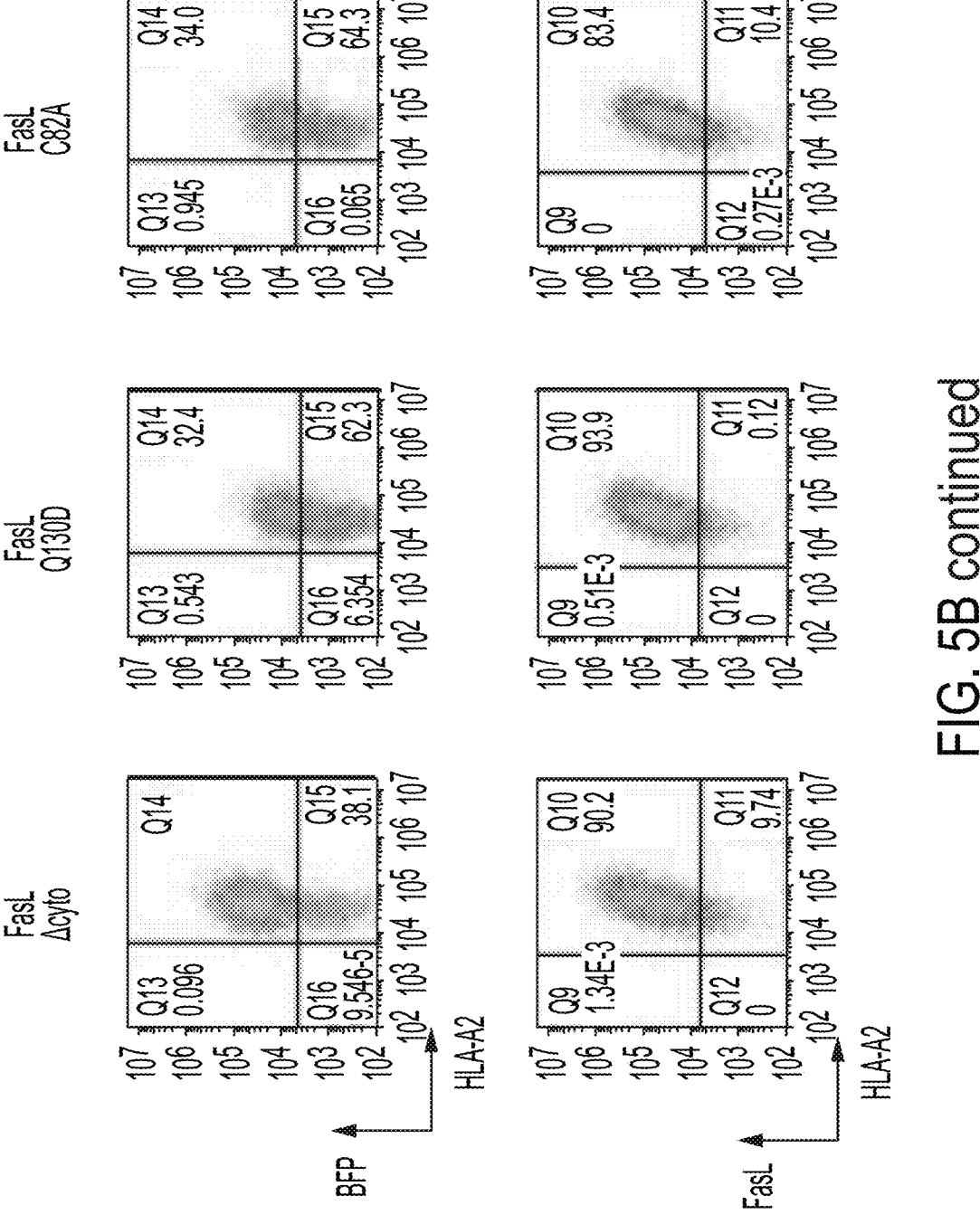

To enable FasL gene delivery, lentivectors were designed and prepared that co-delivered blue fluorescent protein (BFP) as a transduction marker with various derivatives of FasL, including wild-type human FasL (sequence from UniprotKB-P48023), an inactive mutant (F275L) (Schneider, P. et al., J. Biol. Chem. 272, 18827-18833 (1997).), a truncated form lacking the cytoplasmic domain (Aaa 2-74), and three mutants designed to disrupt the ADAM10 and SPPL2a cleavage sites on FasL (Q130D, C82A, and SLEKQ126-130→EEAAA (SEQ ID NOs: 32 and 33, respectively)). Lentivirus was prepared from a subset of these and was used to transduce primary T cells immediately following FasR knockout. Expression of BFP and surface expression of FasL on transduced T cells were evaluated with flow cytometry (FIGS. 5A and 5B). All vectors successfully transduced primary T cells, as evidenced by the expression of BFP in 30-70% of events depending on the construct. Additionally, all four active versions of FasL were observed on the cell surface, albeit with noticeably lower cellularity in the case of FasL wild-type. Notably, inactive (F275L) FasL was not detected on the cell surface despite robust BFP expression, indicating that this point mutation either disrupts biogenesis and export to the cell surface, or that the mutation that renders it non-functional also disrupts its recognition by the anti-FasL antibody used for flow cytometry staining.

Example 3: Pilot Experiments Testing the Function of FasL-Expressing, FasR KO T Cells A. FasL-Expressing T Cells Kill Autologous and Allogeneic Cells Expressing FasR.

Figure 6A:
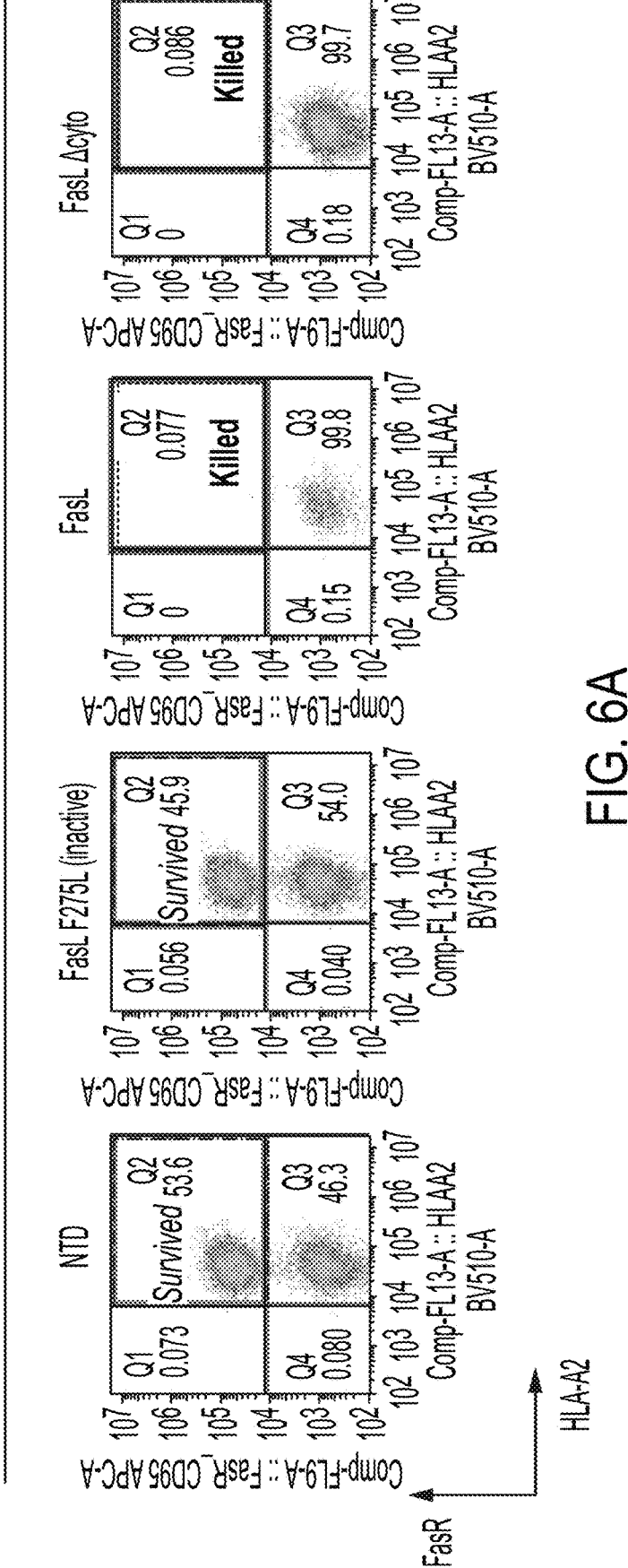
FIGS. 6A-6B. FasL-expressing T cells kill autologous and allogeneic cells expressing FasR. Flow cytometry pseudo-colored dot plots showing, in FIG. 6A, fratricidal killing of autologous FasR⁺ primary T cells one week after concurrent electroporation with Cas9-complexed FasR sgRNA and transduction (without purification for FasR knockout) with MND promoter-driven lentivectors delivering BFP and a derivative of Fas; and, in FIG. 6B, selective killing of FasR⁺ allogeneic HLA-A2− primary T cells by the FasL-modified HLA-A2⁺ cells from 6A. NTD, untransduced.
Figure 6B:
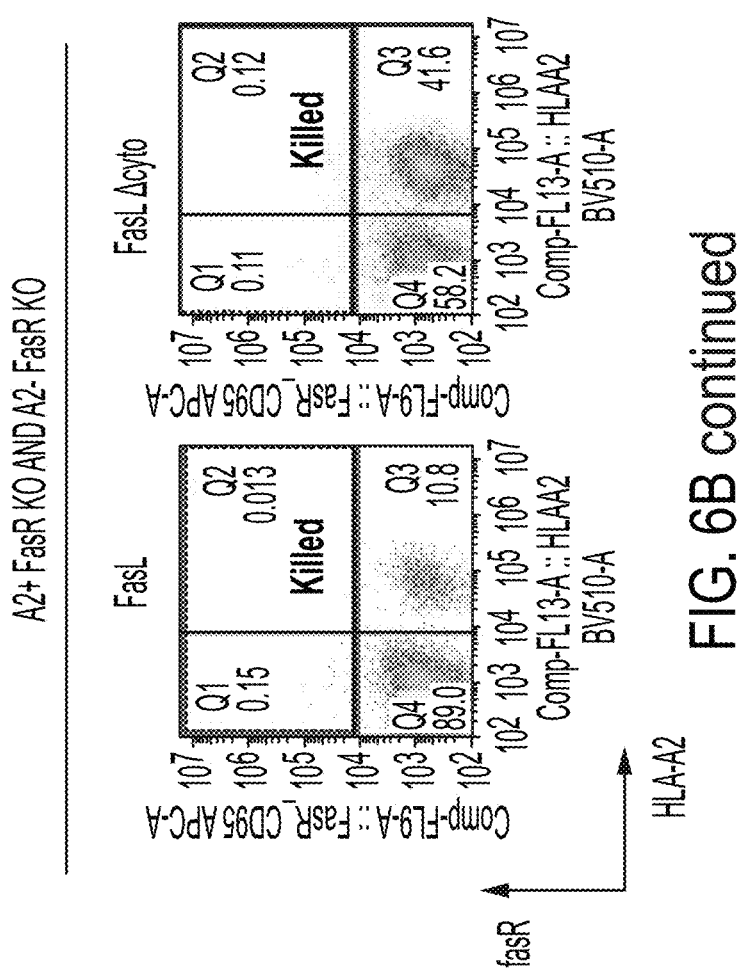

Importantly, FasR$^+$ cells (those in which FasR knockout did not occur) constituted ~50% of cells in untransduced (NTD) cells but were completely absent in those samples transduced with active forms of FasL (FIG. 6A), indicating FasR knockout is necessary to prevent fratricide of FasL-expressing T cell products. To investigate allogeneic cell killing on the basis of FasL-FasR engagement, we incubated the FasL$^+$, FasR KO (also referred to as "FasR$^-$") T cells generated in FIG. 6A from an HLA-A2$^+$ donor with FasR$^+$ and FasR$^-$ T cells from an HLA-A2$^-$ donor, and used HLA-A2 status to resolve the allogeneic cells during flow cytometry analysis. As predicted by the autologous fratricide observed in 6A, A2$^+$ FasR KO cells expressing an active form of FasL killed FasR$^+$ allogeneic cells but did not kill FasR$^-$ allogeneic cells (FIG. 6B). This suggests that FasL$^+$, FasR$^-$, CAR-expressing cell products can selectively kill activated allogeneic T cells (e.g. alloreactive T cells attacking the cell product) while sparing non-alloreactive host T cells. FasL$^+$, FasR$^-$, CAR-expressing cell products are therefore expected to persist longer and/or suffer less AICD than corresponding CAR-expressing cell products that are not FasL$^+$, FasR$^-$.

B. CRISPR-Mediated Dual Knockout of the FasR and β2m Genes in Primary T Cells.

Figures 7A, 7B:
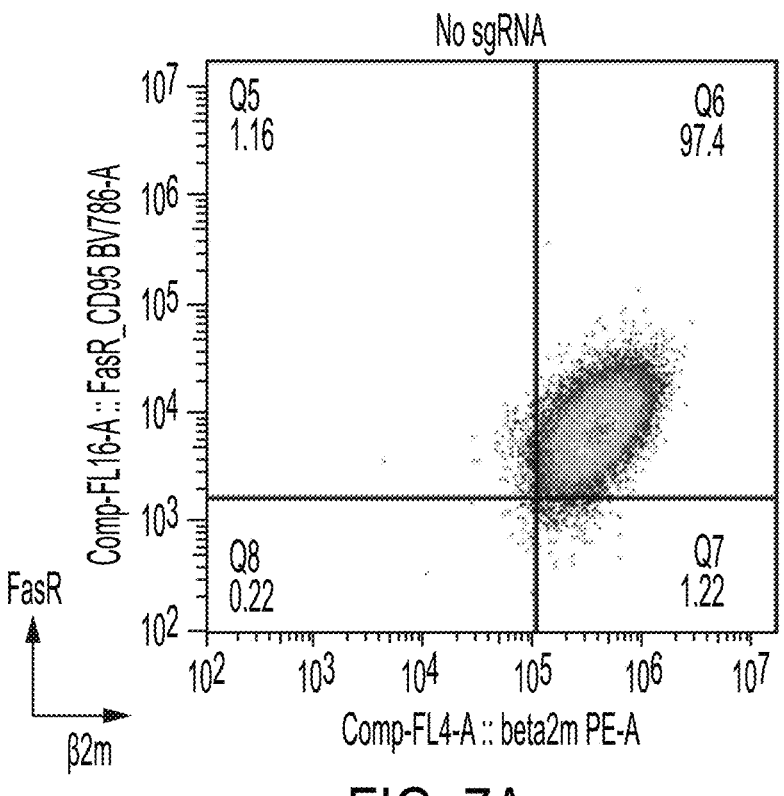
FIGS. 7A-7B. CRISPR-mediated dual knockout of the FasR and β2m genes in primary T cells. Flow cytometry pseudocolored dot plots showing FasR and β2m expression in activated primary T cells without (FIG. 7A) or with (FIG. 7B) electroporation of Cas9-complexed FasR and β2m sgRNA.

Allogeneic host T cells reject cell products based on TCR-mediated recognition of epitopes presented on non-self major histocompatibility complex (MEW) molecules. Allogeneic host NK cells may also contribute to rejection, particularly if cell therapy products are engineered to reduce MHC presentation to host T cells (e.g. by knocking out the invariant β2m component of MHCI molecules). To generate model FasL-expressing cells that are targets for allogeneic NK cells, we used CRISPR-mediated gene knockout to produce HLA-A2$^-$ T cells that are negative for FasR and β2m (FIGS. 7A and 7B) and then transduced these cells with FasL derivatives. The efficiency of FasR knockout was ~65% and the efficiency of β2m knockout was ~75%, with >50% of cells exhibiting knockout of both genes, as seen in FIG. 7B.

Figure 8A:
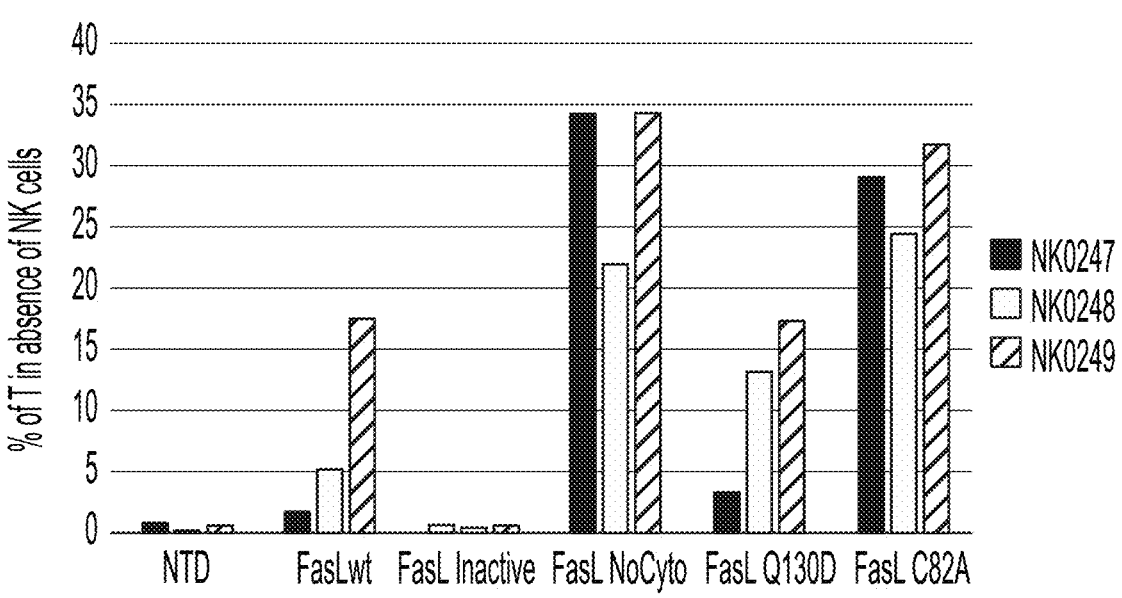
FIGS. 8A-8B. To determine if FasL expression protects these HLA-A2-model cell products from allogeneic NK cells, NK cells were prepared from fresh LRS chambers from three HLA-A2+ donors, activated with 1000 U/mL IL-2 for 48 hours, and then incubated with FasL-expressing, β2m KO cells for 72 hours, using HLA-A2 status to discern allogeneic cell origin by flow cytometry.
Figure 8B:
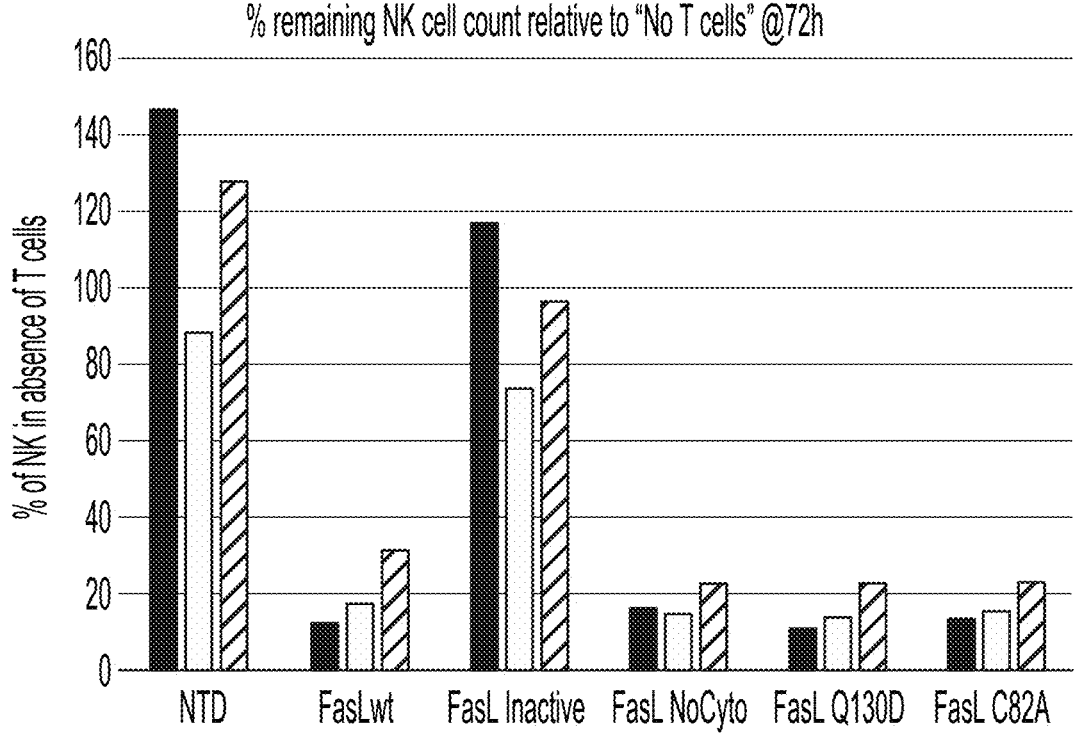
Figure 9A:
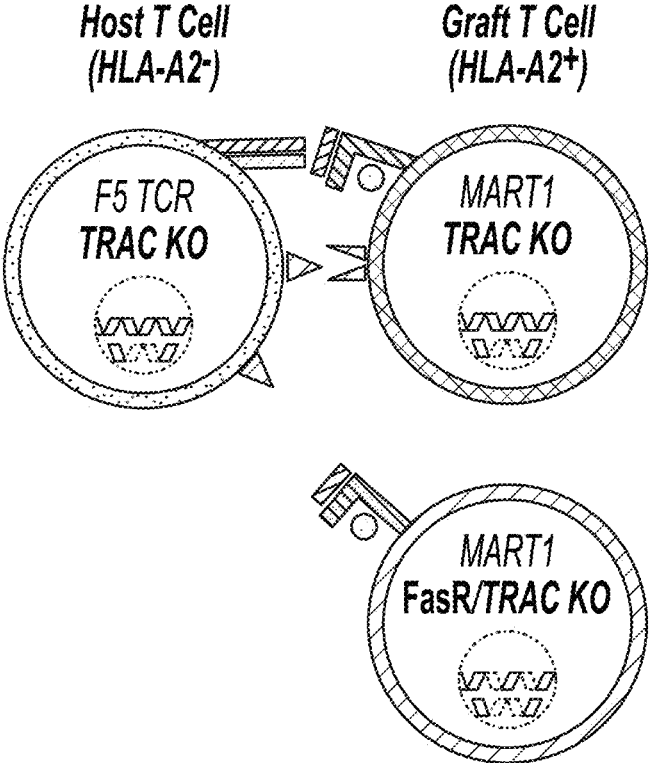
FIGS. 9A-9B. To determine if FasR KO on its own protects HLA-A2-model cell products from antigen-specific T cell-mediated killing, HLA-A2+ T cells were activated with TransAct for 72 hours, followed by TRAC±FasR gene knock out and transduction with mCherry-2A-full length MART1/Melan-A antigen. These are the HLA-A2+ mock "graft" cells with or without FasR KO. In parallel, HLA-A2− T cells were activated with TransAct for 72 hours, followed by TRAC knock out and transduction with HLA-A2-restricted, MART1 antigen-specific F5 TCR. These are the HLA-A2− mock "host" cells. Forty-eight hours post-transduction, mock graft/product and host/effector cells were co-incubated for 48 hours, and the remaining graft/product cells were quantified using HLA-A2 status to dis-cern allogeneic cell origin and mCherry/antigen status by flow cytometry.
Figure 9B:
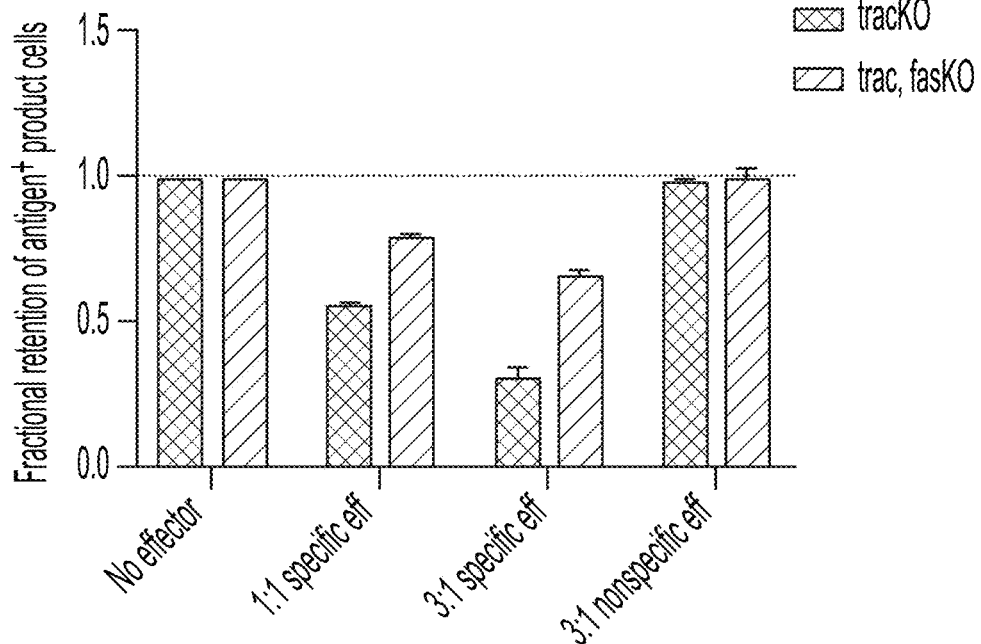

To determine if FasL expression protects these HLA-A2$^-$ model cell products from allogeneic NK cells, we prepared NK cells from fresh LRS chambers from three HLA-A2$^+$ donors, activated them with 1000 U/mL IL-2 for 48 hours, and then incubated them with FasL-expressing, β2m KO cells for 72 hours, using HLA-A2 status to discern allogeneic cell origin by flow cytometry (FIGS. 8A-8B). Activated NK cells completely killed β2m knockout cells that were either untransduced or transduced with inactive FasL. By contrast, β2m knockout cells were protected from NK cell-mediated killing when they expressed an active derivative of FasL (FIG. 8A). As hypothesized, the mechanism of this protection was FasL-mediated counterattack, as live NK cell counts were dramatically reduced in incubations including T cells armed with active FasL (FIG. 8B). This killing was specific for FasR$^+$ NK cells, as they were extirpated from these samples and all remaining NK cells were FasR$^-$ (data not shown).

---

What is claimed is:

1. An engineered immune cell comprising a vector, wherein the vector comprises a polynucleotide encoding an antigen binding protein and a polynucleotide encoding a FasL derivative selected from the group consisting of FasL Q130D (SEQ ID NO: 10) and FasL C82A (SEQ ID NO: 8).

2. The engineered immune cell of claim 1, further comprising a reduced level of FasR expression compared to non-engineered immune cells.

3. The engineered immune cell of claim 1, wherein the engineered immune cell has been genetically modified to express FasR at a reduced level compared to an engineered immune cell that is not genetically modified to express FasR at a reduced level.

4. The engineered immune cell of claim 3, wherein the engineered immune cell was genetically modified using any of a TALEN, CRISPR/Cas9, and a megaTAL nuclease, or exhibits a decreased expression level achieved using a shRNA or a micro RNA.

5. The engineered immune cell of claim 1, wherein the antigen binding protein is a chimeric antigen receptor (CAR).

6. The engineered immune cell of claim 1, wherein the engineered immune cell further comprises one or more genomic modifications to one or both of the endogenous TCRa gene and the endogenous CD52 gene.

7. The engineered immune cell of claim 1, wherein the engineered immune cell is a T cell.

8. The engineered immune cell of claim 1 wherein the FasL protein derivative comprises the amino acid sequence of FasL Q130D (SEQ ID NO: 10) and FasL C82A (SEQ ID NO: 8).

9. The engineered immune cell of claim 8, wherein the antigen binding protein is a chimeric antigen receptor (CAR).

10. The engineered immune cell of claim 8, wherein the cell further comprises genomic modifications of one or both of an endogenous TCRa gene and an endogenous CD52 gene.

11. The engineered immune cell of claim 10, wherein the cell comprises a loss-of-function genomic modification of TCRa.

12. The engineered immune cell of claim 10, wherein the cell comprises a loss-of-function genomic modification of CD52.

13. A population of engineered immune cells comprising one or more of the engineered immune cells of claim 1.

14. A population of engineered immune cells comprising $10^4$ or more, $10^5$ or more, or $10^6$ or more of the engineered immune cell of claim 1.

15. A pharmaceutical composition comprising the engineered immune cell of claim 1 and a pharmaceutically acceptable carrier.

16. A method of treating a condition in a patient wherein the condition is selected from the group consisting of a viral disease, a bacterial disease, a cancer, an inflammatory disease, and an immune disease, the method comprising intravenously administering to the patient therapeutically effective population of engineered T cells expressing an antigen binding protein and a Fas ligand (FasL) derivative selected from the group consisting of FasL Q130D (SEQ ID NO: 10) and FasL C82A (SEQ ID NO: 8) and wherein the engineered T cells further comprise a reduced level of expression of Fas receptor (FasR) compared to non-engineered T cells of at least 50%.

17. The method of claim 16, wherein the T cells are allogeneic cells derived from a donor other than the patient.

18. The method of claim 16, wherein the antigen binding protein is a chimeric antigen receptor (CAR).

19. The method of claim 16, wherein the engineered T cells further comprise one or more genomic modifications to one or both of the endogenous TCRa gene and the endogenous CD52 gene.

20. The method of claim 16, wherein the cancer is selected from the group consisting of acute lymphoblastic leukemia (ALL), acute myeloid leukemia (AML), chronic myelogenous leukemia (CML), chronic eosinophilic leukemia (CEL), myelodysplasia syndrome (MDS), non-Hodgkin's lymphoma (NHL), or multiple myeloma (MM) and a solid cancer selected from biliary cancer, bladder cancer, bone and soft tissue carcinoma, brain tumor, breast cancer, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, gynecological tumor, head and neck squamous cell carcinoma, hepatic cancer, lung cancer, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uterine sarcoma, and uterine cancer.

21. A method for reducing host cell killing of allogeneic cells in a therapeutic regimen comprising administering allogeneic cells to a patient, the method comprising intravenously administering to the patient a therapeutically effective population of engineered T-cells expressing an antigen binding protein and a FasL derivative selected from the group consisting of FasL Q130D (SEQ ID NO: 10) and FasL C82A (SEQ ID NO: 8) and wherein the engineered T cells further comprise a reduced level of expression of FasR compared to non-engineered T cells.

22. A method of enhancing the persistence of allogeneic cells in a patient comprising intravenously administering allogeneic cells to a patient, the method comprising administering to the patient a therapeutically effective population of engineered T cells expressing an antigen binding protein and a FasL derivative selected from the group consisting of FasL Q130D (SEQ ID NO: 10) and FasL C82A (SEQ ID NO: 8) and wherein the engineered T cells further comprise a reduced level of expression of FasR compared to non-engineered T cells of at least 50%.

* * * * *